(12) United States Patent
Kraus et al.

(10) Patent No.: US 9,207,247 B2
(45) Date of Patent: Dec. 8, 2015

(54) BIOMARKERS OF MUSCULOSKELETAL DISEASE

(75) Inventors: Virginia Kraus, Durham, NC (US); Christopher McCudden, Durham, NC (US); Jonathan Catterall, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/580,555

(22) PCT Filed: Feb. 22, 2011

(86) PCT No.: PCT/US2011/000316
§ 371 (c)(1),
(2), (4) Date: Aug. 22, 2012

(87) PCT Pub. No.: WO2011/102908
PCT Pub. Date: Aug. 25, 2011

(65) Prior Publication Data
US 2012/0315655 A1    Dec. 13, 2012

Related U.S. Application Data

(60) Provisional application No. 61/282,505, filed on Feb. 22, 2010.

(51) Int. Cl.
*G01N 33/53* (2006.01)
*C07K 16/00* (2006.01)
*G01N 33/68* (2006.01)

(52) U.S. Cl.
CPC ........ *G01N 33/6893* (2013.01); *G01N 2800/10* (2013.01)

(58) Field of Classification Search
CPC combination set(s) only.
See application file for complete search history.

(56) References Cited

U.S. PATENT DOCUMENTS

| 2004/0242987 A1 | 12/2004 | Liew et al. |
| 2005/0124071 A1 | 6/2005 | Kraus |
| 2010/0317699 A1 | 12/2010 | Armstrong et al. |

FOREIGN PATENT DOCUMENTS

| EP | 2258863 | 12/2010 |
| WO | WO 2009/095378 | 8/2009 |

OTHER PUBLICATIONS

Vilim et al., Clinica Chimica Acta 2003;vol. 328, pp. 59-69.*
Jordan et al, Arthritis and Rheumatism vol. 48,No. 3, pp. 675-681.*
International Search Report for PCT/US2011/000316 mailed Nov. 30, 2011.
N.E. Robinson et al., "Molecular Clocks", Proc Acad Sci ISA, Jan. 30, 2001, vol. 98, No. 3, pp. 944-999.
Supplementary European Search Report dated Sep. 20, 2013 issued in connection with EP 11 74 5006.
McCudden and Kraus, "Biochemistry of amino acid racemization and clinal application to musculoskeletal disease", Clinical Biochemistry 39:1112-1130 (2006).
Hooi et al, "Racemization of Two Proteins over Our Lifespan: Deamidation of Asparagine 76 in γS Crystallin Is Greater in Cataract than in Normal Lenses across the Age Range", Invest. Ophthalmol. Vis. Sci. 53:3554-3561 (2012).
Catterall et al, "Protein Modification by Deamidation indicates Variations in Joint Extracellular Matrix Turnover", The Journal of Biological Chemistry 287(7):4640-4651 (2012).
ATCC Deposit Receipts for Mouse hybridoma: 5-2G1—ATTCC Deposit Designation: PTA-11684; Mouse hybridoma: 5-3D9—ATTCC Deposit Designation: PTA-11685; Mouse hybridoma: 6-3B5—ATTCC Deposit Designation: PTA-11686; Mouse hybridoma: 6-1H3—ATTCC Deposit Designation: PTA-11687; Mouse hybridoma: 6-1A12—ATTCC Deposit Designation: PTA-11688; Mouse hybridoma: 6-1A10—ATTCC Deposit Designation: PTA-11689; Mouse hybridoma: 6-1B4—ATTCC Deposit Designation: PTA-11690; Deposited Feb. 17, 2011; ATCC, Mar. 11, 2011.
Robinson NE, Robinson AB. Deamidation of human proteins. Proc Natl Acad Sci U S A 2001;98(22):12409-13.
Bada JL, Protsch R. Racemization reaction of aspartic acid and its use in dating fossil bones. Proc Natl Acad Sci U S A 1973;70(5):1331-1334.

* cited by examiner

*Primary Examiner* — Shafiqul Haq
*Assistant Examiner* — Carmencita M Belei
(74) *Attorney, Agent, or Firm* — Andrus Intellectual Property Law, LLP

(57) ABSTRACT

The present invention relates, in general, to biomarkers of musculoskeletal disease and, in particular, to methods of diagnosing musculoskeletal disease, and/or predicting disease progression, by assaying for such biomarkers. The invention further relates to compounds and compositions suitable for use in such methods.

4 Claims, 38 Drawing Sheets

Figure 4
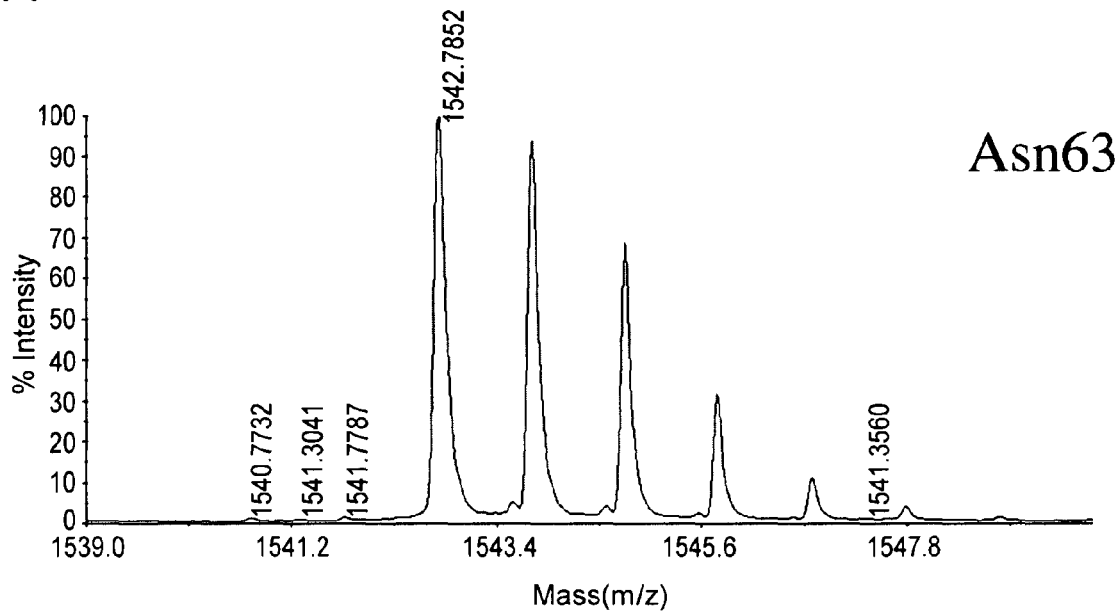
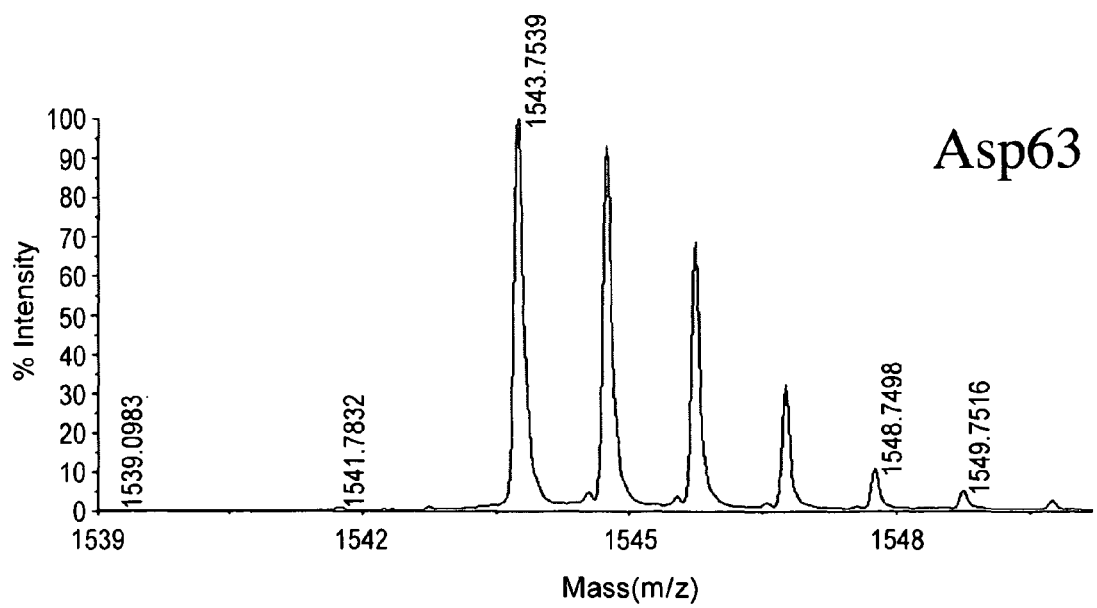

Association of COMP isoforms and hip and knee OA severity (p values)

| P-values | Hip-KL | Knee-KL | Knee-JSN | Knee-OST |
|---|---|---|---|---|
| Log Total COMP | 0.469 | <0.0001 | <0.0001 | <0.0001 |
| Log d-COMP | <0.0001 | 0.954 | 0.955 | 0.570 |

GLM/GEE analysis;

KL=Kellgren Lawrence OA severity

JSN=joint space narrowing of the knee

OST=osteophyte severity of the knee

Deamidated COMP (D COMP) increases incrementally with increasing severity of Hip Osteoarthritis (OA) and Total COMP (T COMP) increases incrementally with increasing severity of Knee OA.

Values for T-COMP and D-COMP and log transformed to achieve normal distributions for ANOVA. The values for T- and D-COMP are based on the same standard cartilage extract, containing T- and D-COMP based on Western blot. The absolute values therefore could vary if a different standard is used. Nevertheless, the relative differences of T- and D-COMP by KL grade here would be reflective of relative values achieved with different standards. Mean concentrations, standard errors and 95% confidence intervals are shown for individuals without OA (KL=0) of the joint (hip or knee) or with OA (KL$\geq$2). Number below represents number of individuals with the sum score indicated.

A. Ln D COMP and severity of Hip OA (KL) (p =0.0077)
Means for Oneway Anova
(KL=Kellgren Lawrence OA severity for the sum of both hips, higher value is more severe)

| KL | Number | Mean ln D-COMP | Std Error | Lower 95% | Upper 95% |
|---|---|---|---|---|---|
| 0 | 18 | 3.62404 | 0.38086 | 2.8755 | 4.3726 |
| 2 | 197 | 4.26147 | 0.11513 | 4.0352 | 4.4877 |
| 3 | 99 | 4.47006 | 0.16240 | 4.1509 | 4.7892 |
| 4 | 89 | 4.60756 | 0.17128 | 4.2709 | 4.9442 |
| 5 | 4 | 3.84736 | 0.80793 | 2.2594 | 5.4353 |
| 6 | 5 | 4.37456 | 0.72263 | 2.9543 | 5.7948 |
| 7 | 4 | 4.91952 | 0.80793 | 3.3316 | 6.5074 |

B. Ln T COMP and severity of Knee OA (KL) (p <0.0001)
Means for Oneway Anova
(KL=Kellgren Lawrence OA severity for the sum of both knees, higher value is more severe)

| KL | Number | Mean ln T-COMP | Std Error | Lower 95% | Upper 95% |
|---|---|---|---|---|---|
| 0 | 232 | 7.54875 | 0.02689 | 7.4959 | 7.6016 |
| 1 | 42 | 7.60865 | 0.06321 | 7.4844 | 7.7329 |
| 2 | 52 | 7.57904 | 0.05680 | 7.4674 | 7.6907 |
| 3 | 39 | 7.75539 | 0.06559 | 7.6265 | 7.8843 |
| 4 | 29 | 7.84638 | 0.07606 | 7.6969 | 7.9959 |
| 5 | 16 | 7.86418 | 0.10240 | 7.6629 | 8.0654 |
| 6 | 26 | 7.90407 | 0.08033 | 7.7462 | 8.0620 |
| 7 | 6 | 8.08534 | 0.16723 | 7.7567 | 8.4140 |
| 8 | 2 | 8.06470 | 0.28964 | 7.4954 | 8.6340 |

Figure 16 cont'd

C. Ln D COMP and severity of Knee OA (KL) (p=0.6355)
Means for Oneway Anova
(KL=Kellgren Lawrence OA severity for the sum of both knees, higher value is more severe)

| KL | Number | Mean ln D-COMP | Std Error | Lower 95% | Upper 95% |
|---|---|---|---|---|---|
| 0 | 234 | 4.22866 | 0.1071 | 4.0182 | 4.4391 |
| 2 | 53 | 4.30783 | 0.2250 | 3.8657 | 4.7500 |
| 3 | 39 | 4.21963 | 0.2623 | 3.7042 | 4.7351 |
| 4 | 29 | 4.27362 | 0.3041 | 3.6759 | 4.8714 |
| 5 | 16 | 4.33476 | 0.4095 | 3.5300 | 5.1395 |
| 6 | 26 | 4.56065 | 0.3212 | 3.9294 | 5.1919 |
| 7 | 6 | 3.16594 | 0.6686 | 1.8518 | 4.4801 |
| 8 | 2 | 4.51236 | 1.1581 | 2.2362 | 6.7885 |

D. Ln T COMP and severity of Hip OA (KL) (p=0.1814)
Means for Oneway Anova
(KL=Kellgren Lawrence OA severity for the sum of both hips, higher value is more severe)

| Level | Number | Mean ln T-COMP | Std Error | Lower 95% | Upper 95% |
|---|---|---|---|---|---|
| 0 | 17 | 7.49714 | 0.10324 | 7.2942 | 7.7000 |
| 2 | 196 | 7.61589 | 0.03040 | 7.5561 | 7.6756 |
| 3 | 99 | 7.67479 | 0.04278 | 7.5907 | 7.7589 |
| 4 | 89 | 7.65349 | 0.04512 | 7.5648 | 7.7422 |
| 5 | 4 | 7.69721 | 0.21283 | 7.2789 | 8.1155 |
| 6 | 5 | 7.79437 | 0.19036 | 7.4202 | 8.1685 |
| 7 | 4 | 8.14877 | 0.21283 | 7.7305 | 8.5671 |

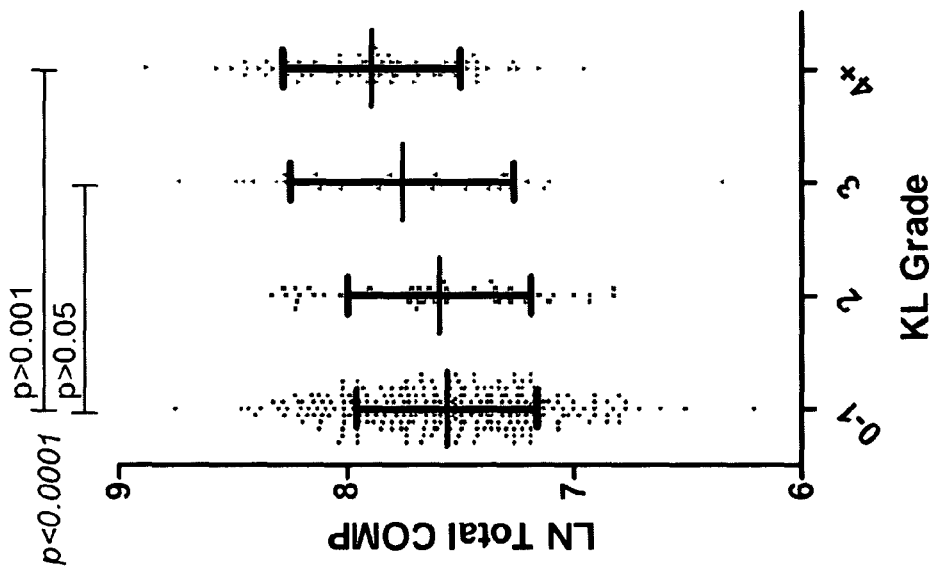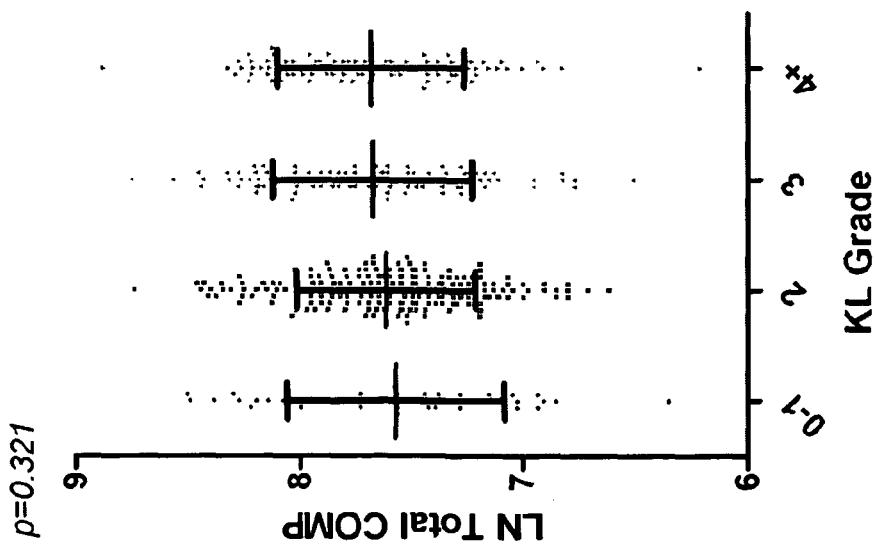
Figure 20

Figure 22
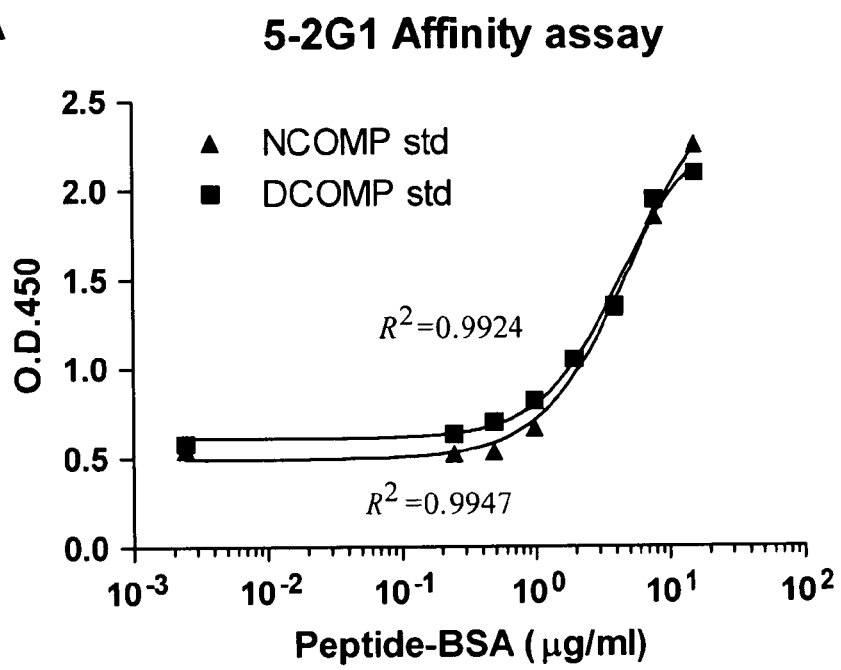
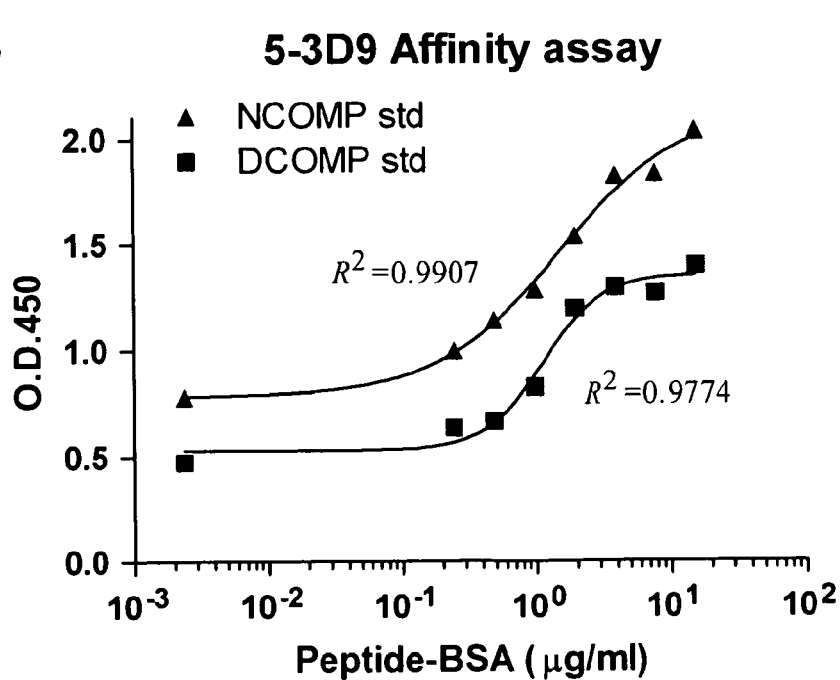

Figure 22
Total COMP mAb
C
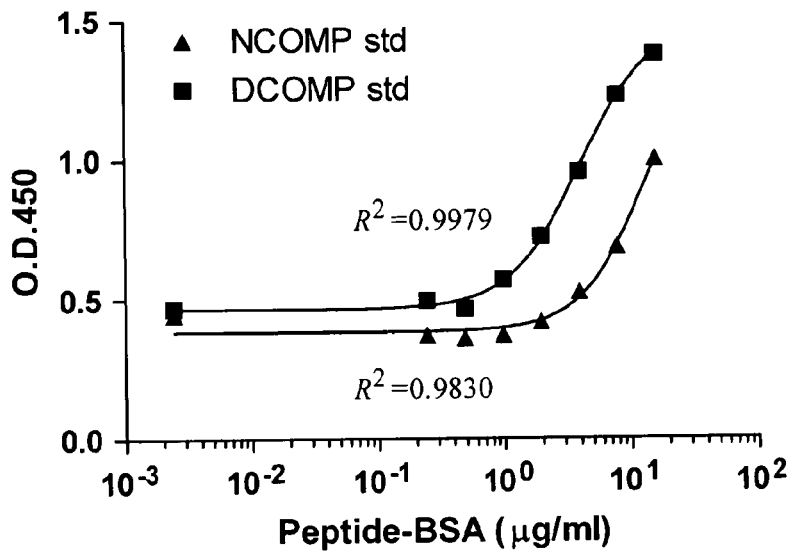
DCOMP specific mAb
D
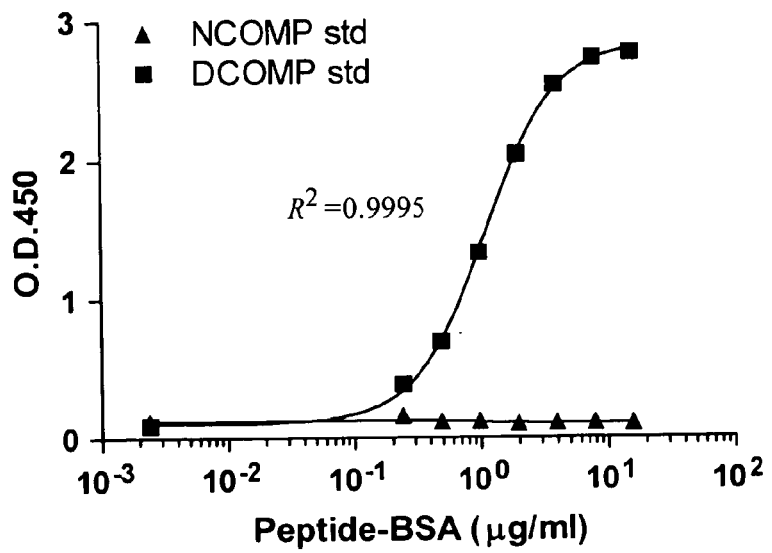

Figure 22
DCOMP specific mAb
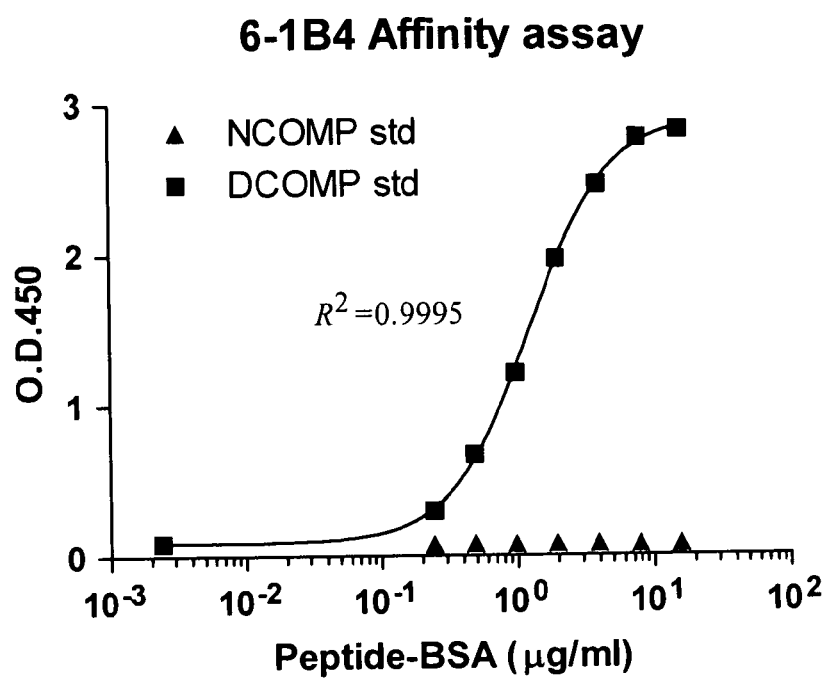
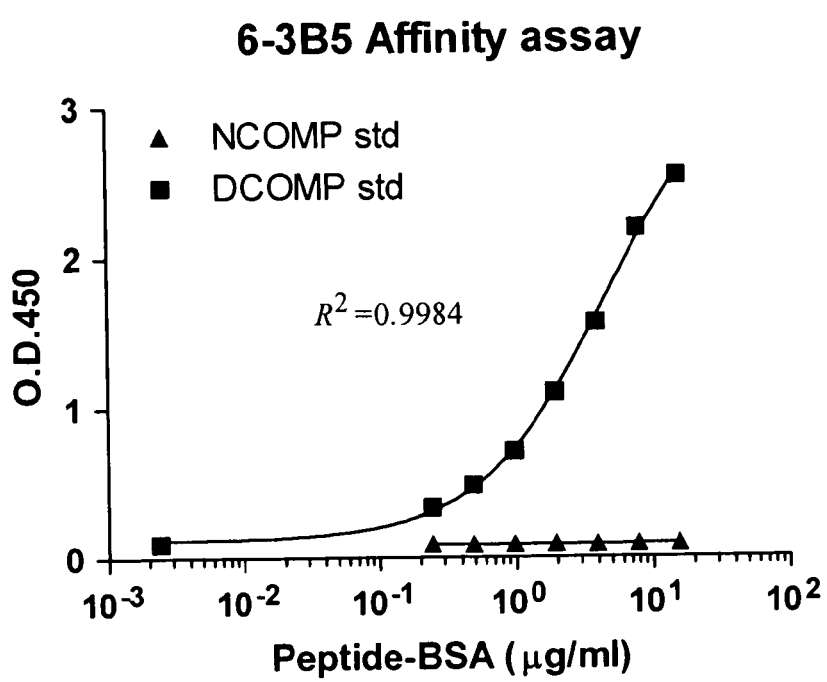

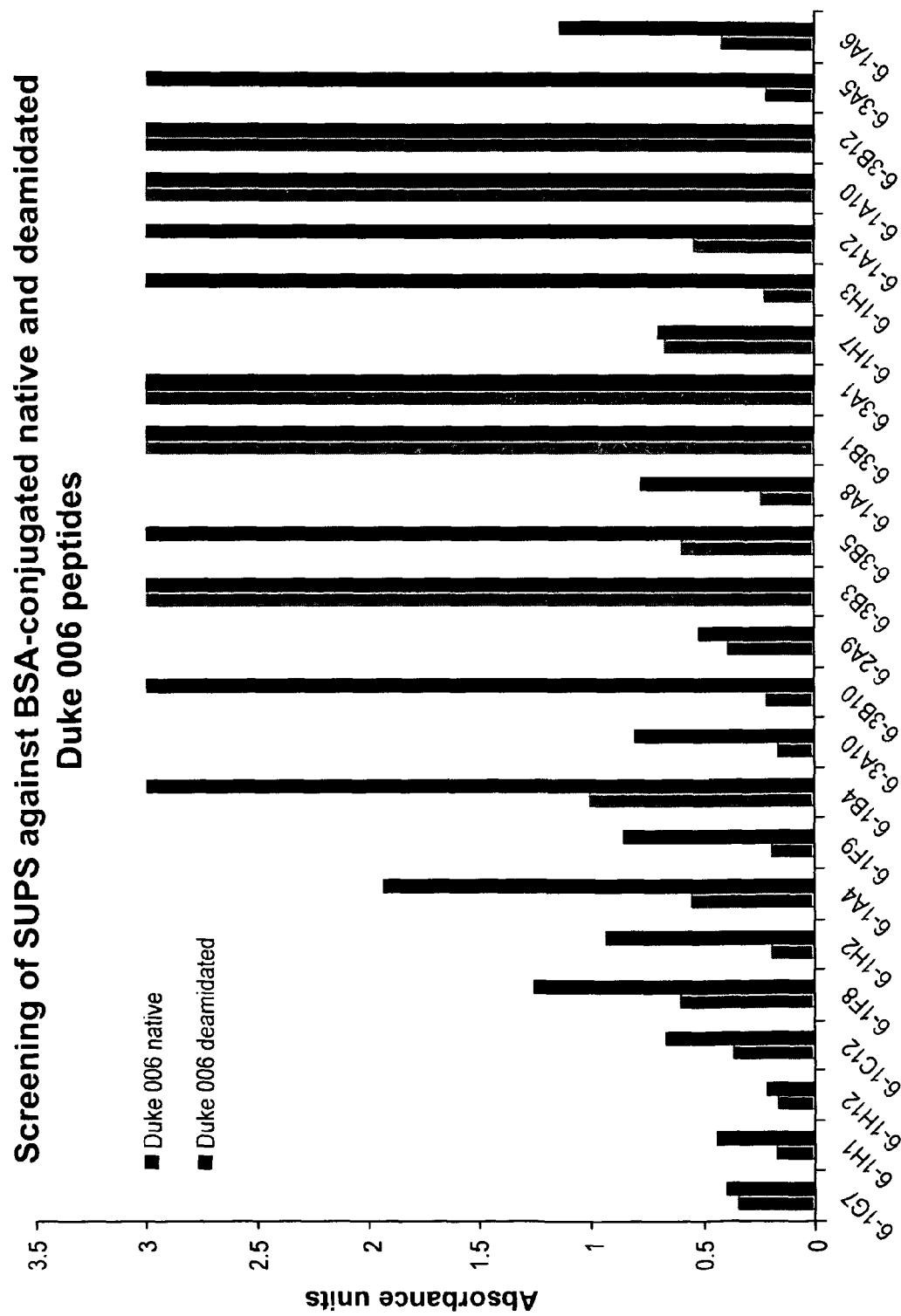

```
                           SEQUENCE LISTING

<160> NUMBER OF SEQ ID NOS: 24

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Leu Gln Glu Thr Asp Ala Ala Leu Gln
1               5                   10

<210> SEQ ID NO 2
<211> LENGTH: 10
<212> TYPE: PRT
<213> ORGANISM: Unknown
<220> FEATURE:
<223> OTHER INFORMATION: Description of Unknown: Native
      COMP peptide

<400> SEQUENCE: 2

Glu Leu Gln Glu Thr Asn Ala Ala Leu Gln
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Phe Leu Lys Asp Thr Val Met Glu Cys
1               5                   10

<210> SEQ ID NO 4
<211> LENGTH: 10
<212> TYPE: PRT
<213> ORGANISM: Unknown
<220> FEATURE:
<223> OTHER INFORMATION: Description of Unknown: Native
      COMP peptide

<400> SEQUENCE: 4

Thr Phe Leu Lys Asn Thr Val Met Glu Cys
1               5                   10

<210> SEQ ID NO 5
<211> LENGTH: 757
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (42)..(42)
<223> OTHER INFORMATION: Asp or Asn
<220> FEATURE:
<221> NAME/KEY: MOD_RES
```

<222> LOCATION: (64)..(64)
<223> OTHER INFORMATION: Asp or Asn

<400> SEQUENCE: 5

```
Met Val Pro Asp Thr Ala Cys Val Leu Leu Thr Leu Ala Ala Leu
1               5                   10                  15

Gly Ala Ser Gly Gln Gly Gln Ser Pro Leu Gly Ser Asp Leu Gly Pro
            20                  25                  30

Gln Met Leu Arg Glu Leu Gln Glu Thr Xaa Ala Ala Leu Gln Asp Val
            35                  40                  45

Arg Asp Trp Leu Arg Gln Gln Val Arg Glu Ile Thr Phe Leu Lys Xaa
50                  55                  60

Thr Val Met Glu Cys Asp Ala Cys Gly Met Gln Gln Ser Val Arg Thr
65                  70                  75                  80

Gly Leu Pro Ser Val Arg Pro Leu Leu His Cys Ala Pro Gly Phe Cys
                85                  90                  95

Phe Pro Gly Val Ala Cys Ile Gln Thr Glu Ser Gly Gly Arg Cys Gly
            100                 105                 110

Pro Cys Pro Ala Gly Phe Thr Gly Asn Gly Ser His Cys Thr Asp Val
            115                 120                 125

Asn Glu Cys Asn Ala His Pro Cys Phe Pro Arg Val Arg Cys Ile Asn
130                 135                 140

Thr Ser Pro Gly Phe Arg Cys Glu Ala Cys Pro Pro Gly Tyr Ser Gly
145                 150                 155                 160

Pro Thr His Gln Gly Val Gly Leu Ala Phe Ala Lys Ala Asn Lys Gln
                165                 170                 175

Val Cys Thr Asp Ile Asn Glu Cys Glu Thr Gly Gln His Asn Cys Val
            180                 185                 190

Pro Asn Ser Val Cys Ile Asn Thr Arg Gly Ser Phe Gln Cys Gly Pro
            195                 200                 205

Cys Gln Pro Gly Phe Val Gly Asp Gln Ala Ser Gly Cys Gln Arg Gly
            210                 215                 220

Ala Gln Arg Phe Cys Pro Asp Gly Ser Pro Ser Glu Cys His Glu His
225                 230                 235                 240

Ala Asp Cys Val Leu Glu Arg Asp Gly Ser Arg Ser Cys Val Cys Arg
                245                 250                 255

Val Gly Trp Ala Gly Asn Gly Ile Leu Cys Gly Arg Asp Thr Asp Leu
            260                 265                 270

Asp Gly Phe Pro Asp Glu Lys Leu Arg Cys Pro Glu Pro Gln Cys Arg
            275                 280                 285

Lys Asp Asn Cys Val Thr Val Pro Asn Ser Gly Gln Glu Asp Val Asp
290                 295                 300

Arg Asp Gly Ile Gly Asp Ala Cys Asp Pro Asp Ala Asp Gly Asp Gly
305                 310                 315                 320

Val Pro Asn Glu Lys Asp Asn Cys Pro Leu Val Arg Asn Pro Asp Gln
                325                 330                 335

Arg Asn Thr Asp Glu Asp Lys Trp Gly Asp Ala Cys Asp Asn Cys Arg
            340                 345                 350

Ser Gln Lys Asn Asp Asp Gln Lys Asp Thr Asp Gln Asp Gly Arg Gly
            355                 360                 365

Asp Ala Cys Asp Asp Asp Ile Asp Gly Asp Arg Ile Arg Asn Gln Ala
            370                 375                 380

Asp Asn Cys Pro Arg Val Pro Asn Ser Asp Gln Lys Asp Ser Asp Gly
385                 390                 395                 400
```

```
Asp Gly Ile Gly Asp Ala Cys Asp Asn Cys Pro Gln Lys Ser Asn Pro
            405                 410                 415

Asp Gln Ala Asp Val Asp His Asp Phe Val Gly Asp Ala Cys Asp Ser
        420                 425                 430

Asp Gln Asp Gln Asp Gly Asp Gly His Gln Asp Ser Arg Asp Asn Cys
        435                 440                 445

Pro Thr Val Pro Asn Ser Ala Gln Glu Asp Ser Asp His Asp Gly Gln
    450                 455                 460

Gly Asp Ala Cys Asp Asp Asp Asp Asn Asp Gly Val Pro Asp Ser
465                 470                 475                 480

Arg Asp Asn Cys Arg Leu Val Pro Asn Pro Gly Gln Glu Asp Ala Asp
                485                 490                 495

Arg Asp Gly Val Gly Asp Val Cys Gln Asp Asp Phe Asp Ala Asp Lys
            500                 505                 510

Val Val Asp Lys Ile Asp Val Cys Pro Glu Asn Ala Glu Val Thr Leu
    515                 520                 525

Thr Asp Phe Arg Ala Phe Gln Thr Val Val Leu Asp Pro Glu Gly Asp
    530                 535                 540

Ala Gln Ile Asp Pro Asn Trp Val Val Leu Asn Gln Gly Arg Glu Ile
545                 550                 555                 560

Val Gln Thr Met Asn Ser Asp Pro Gly Leu Ala Val Gly Tyr Thr Ala
                565                 570                 575

Phe Asn Gly Val Asp Phe Glu Gly Thr Phe His Val Asn Thr Val Thr
            580                 585                 590

Asp Asp Asp Tyr Ala Gly Phe Ile Phe Gly Tyr Gln Asp Ser Ser Ser
        595                 600                 605

Phe Tyr Val Val Met Trp Lys Gln Met Glu Gln Thr Tyr Trp Gln Ala
    610                 615                 620

Asn Pro Phe Arg Ala Val Ala Glu Pro Gly Ile Gln Leu Lys Ala Val
625                 630                 635                 640

Lys Ser Ser Thr Gly Pro Gly Glu Gln Leu Arg Asn Ala Leu Trp His
                645                 650                 655

Thr Gly Asp Thr Glu Ser Gln Val Arg Leu Leu Trp Lys Asp Pro Arg
            660                 665                 670

Asn Val Gly Trp Lys Asp Lys Lys Ser Tyr Arg Trp Phe Leu Gln His
        675                 680                 685

Arg Pro Gln Val Gly Tyr Ile Arg Val Arg Phe Tyr Glu Gly Pro Glu
    690                 695                 700

Leu Val Ala Asp Ser Asn Val Val Leu Asp Thr Thr Met Arg Gly Gly
705                 710                 715                 720

Arg Leu Gly Val Phe Cys Phe Ser Gln Glu Asn Ile Ile Trp Ala Asn
                725                 730                 735

Leu Arg Tyr Arg Cys Asn Asp Thr Ile Pro Glu Asp Tyr Glu Thr His
            740                 745                 750

Gln Leu Arg Gln Ala
        755

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 6

Cys Glu Leu Gln Glu Thr Asn Ala Ala Leu Gln
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Glu Leu Gln Glu Thr Asp Ala Ala Leu Gln
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Asp or Asn

<400> SEQUENCE: 8

Cys Glu Leu Gln Glu Thr Xaa Ala Ala Leu Gln
1               5                   10

<210> SEQ ID NO 9
<211> LENGTH: 73
<212> TYPE: PRT
<213> ORGANISM: Homo sapiens

<400> SEQUENCE: 9

Met Val Pro Asp Thr Ala Cys Val Leu Leu Thr Leu Ala Ala Leu
1               5                   10                  15

Gly Ala Ser Gly Gln Gly Gln Ser Pro Leu Gly Ser Asp Leu Gly Pro
            20                  25                  30

Gln Met Leu Arg Glu Leu Gln Glu Thr Asn Ala Ala Leu Gln Asp Val
        35                  40                  45

Arg Glu Leu Leu Arg Gln Gln Val Arg Glu Ile Thr Phe Leu Lys Asn
    50                  55                  60

Thr Val Met Glu Cys Asp Ala Cys Gly
65                  70

<210> SEQ ID NO 10
<211> LENGTH: 72
<212> TYPE: PRT
<213> ORGANISM: Rattus norvegicus

<400> SEQUENCE: 10

Met Ser Pro Thr Ala Cys Val Leu Val Leu Ala Leu Ala Ala Leu Arg
1               5                   10                  15

Ala Thr Gly Gln Gly Gln Ile Pro Leu Gly Gly Asp Leu Ala Pro Gln
            20                  25                  30

Met Leu Arg Glu Leu Gln Glu Thr Asn Ala Ala Leu Gln Asp Val Arg
        35                  40                  45

Glu Leu Leu Arg Gln Gln Val Lys Glu Ile Thr Phe Leu Lys Asn Thr
    50                  55                  60

Val Met Glu Cys Asp Ala Cys Gly
65              70

<210> SEQ ID NO 11
<211> LENGTH: 72
<212> TYPE: PRT
<213> ORGANISM: Mus musculus

<400> SEQUENCE: 11

Met Gly Pro Thr Ala Cys Val Leu Val Leu Ala Leu Ala Ile Leu Arg
1               5                   10                  15

Ala Thr Gly Gln Gly Gln Ile Pro Leu Gly Gly Asp Leu Ala Pro Gln
            20                  25                  30

Met Leu Arg Glu Leu Gln Glu Thr Asn Ala Ala Leu Gln Asp Val Arg
        35                  40                  45

Glu Leu Leu Arg Gln Gln Val Lys Glu Ile Thr Phe Leu Lys Asn Thr
    50                  55                  60

Val Met Glu Cys Asp Ala Cys Gly
65              70

<210> SEQ ID NO 12
<211> LENGTH: 73
<212> TYPE: PRT
<213> ORGANISM: Canis lupus

<400> SEQUENCE: 12

Met Val Pro Ala Ala Ala Cys Val Leu Leu Leu Thr Leu Ala Ala Leu
1               5                   10                  15

Gly Val Ser Gly Gln Gly Gln Ile Pro Leu Gly Ala Asp Leu Gly Pro
            20                  25                  30

Gln Met Leu Arg Glu Leu Gln Glu Thr Asn Ala Ala Leu Gln Asp Val
        35                  40                  45

Arg Glu Leu Leu Arg Gln Gln Val Lys Glu Ile Thr Phe Leu Lys Asn
    50                  55                  60

Thr Val Met Glu Cys Asp Ala Cys Gly
65                  70

<210> SEQ ID NO 13
<211> LENGTH: 72
<212> TYPE: PRT
<213> ORGANISM: Equus caballus

<400> SEQUENCE: 13

Met Val Leu Ser Ala Ala Pro Val Leu Leu Ala Leu Ala Leu Ala Leu
1               5                   10                  15

Val Ser Ser Gln Gly Gln Thr Pro Leu Gly Thr Glu Leu Gly Pro Gln
            20                  25                  30

Met Leu Arg Glu Leu Gln Glu Thr Asn Ala Ala Leu Gln Asp Val Arg
        35                  40                  45

Glu Leu Leu Arg Gln Gln Val Lys Glu Ile Thr Phe Leu Lys Asn Thr
    50                  55                  60

Val Met Glu Cys Asp Ala Cys Gly
65              70

<210> SEQ ID NO 14
<211> LENGTH: 73
<212> TYPE: PRT
<213> ORGANISM: Bos taurus

```
<400> SEQUENCE: 14

Met Val Leu Ala Ala Arg Val Leu Leu Thr Leu Ala Ala Leu
1               5                   10                  15

Gly Ala Ser Gly Gln Gly Gln Met Pro Leu Gly Gly Asp Leu Gly Pro
            20                  25                  30

Gln Met Leu Arg Glu Leu Gln Glu Thr Asn Ala Ala Leu Gln Asp Val
        35                  40                  45

Arg Asp Leu Leu Arg Gln Gln Val Lys Glu Ile Thr Phe Leu Lys Asn
    50                  55                  60

Thr Val Met Glu Cys Asp Ala Cys Gly
65                  70

<210> SEQ ID NO 15
<211> LENGTH: 73
<212> TYPE: PRT
<213> ORGANISM: Pan troglodytes

<400> SEQUENCE: 15

Met Val Pro Asp Thr Ala Cys Val Leu Leu Thr Leu Ala Ala Leu
1               5                   10                  15

Gly Ala Ser Gly Gln Gly Gln Ser Pro Leu Gly Ser Asp Leu Gly Pro
            20                  25                  30

Gln Met Leu Arg Glu Leu Gln Glu Thr Asn Ala Ala Leu Gln Asp Val
        35                  40                  45

Arg Glu Leu Leu Arg Gln Gln Val Arg Glu Ile Thr Phe Leu Lys Asn
    50                  55                  60

Thr Val Met Glu Cys Asp Ala Cys Gly
65                  70

<210> SEQ ID NO 16
<211> LENGTH: 73
<212> TYPE: PRT
<213> ORGANISM: Sus scrofa

<400> SEQUENCE: 16

Met Val Leu Thr Val Ala Arg Val Leu Leu Ile Thr Leu Ala Ala Leu
1               5                   10                  15

Gly Ala Ser Gly Gln Gly Gln Ile Thr Leu Gly Ala Asp Leu Gly Pro
            20                  25                  30

Gln Met Leu Arg Glu Leu Gln Glu Thr Asn Ala Ala Leu Gln Asp Val
        35                  40                  45

Arg Glu Leu Leu Arg Gln Gln Val Lys Glu Ile Thr Phe Leu Lys Asn
    50                  55                  60

Thr Val Met Glu Cys Asp Ala Cys Gly
65                  70

<210> SEQ ID NO 17
<211> LENGTH: 72
<212> TYPE: PRT
<213> ORGANISM: Gallus gallus

<400> SEQUENCE: 17

Met Ile Ser Ala Leu Ala Phe Val Phe Leu Cys Leu Ser Cys Pro
1               5                   10                  15

Phe Ser Ser Cys Gln Gln Arg Arg Ala Gly Ile Glu Val Gly Pro Glu
            20                  25                  30

Met Leu Glu Glu Met Arg Glu Thr Asn Arg Val Leu Met Glu Val Arg
        35                  40                  45
```

Asp Leu Leu Lys Gln Gln Ile Lys Glu Ile Thr Phe Leu Lys Asn Thr
        50                  55                  60

Val Met Glu Cys Asp Ala Cys Gly
 65                  70

<210> SEQ ID NO 18
<211> LENGTH: 73
<212> TYPE: PRT
<213> ORGANISM: Ailuropoda melanoleuca

<400> SEQUENCE: 18

Met Val Pro Ala Thr Ala Cys Val Leu Leu Thr Leu Ala Val Leu
 1               5                  10                  15

Gly Ala Ser Gly Gln Gly Gln Ile Ser Leu Gly Ala Asp Leu Gly Pro
                20                  25                  30

Gln Met Leu Arg Glu Leu Gln Glu Thr Asn Ala Ala Leu Gln Asp Val
            35                  40                  45

Arg Glu Leu Leu Arg Gln Val Lys Glu Ile Thr Phe Leu Lys Asn
        50                  55                  60

Thr Val Met Glu Cys Asp Ala Cys Gly
 65                  70

<210> SEQ ID NO 19
<211> LENGTH: 69
<212> TYPE: PRT
<213> ORGANISM: Xenopus tropicalis

<400> SEQUENCE: 19

Met Leu Ser Val Ala Leu Leu Ser Ser Phe Cys Ile Phe Phe Gly Ser
 1               5                  10                  15

Cys Gln Gln Leu Ser Gly Arg Gly Asp Val Gly Pro Gln Leu Leu Thr
                20                  25                  30

Glu Met Lys Glu Thr Asn Ser Val Leu Arg Glu Val Arg Glu Leu Leu
            35                  40                  45

Lys Arg Gln Ile Glu Glu Ile Thr Phe Leu Asn Thr Val Met Glu
        50                  55                  60

Cys Asp Ala Cys Gly
 65

<210> SEQ ID NO 20
<211> LENGTH: 74
<212> TYPE: PRT
<213> ORGANISM: Monodelphis domestica

<400> SEQUENCE: 20

Met Pro Leu Ser Pro Ser Leu Gly Leu Leu Leu Ala Phe Ala Cys
 1               5                  10                  15

His Leu Val Thr Gly Gln Arg Gln Ala Pro Val Gly Gly Asp Val Ala
                20                  25                  30

Pro Gln Met Leu Arg Glu Met Lys Glu Thr Asn Leu Val Leu Gln Glu
            35                  40                  45

Val Arg Glu Leu Leu Lys Gln Gln Ile Lys Glu Ile Thr Phe Leu Lys
        50                  55                  60

Asn Thr Val Met Glu Cys Asp Ala Cys Gly
 65                  70

<210> SEQ ID NO 21
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Glu Ile Thr Phe Leu Lys Asp Thr Val Met Glu Cys
1               5                   10

<210> SEQ ID NO 22
<211> LENGTH: 12
<212> TYPE: PRT
<213> ORGANISM: Unknown
<220> FEATURE:
<223> OTHER INFORMATION: Description of Unknown: Native
      COMP peptide

<400> SEQUENCE: 22

Glu Ile Thr Phe Leu Lys Asn Thr Val Met Glu Cys
1               5                   10

<210> SEQ ID NO 23
<211> LENGTH: 17
<212> TYPE: PRT
<213> ORGANISM: Unknown
<220> FEATURE:
<223> OTHER INFORMATION: Description of Unknown: Native
      COMP peptide

<400> SEQUENCE: 23

Asn Thr Val Met Glu Cys Asp Ala Cys Gly Met Gln Gln Ser Val Cys
1               5                   10                  15

Arg

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Thr Val Met Glu Cys Asp Ala Cys Gly Met Gln Gln Ser Val Cys
1               5                   10                  15

Arg
```

BIOMARKERS OF MUSCULOSKELETAL DISEASE

This application is the U.S. national phase of International Application No. PCT/US2011/000316 filed 22 Feb. 2011 which designated the U.S. and claims priority from U.S. Provisional Application No. 61/282,505, filed Feb. 22, 2010, the entire content of each of which is incorporated herein by reference.

This invention was made with government support under Grant No. U01-AR050898 awarded by the National Institutes of Health. The government has certain rights in the invention.

TECHNICAL FIELD

The present invention relates, in general, to biomarkers of musculoskeletal disease and, in particular, to methods of diagnosing musculoskeletal disease, monitoring disease burden, and/or predicting disease progression by assaying for such biomarkers. The invention further relates to compounds and compositions suitable for use in such methods.

BACKGROUND

Musculoskeletal diseases include a multitude of disorders that are prevalent in aging populations (Picavet and Hazes, Ann. Rheum. Dis. 62(7):644-650 (2003), Leveille, Curr. Opin. Rheumatol. 16(2):114-118 (2004), Harkness et al, Rheumatology (Oxford) 44(7):890-895 (2005)). Global population studies and World Health Organization statistics indicate that 10-50% of individuals suffer from musculoskeletal disorders and up to 3% will be classified as disabled due to their bone and joint conditions (Kean and Buchanan, Inflammopharmacology 13(4):343-370 (2005)). The most widely occurring forms of musculoskeletal disease are osteoporosis and osteoarthritis (OA). Globally, OA is estimated to affect 9.6% of men and 18% of women ≥60 years old (Woolf and Pfleger, Bull. World Health Organ. 81(9):646-656 (2003)). Osteoporosis affects as much as 30% of the postmenopausal women in the US, and 23% of women aged ≥50 in the UK (Woolf and Pfleger, Bull. World Health Organ. 81(9):646-656 (2003)). The growing physical and financial burden of these diseases has lead to the research and development of numerous musculoskeletal disease related biomarkers, many of which are fragments of long-lived proteins.

Cartilage is composed of two major protein constituents, collagen II and proteoglycan (Kuettner et al, Modern aspects of articular cartilage biochemistry, Cartilage Changes in Osteoarthritis, K. Brandt, Ciba Geigy, 3-11 (1990)). Proteoglycans, entrapped in the collagen network, make up ~40% of the dry weight of cartilage. The proteoglycan component plays a crucial role in the structure of cartilage by endowing the tissue with its ability to reversibly absorb loads (Kuettner et al, Modern aspects of articular cartilage biochemistry, Cartilage Changes in Osteoarthritis, K. Brandt, Ciba Geigy, 3-11 (1990)), so-called compressive stiffness. Aggrecan is the major proteoglycan found in articular cartilage forming the protein component of the hydrated gel matrix (Cs-Szabo et al, Arthritis Rheum. 38(5):660-668 (1995), Knudson and Knudson, Semin. Cell Dev. Biol. 12(2): 69-78 (2001), Kiani et al, Cell Res. 12(1):19-32 (2002)). Collagen II makes up ~60% of the dry weight of cartilage and provides tensile stiffness and strength. Collagen architecture of normal articular cartilage consists of layers of flat ribbons parallel to the surface, vertical columns in the intermediate zone and a random meshwork in the deep zone (Hwang et al, J. Pathol. 167:425-433 (1992)). Cartilage, like bone, is in a continual state of resorption and formation.

A number of studies have found evidence for an enhanced synthesis of extracellular matrix components in OA (Lippiello et al, J. Clin. Invest. 593-600 (1977); Eyre et al, Biochem. J. 823-837 (1980); Mankin et al, J. Bone Joint Surg. 131-139 (1981)). By enhancing their anabolic or formation activity, chondrocytes attempt to repair the damaged matrix. Little is currently known about the capacity of different joints to repair damaged matrix or about the balance between degradation and repair for different joint sites.

More is known about the balance between degradation and repair at a protein level. One of the key factors in the etiology of musculoskeletal diseases is altered protein turnover. In altered protein turnover, the degradation and synthesis pathways in a tissue become dysregulated, resulting either in excess production or degradation. In OA, the physiological balance between extracellular matrix synthesis and degradation is altered in favor of degradation. This appears to be due to a cell-mediated upregulation of normal degradative processes in combination with the synthesis of poorly assembled matrix pools of molecules (Quinn et al, Ann. N.Y. Acad. Sci. 878:420-441 (1999)). Type II collagen is degraded by interstitial collagenases, a class of matrix metalloproteinases (MMPs) that possess the unique ability to cleave an intact triple helical collagen fibril (Eyre, Arthritis Res. 4(1):30-35 (2002), Eyre, Clin. Orthop. Relat. Res. (427 Suppl):S118-S122 (2004)). Damage to the fibrillar meshwork of cartilage is considered a serious and irreversible occurrence due to the slow rate of collagen turnover within cartilage. The catabolism of aggrecan is also mediated by a unique sub-group of metalloproteinases known as aggrecanases or ADAMTS (Nagase and Kashiwagi, Arthritis Res. Ther. 5(2):94-03 (2003)). The release of small molecular weight G1-bearing (globular fragment) species of aggrecan is commonly interpreted as a final stage in chondrocyte-mediated proteoglycan metabolism (Quinn et al, Ann. N.Y. Acad. Sci. 878:420-441 (1999)). Both type II collagen and aggrecan are degraded over the course of OA, are detectable in body fluids, and can be used as a measure of cartilage degradation.

Non-enzymatic modification of protein constitutes a byproduct of aging with potential biologic consequences. Non-enzymatic modifications that can occur in vivo include deamidation, oxidation, nitration, glycation, and racemization. Deamidation is believed to be a mechanism of amino acid damage and aging in numerous proteins and a variety of tissues (Robinson and Robinson, Molecular Clocks: Deamidation of Asparaginyl and Glutaminyl Residues in Peptides and Proteins, Cave Junction, Oreg., Althouse Press (2004)). Both asparagine (Asn) and glutamine (Gln) can be deamidated to form aspartate (Asp) and glutamate (Glu), respectively. Deamidation rates for Asn are usually faster than for Gln (Robinson and Robinson, Molecular Clocks: Deamidation of Asparaginyl and Glutaminyl Residues in Peptides and Proteins, Cave Junction, Oreg., Althouse Press (2004)). In fact, deamidation of Asn is thought to be possibly the single greatest means of producing protein damage under conditions of neutral pH (Aswad, Promega Notes Magazine 52:27 (1995)).

Deamidation rates are increased by increases in temperature, ionic strength, and pH (especially above pH 6). "Hot spots" for deamidation are predicted to exist as deamidation is known to vary based on factors such as steric hindrance and protein context (Robinson and Robinson, Molecular Clocks: Deamidation of Asparaginyl and Glutaminyl Residues in Peptides and Proteins, Cave Junction, Oreg., Althouse Press (2004), pp 97-116). For instance, particular peptide sequences are known to deamidate more readily than others, including GlyAsn, AsnGly and GlnGly (Robinson and Robinson, Molecular Clocks: Deamidation of Asparaginyl and Glutaminyl Residues in Peptides and Proteins, Cave Junction, Oreg., Althouse Press (2004)). Because joint tissues are at physiological pH or lower, this would tend to slow the overall rate of deamidation in joint tissues, particularly cartilage.

Protein turnover (anabolism and catabolism) rates can be used as a measure of tissue health in musculoskeletal disease. This is best exemplified by the use of type I collagen biomarkers for the monitoring of osteoporosis (Garnero, Mol. Diagn. Ther. 2008; 12(3):157-70 (2008)). Although a number of biomarkers have been associated with OA, none is yet approved for clinical use. Moreover, current biomarkers do not allow for the age of a given protein or protein fragment to be estimated or to be taken into account.

The present invention relates to methods of quantifying aged proteins and protein fragments (e.g., deamidated fragments of cartilage oligomeric matrix protein (COMP)) in body fluids, and thereby differentiating newly synthesized material from material derived by degradation of older resident molecules. By distinguishing older breakdown products from new protein fragments or total fragments (that is, fragments of all ages), the invention makes possible diagnostic, joint specific, and/or prognostic analyses of musculoskeletal diseases.

SUMMARY OF THE INVENTION

The invention relates generally to biomarkers of musculoskeletal disease. More specifically, the invention relates to a method of diagnosing musculoskeletal disease, quantifying burden of disease, monitoring response to intervention, and/or predicting disease progression by assaying for such biomarkers. The invention also relates to compounds and compositions suitable for use in such methods.

Objects and advantages of the present invention will be clear from the description that follows.

BRIEF DESCRIPTION OF THE DRAWINGS

FIGS. 4A-4C. MS spectrum of the peptide Asp 63 of Duke 006 peptide. FIG. 4A. Native epitopes. FIG. 4B. Deamidated epitopes. FIG. 4C. Mixture of native and deamidated epitopes.

FIG. 8A. 10% reduced SDS-PAGE Western blot using mAb 12C4 to native COMP (provided as a gift from Dr. Vladimir Vilim), and mAb 5-3D4 that recognizes both native and deamidated COMP. FIG. 8B. 5-20% gradient non-reduced SDS-PAGE Western blot using mAb 6-3A5 specific for deamidated COMP and mAb 6-3B12 that binds both native and deamidated COMP with a preference for deamidated COMP.

FIGS. 9A-9E. Competition data with peptide demonstrating antibody specificities. FIG. 9A. Antibody 6-1A12 specific for Duke 006 B-BSA. FIG. 9B. Antibody 6-3B10 specific for Duke 006 B-BSA. FIG. 9C. Antibody 6-3A1 specific for both Duke 006 A-BSA and Duke 006 B-BSA (FIG. 9D). FIG. 9E. Antibody 5-3D4 specific for both deamidated (not shown) and non-deaminated Duke 005 A-BSA.

FIG. 10A. Competition ELISA scheme using BSA-peptide. FIG. 10B. Sandwich ELISA scheme using combination of two antibodies.

FIG. 11A. Constant antibody concentration with variable coating concentration. FIG. 11B. Standard curves for dCOMP competition ELISA. FIG. 11C. Typical standard curve for dCOMP competition ELISA using mAb 6-1A12.

FIG. 13A. Synovial fluid total COMP versus age. FIG. 13B. Synovial fluid deamidated COMP versus age. FIG. 13C. Ratio of synovial fluid deamidated COMP/total COMP (i.e., D-COMP/N-COMP Ratio) versus age.

FIG. 14A. Total-COMP in serum and D-COMP in serum before and 6 months after joint replacement surgery in all patients (n=15). FIG. 14B. Total-COMP in serum and D-COMP in serum before and 6 months after hip replacement (n=4). [left side]; Total-COMP in serum and D-COMP in serum before and 6 months after knee replacement (n=11) [right side]. FIG. 14C. dCOMP and Total COMP concentrations in cartilage from hip OA and knee OA (dCOMP hip>knee; Total COMP knee>hip). D-COMP and Total-COMP concentrations were normalized to total protein in cartilage.

FIG. 15. Table showing association of COMP isoforms in serum and hip and knee OA severity. These statistical results were generated using the SAS GLM/GEE procedure thereby controlling for within subject correlation of the two knee joints or the two hip joints.

FIGS. 16A-16D. Tables showing d-COMP increases incrementally with increasing severity of Hip Osteoarthritis (OA) and Total-COMP increases incrementally with increasing severity of Knee OA. The means and 95% confidence intervals represented are natural logarithmic values. FIG. 16A. Ln d-COMP and severity of Hip OA: FIG. 16B. Ln Total-COMP and severity of Knee OA. FIG. 16C. Ln d-COMP and severity of Knee OA; FIG. 16D. Ln Total-COMP and severity of Hip OA.

FIG. 17A. Screening of mAbs against deamidated and native COMP peptides. Two native COMP BSA-peptide constructs, $Asn_{42}$ (BSA-CELQETN$_{42}$AALQ) (SEQ ID NO: 6) (N-terminal C added for coupling purposes) and $Asn_{64}$ (TFLKN$_{64}$TVMEC (SEQ ID NO:4)-BSA), and the corresponding two deamidated BSA constructs, $Asp_{42}$ (BSA-CELQETD$_{42}$AALQ) (SEQ ID NO: 7) (N-terminal C added for coupling purposes) and $Asp_{64}$ (TFLKD$_{64}$TVMEC (SEQ ID NO:3)-BSA) were coated onto 96 well plates. Hybridoma culture media were incubated with the coated plates for 2 hr before addition of goat anti-mouse-AP secondary antibody and ELISA development using OPD substrate. A negative control containing no primary antibody was included and a mAb (5-2G1) raised against CELQETD$_{42}$AALQ) (SEQ ID NO: 7) was used to confirm immunoreactivity for the BSA-CELQET(N/D)$_{42}$AALQ (SEQ ID NO: 8) peptide. Screening yielded a total of 5 deamidation independent (immunoreactivity to Asn$_{64}$ and Asp$_{64}$) and 11 deamidation dependent mAbs (preferential immunoreactivity to Asp$_{64}$). FIG. 17B. Screening of mAbs against purified cartilage COMP. Purified COMP protein (a gift from V. Vilm) was coated onto 96 well plates. Hybridoma culture media were incubated with the coated plates for 2 hr before addition of goat anti-mouse-AP secondary antibody and ELISA development using OPD substrate. A negative control containing no primary antibody and a positive control using the anti-COMP 17-C10 mAb were included. FIG. 17C. The mAb 6-1A12 preferentially reacts against deamidated COMP peptide and not the native COMP sequence. Different concentrations of either the D-COMP Asp$_{64}$ TFLKD$_{64}$TVMEC (SEQ ID NO:3)-BSA construct or the native COMP Asn$_{64}$ TFLKN$_{64}$TVMEC (SEQ ID NO:4)-BSA construct were coated onto a 96 well plate in a direct ELISA with mAB 6-1A12, performed as for FIG. 17A, to test the affinity of the of the 6-1A12 antibody for both native and deamidated COMP. A standard curve with an appropriate dose response is generated for 6-1A12 and the deamidated COMP Asp$_{64}$-BSA construct; 6-1A12 did not recognize the native Asn$_{64}$-BSA construct.

FIG. 19A. Total COMP. FIG. 19B. D-COMP. FIG. 19C. Total COMP stratified by joint site. FIG. 19D. D-COMP stratified by joint site.

FIG. 20A demonstrates significant increase in D-COMP with hip OA severity and FIG. 20B demonstrates no significant change in D-COMP with knee OA severity. FIG. 20C demonstrates no significant change in Total COMP with OA hip severity while FIG. 20D demonstrates significant increase in Total COMP with knee OA severity. For each KL group (0-1,2,3,4+) n=48, 200, 99, 102 for hip OA and n=46, 199, 99, 102 for knee OA. Subjects were excluded when COMP was not quantifiable: 1 subject for D-COMP and 4 subjects for Total COMP. COMP purified from a cartilage extract was used as the standard for both the D-COMP and Total COMP ELISA's. Based upon earlier mass spectrometry of 50A cartilage extracts, a mean ratio of D-COMP:Total COMP of 1:105 was determined and used to correct the COMP standard to reflect the D-COMP levels. Significance was determined using a one-way Analysis of Variance (ANOVA) with a Bonferroni correction for multiple comparisons.

FIG. 22A—5-2G1, FIG. 22B—5-3D9 and FIG. 22C—6-1A10. D-COMP specific mAb: FIG. 22D—6-1A12, FIG. 22E—6-1B4, FIG. 22F—6-3B5 and FIG. 22G—6-1H3.

FIG. 24. Additional screening of the 006 mAbs for binding to the Duke006A and B peptides.

DETAILED DESCRIPTION OF THE INVENTION

Figure 1:
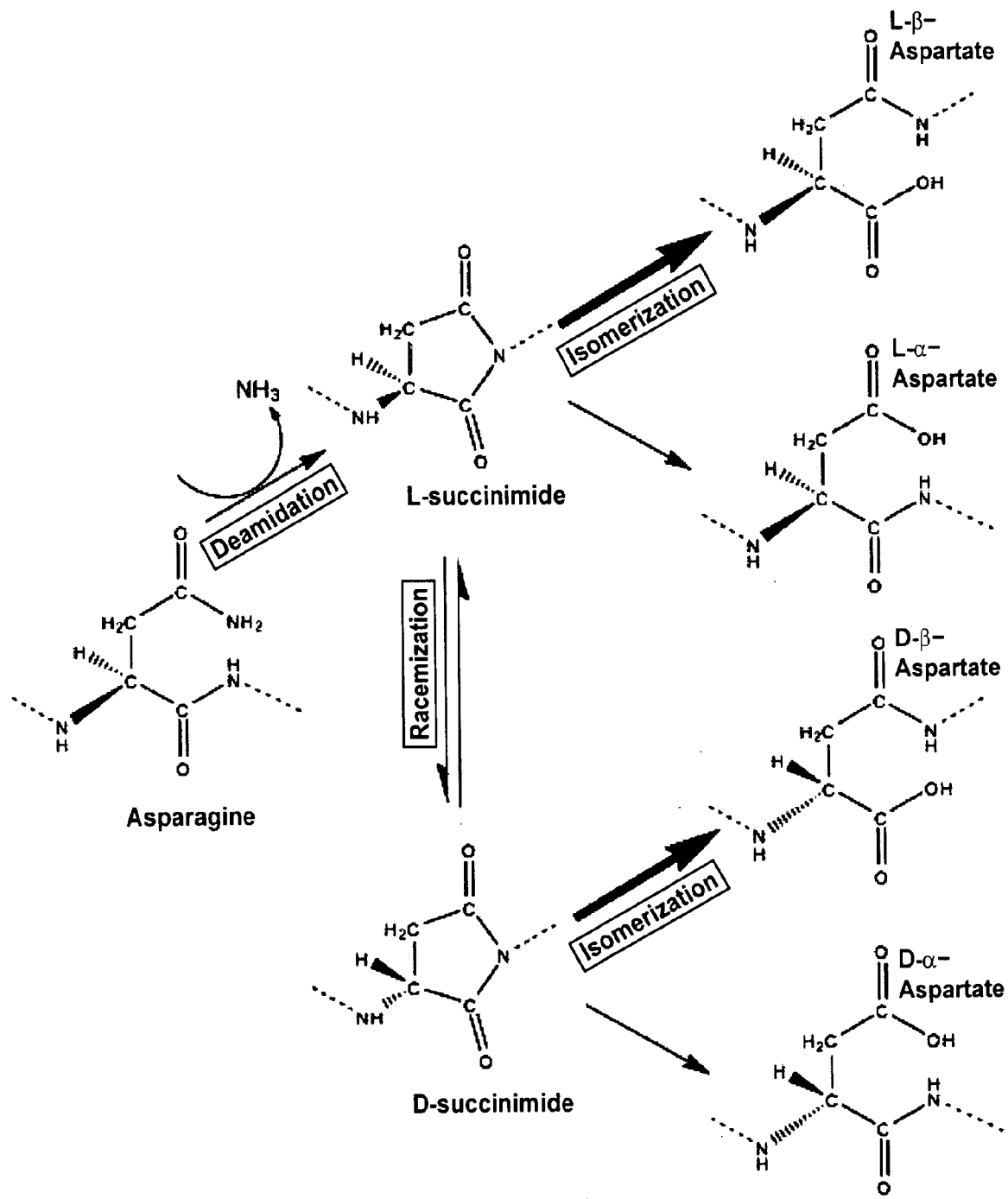
FIG. 1. Deamidation of peptide bonded Asn residues. Deamidation of Asn can lead to formation of a succinimide intermediate. The succinimide ring is unstable and highly susceptible to racemization and isomerization resulting in L-α-Asp, L-β-Asp, D-α-Asp, or D-β-Asp.
Figure 2:
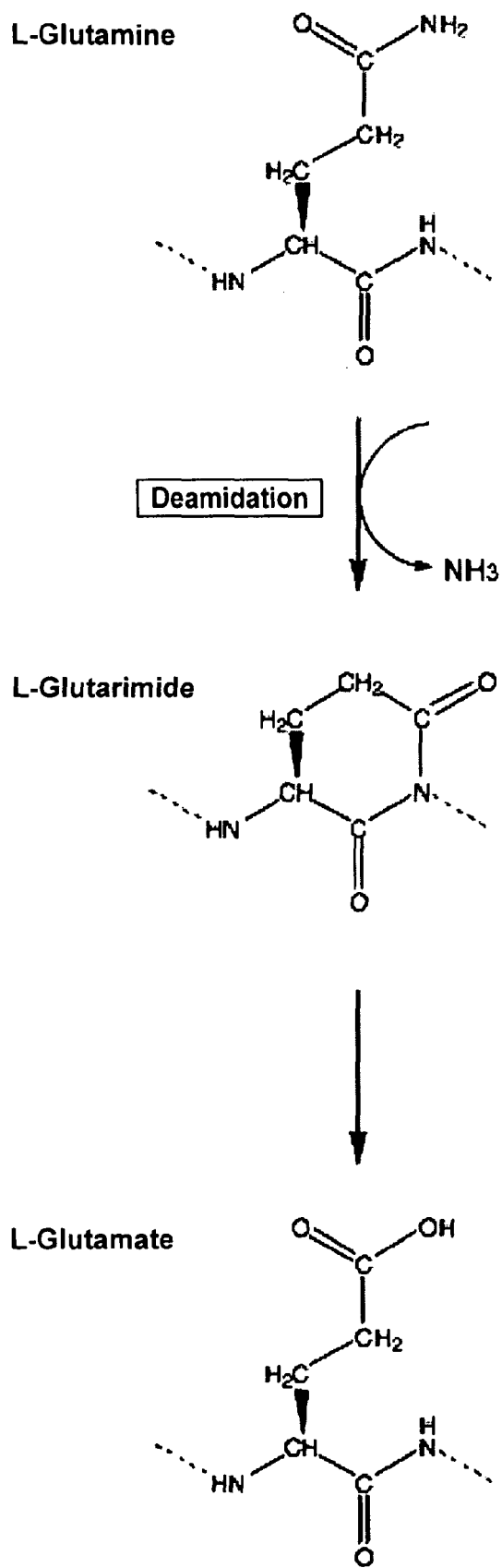
FIG. 2. Deamidation of Gln. Loss of the amine group from Gln resulting from cyclization of the structure. The intermediate glutarimide ring is unstable and readily hydrolyzes into Glu.

The present invention relates to biomarkers of musculoskeletal disease. The invention includes methods of quantifying non-enzymatically deamidated musculoskeletal protein fragments (biomarkers) in body fluids, tissue extracts, or histological sections. The presence of such deamidated biomarkers can serve as an index of musculoskeletal disease. A high concentration of deamidated biomarkers or ratio of deamidated to native or total biomarkers in, for example, a body fluid, or an increase in the concentration of deamidated biomarker (or ratio) over time, can indicate musculoskeletal disease associated with joint destruction and a high risk of disease progression. Conversely, a high concentration of the unmodified form can indicate high turnover of a joint with an ongoing repair response in an attempt to slow, halt or reverse the joint destructive process. Similarly, a decrease in the concentration of the deamidated biomarker over time, or little or no increase, can indicate tissue repair, or a low risk of disease progression.

The invention results, at least in part, from the identification of musculoskeletal protein sequences that have ASP and/ or GLU (referred to herein as deamidated) substituted for the native ASN and/or GLN residues (referred to herein as amidated or native), respectively, as a result of non-enzymatic deamidation. Joint tissue protein fragments in, for example, body fluids that contain such changes are, of necessity, derived from old, degraded tissue. Certain specific sequences within cartilage oligomeric matrix protein (COMP) have been determined, based on crystal structure data, to be subject to deamidation (see Example 2; see Table 2). Antibodies to the total (recognize native (amidated plus deamidated) and deamidated forms of these sequences have been developed (see Examples that follow). Such antibodies have been used to assay for the concentration in a body fluid of protein fragments containing the total amidated plus deamidated) sequence, and the concentration of protein fragments containing the non-native (non-enzymatically deamidated) sequence (see Examples below).

The data provided in the Examples that follow demonstrate that the presence of deamidated COMP (referred to herein as dCOMP, d-COMP, DCOMP or D-COMP) or protein fragments in body fluids or tissue extracts can serve as an index of hip disease. An elevated concentration of D-COMP or ratio of D-COMP to native or total COMP in, for example, a body fluid can indicate musculoskeletal disease associated with hip joint destruction. Conversely, elevated concentration of the total or native unmodified form (non-deamidated COMP or nCOMP) indicates a joint destructive process of the knee. The data provided in FIGS. 16 and 20, for example, show the incremental increases in d-COMP that occur with increasing severity of hip OA, and the incremental increases in t-COMP (Total COMP) that occur with increasing severity of knee OA.

While the invention is described in detail with reference to non-enzymatic deamidation, the invention encompasses quantification of other posttranslational modifications that can occur simultaneously with deamidation, including racemization, isomerization, citrullinization, dephosphorylation, nitration, glycation, and/or oxidation. The invention is described in detail with reference to musculoskeletal diseases/disorders, however, the invention also has application in neurodegenerative diseases/disorders (e.g., multiple sclerosis) and muscular dystrophies.

The present invention provides methods of diagnosing, monitoring or prognosing musculoskeletal diseases (e.g., OA, Calve Legg Perthes disease, hip dysplasias, other joint dysplasias, spinal disorders, rheumatoid arthritis and other inflammatory arthropathies, including psoriatic arthritis, ankylosing spondylitis, Reiter's syndrome, severity of joint injury or trauma, gout, pseudogout, osteoporosis and sarcopenia). A preferred embodiment of this aspect of the invention relates to a method of detecting hip osteonecrosis or the development of hip osteonecrosis. The invention also provides methods of monitoring therapies for such diseases/ disorders. A preferred embodiment of this aspect relates to a method of detecting or serially monitoring hip OA severity, for example, during the course of a hip OA clinical trial. The methods of the invention are applicable to a variety of settings in which prognostic value is provided by differentiating in vivo degenerative processes from repair responses.

The instant methods are designed to determine the amount (concentration) of non-enzymatically deamidated musculoskeletal protein fragments (e.g., epitopes) in a body fluid or tissue sample (or histological section or tissue extract). As pointed out above, deamidation results in the conversion of ASN to ASP and of GLN to GLU. Deamidated fragments detected and/or quantified in accordance with the invention can be derived from joint tissue proteins including, but not limited to, COMP, cartilage intermediate layer protein (CILP) Type I-XXVI collagen (inclusive) (preferably, Types I, II or IV), aggrecan or link protein, as well as from other proteins found in connective tissue. In certain preferred embodiments, deamidated musculoskeletal protein fragments are determined in a body fluid, such as whole blood, plasma, serum, urine, synovial fluid, or cerebral spinal fluid, or in a tissue extract.

In one embodiment, the present invention relates to a method of determining the absolute amount or the proportion of the total amount of musculoskeletal protein or protein fragments present in a sample (e.g., a body fluid or tissue sample) from a subject (e.g., a human or non-human mammal) that is derived from turnover or degradation of an aged musculoskeletal protein. The method comprises:
  i) determining the total (native amidated plus deamidated) amount of musculoskeletal protein or protein fragments, or native (amidated) comprising a sequence subject to non-enzymatic deamidation, present in the sample,
  ii) determining the amount that is deamidated or the proportion of that total amount that is deamidated (that is, that contains ASP or GLU residues at positions normally occupied by ASN or GLN, respectively), and
  thereby determining the amount or proportion of the total amount of such protein or protein fragments that is derived from turnover or degradation of aged (and, therefore, deamidated) musculoskeletal protein.

This method can be used, for example, to determine the relative amount of turnover of young and aged musculoskeletal protein in a subject. In addition, because deamidation can occur at 'hotspots' as a consequence of certain pathological conditions, this method can be used, for example, to identify sites of protein aging due to musculoskeletal pathology or disease.

In a preferred embodiment, the present invention relates to a method of diagnosing a musculoskeletal disease/disorder (e.g., a hip disease or disorder) in a test subject (e.g., a human or non-human mammal), comprising:
  i) obtaining a body fluid sample from the test subject that comprises musculoskeletal protein or protein fragments, which protein or protein fragments comprise a sequence that is subject to non-enzymatic deamidation as the musculoskeletal protein ages or is exposed to pathologic conditions that accelerate non-enzymatic deamidation,
  ii) determining the amount of such protein or protein fragments that comprise a deamidated form of the sequence, and
  iii) comparing the amount of deamidated sequence-containing protein or protein fragments resulting from step (ii) with a control (e.g., the amount in a sample from an age-matched (e.g., within 10 years) subject(s) without musculoskeletal disease), wherein an increased amount of deamidated sequence-containing protein or protein fragments in the sample from the test subject relative to the control indicates that the test subject has a musculoskeletal disease/disorder. Alternatively, step (iii) can comprise comparing the ratio of the amount of deamidated sequence-containing protein or protein fragments resulting from step (ii) to the total amount of protein or protein fragments (native plus deamidated) or to the amount of native protein or protein fragment with the ratio in a control, wherein a higher ratio in the sample from the test subject relative to the control indicates that the test subject has a musculoskeletal disease/disorder.

In another preferred embodiment, the present invention relates to a method of identifying a test subject (e.g., a human or non-human mammal) at risk of developing a musculoskeletal disease/disorder (e.g., a hip disease or disorder). The method comprises:
  i) obtaining a body fluid sample from the test subject that comprises musculoskeletal protein or protein fragments, which protein or protein fragments comprise a sequence that is subject to non-enzymatic deamidation as the musculoskeletal protein ages or is exposed to pathologic conditions that accelerate non-enzymatic deamidation,
  ii) determining the amount of such protein or protein fragments that comprise a deamidated form of the sequence, and
  iii) comparing the amount of deamidated sequence-containing protein or protein fragments resulting from step (ii) with a control (e.g., age-matched subject(s) without musculoskeletal disease), wherein an increased amount of deamidated sequence-containing protein or protein fragments in the sample from the test subject relative to the control indicates that the test subject is at risk of developing a musculoskeletal disease/disorder. Alternatively, step (iii) can comprise comparing the ratio of the amount of deamidated sequence-containing protein or protein fragments resulting from step (ii) to the total or native protein or protein fragment with the ratio in a control, wherein a higher ratio in the sample from the test subject relative to the control indicates that the test subject is at risk of developing a musculoskeletal disease/disorder.

In a further preferred embodiment, the present invention relates to a method of monitoring the efficacy of a musculoskeletal disease/disorder (e.g., a hip disease or disorder) therapeutic agent in a test subject. (e.g., a human or non-human mammal) The method comprises:
  i) obtaining a body fluid sample from the test subject that comprises musculoskeletal protein or protein fragments, which protein or protein fragments comprise a sequence that is subject to non-enzymatic deamidation as the musculoskeletal protein ages or is exposed to pathologic conditions that accelerate non-enzymatic deamidation, wherein the sample is obtained in the course of (or subsequent to) administration of the therapeutic agent to the test subject,
  ii) determining the amount of such protein or protein fragments that comprise a deamidated form of the sequence, and
  iii) comparing the amount of deamidated sequence-containing protein or protein fragments resulting from step (ii) with a control (e.g., a sample from the test subject prior to administration of the therapeutic or a sample from a subject(s) with musculoskeletal disease administered an alternative, therapy or placebo), wherein no increase or a decrease in the amount of deamidated sequence-containing protein or protein fragments in the sample from the test subject relative to the control indicates that the therapeutic agent is efficacious. Alternatively, step (iii) can comprise comparing the ratio of deamidated sequence-containing protein or protein fragments resulting from step (ii) to the native or total amount of fragment with the ratio in a control (e.g., a sample from the test subject prior to administration of the therapeutic or sample from a subject administered an alternate therapy or placebo), wherein no increase or a decrease in the ratio in the sample from the test subject relative to the control indicates that the therapeutic agent is efficacious.

It will be appreciated that therapeutic efficacy can be assessed over time during the treatment regimen.

In a further preferred embodiment, the present invention relates to a method of diagnosing hip disease/disorder in a test subject (e.g., a human or non-human mammal), comprising:
  i) obtaining a body fluid sample from the test subject that comprises musculoskeletal protein or protein fragments, which protein or protein fragments comprise a sequence that is subject to non-enzymatic deamidation as the musculoskeletal protein ages or is exposed to pathologic conditions that accelerate non-enzymatic deamidation,
  ii) determining the amount of such protein or protein fragments that comprise a deamidated form of the sequence, and
  iii) comparing the amount of deamidated sequence containing protein or protein fragments resulting from step (ii) with a baseline value for the test subject, wherein an increased amount of deamidated sequence containing protein or protein fragments in the sample relative to the baseline indicates that the test subject has hip disease/disorder. (See Examples that follow)

Alternatively, step (iii) can comprise comparing the amount or the ratio of the amount of deamidated sequence-containing protein or protein fragments resulting from step (ii) to the total or native protein or protein fragment and comparing the amount of the ratio for a test subject relative to the subject's baseline amount or ratio.

This approach makes it possible to distinguish old from young or recently synthesized proteins or protein fragments. Given that it is possible to quantify amounts of old (deamidated), young (non-deamidated or total minus deamidated) and total (combination of deamidated and non-deamidated) molecules, it is, therefore, possible to gain insights into tissue repair knowing the absolute and relative amounts of these forms of a protein or protein fragment. A scenario may exist, for example, in which the amount of deamidated (or ratio of the deamidated to total or native form) in a body fluid is reduced relative to an age-matched control or a subject's prior baseline sample, indicating reduction of tissue degradation or increased synthesis or tissue repair response. Conversely, an increase in native protein or protein fragment relative to the deamidated form might also suggest an anabolic or repair activity. Such a result might be observed early in a joint or other disease process.

Levels of deamidated musculoskeletal proteins or protein fragments present in a sample can be determined using methods well known in the art, and as described in the Examples below, such as HPLC, immunoassay, mass spectrometry and immunohistochemistry. In the methods of diagnosing and/or identifying a subject at risk and/or assessing therapeutic efficacy as described herein, the amount of deamidated sequence-containing protein or protein fragments measured can be an absolute amount or it can be a proportion of a total amount in the sample. Values determined according to the methods of this invention to be relevant include: difference in an absolute amount or in a proportion of a total amount comparing individuals with a musculoskeletal disease; difference in an absolute amount or in a proportion of a total amount over time comparing individuals with their baseline value; absolute amount or proportion of a total amount for an individual compared with historic age-matched controls and/or individuals with musculoskeletal disease for purposes of categorizing the unknown individual's status or to determine risk or occurrence of a musculoskeletal disease.

The present invention is primarily concerned with the diagnosis, monitoring and prognosis, etc. of human subjects or biological samples therefrom, but the invention can also be carried out on non-human animal subjects or biological samples therefrom, particularly non-human mammalian subjects such as mice, rats, guinea pigs, dogs, cats, sheep, goats, livestock and horses for veterinary purposes, and for drug screening and drug development purposes.

In yet another embodiment, the present invention relates to antibodies, such as polyclonal or monoclonal antibodies, (or antigen binding fragments thereof (e.g., Fab, F(ab')$_2$, Fv or single chain Fv fragments) that specifically recognize and bind epitopes in musculoskeletal proteins that undergo non-enzymatic deamidation as the protein ages. The invention includes antibodies (or antigen-binding fragments thereof) that recognize and bind deamidated epitopes specifically, native (non-deamidated) epitopes specifically, and antibodies that recognize and bind total epitope, i.e., both deamidated and non-deamidated forms. Examples of sequences within COMP that are recognized by antibodies of the invention (in deamidated, and/or native non-deamidated form) are as follows:

```
                                            SEQ ID NO: 1
(deamidated)
ELQETDAALQ SEQ ID NO: 2
(native)
ELQETNAALQ SEQ ID NO: 3
(deamidated)
TFLKDTVMEC SEQ ID NO: 4
(native)
TFLKNTVMEC SEQ ID NO: 5
(deamidated residue shown in brackets and native
residue in parenthesis in context of full length
COMP)
MVPDTACVLL LTLAALGASG QGQSPLGSDL GPQMLRELQE

T[D]/(N)AALQDVRD WLRQQVREIT FLK[D]/(N)TVMECD

ACGMQQSVRT GLPSVRPLLH CAPGFCFPGV ACIQTESGGR

CGPCPAGFTG NGSHCTDVNE CNAHPCFPRV RCINTSPGFR

CEACPPGYSG PTHQGVGLAF AKANKQVCTD INECETGQHN

CVPNSVCINT RGSFQCGPCQ PGFVGDQASG CQRGAQRFCP

DGSPSECHEH ADCVLERDGS RSCVCRVGWA GNGILCGRDT

DLDGFPDEKL RCPEPQCRKD NCVTVPNSGQ EDVDRDGIGD

ACDPDADGDG VPNEKDNCPL VRNPDQRNTD EDKWGDACDN

CRSQKNDDQK DTDQDGRGDA CDDDIDGDRI RNQADNCPRV

PNSDQKDSDG DGIGDACDNC PQKSNPDQAD VDHDFVGDAC

DSDQDQDGDG HQDSRDNCPT VPNSAQEDSD HDGQGDACDD

DDDNDGVPDS RDNCRLVPNP GQEDADRDGV GDVCQDDFDA

DKVVDKIDVC PENAEVTLTD FRAFQTVVLD PEGDAQIDPN

WVVLNQGREI VQTMNSDPGL AVGYTAFNGV DFEGTFHVNT

VTDDDYAGFI FGYQDSSSFY VVMWKQMEQT YWQANPFRAV

-continued
AEPGIQLKAV KSSTGPGEQL RNALWHTGDT ESQVRLLWKD

PRNVGWKDKK SYRWFLQHRP QVGYIRVRFY EGPELVADSN

VVLDTTMRGG RLGVFCFSQE NIIWANLRYR CNDTIPEDYE

THQLRQA.
```

Antibodies to deaminated (SEQ ID NOs:1 and 3) forms of COMP and/or native (SEQ NOs:2 and 4) forms of COMP are described in Examples below.

Figure 23:
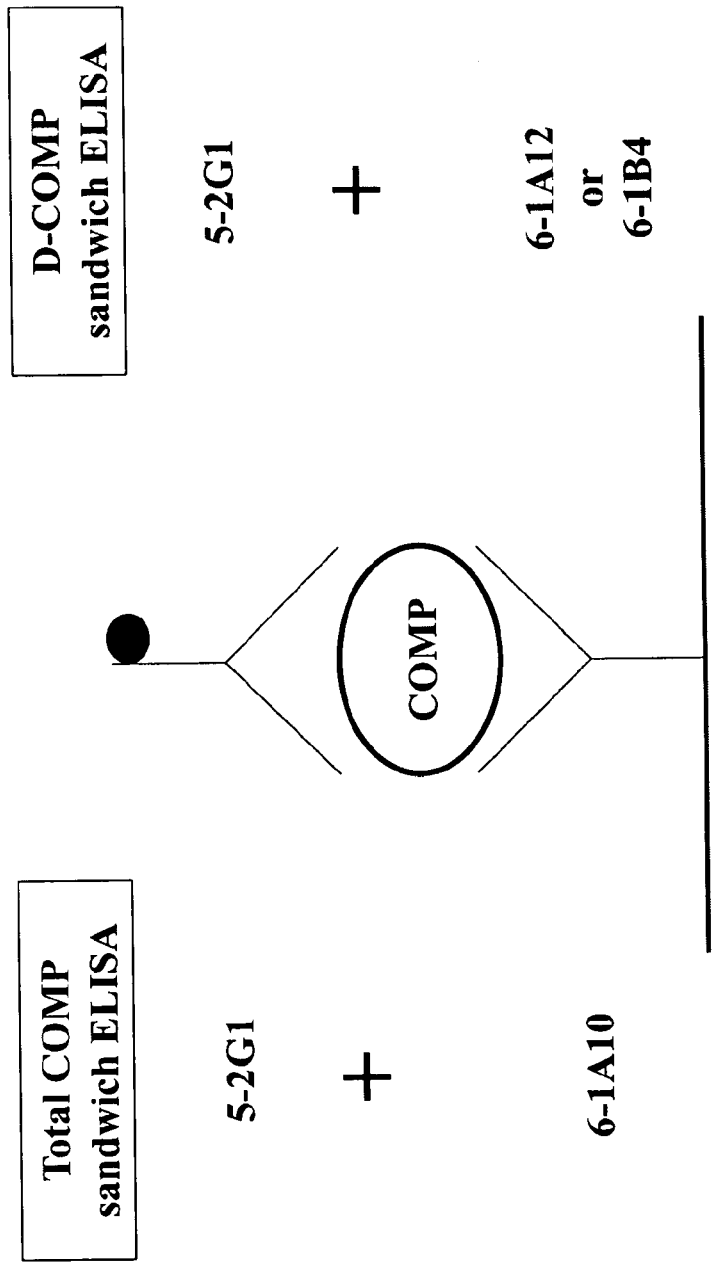
FIG. 23. Schematic of exemplary D-COMP assay.

Further embodiments of the present invention relate to immunoassays that involve the use of such antibodies (or antigen-binding fragments thereof), such as, for example, enzyme-linked immunosorbent assays (ELISA), immunoprecipitation assays, immunohistochemical assays, enzyme immunoassays (EIA), agglutination assays, precipitation/flocculation assays, immunoblots (Western blot; dot/slot blot, etc.), radioimmunoassays (RIA), immunodiffusion assays, immunofluorescence assays (e.g., FACS); chemiluminescence assays, antibody library screens, expression arrays, etc., for diagnosis of, prognosis of and/or screening for musculoskeletal diseases/disorders. ELISA-type assays suitable for diagnosing, prognosing and/or screening for musculoskeletal diseases/disorders are described in the Examples below. The methods described in Examples 4 and 6 and FIG. 23 are preferred, although, in further embodiments, additional antibody pairs for sandwich ELISA are possible including the following: antibodies:

D-COMP specific: 6-1B4, 6-3B10, 6-3B5, 6-1H3, 6-3A5, 6-1A12, -6-1A4, 6-1F9, 6-1A8, 6-1A6, 6-1F8, 6-1H1, 6-1C12 (these are preferred as capture antibodies for the D-COMP ELISA to increase the sensitivity of the ELISA for detecting these low abundance molecules);

Total COMP (detect total COMP fragments including native amidated and deamidated forms): 5-1E4, 5-3C2, 5-3D4, 5-3B4, 5-3F9, 5-3D9, 5-2G1, 6-1A10, 6-3B3, 6-3B1, 6-1H2, 6-1G7, 6-1H12, 6-1H7, 6-2A9, 6-3A1 (these are preferred as detection antibodies for the D-COMP ELISA and any two of these can be used in combination for a Total COMP ELISA)

In a further embodiment, the present invention relates to kits for diagnosing, prognosing, and/or screening for the diseases/disorders described herein. The kits can contain reagents for diagnosing, prognosing, and/or screening for such diseases/disorders and printed instructions for use thereof, in a container or package. Such reagents can include monoclonal and/or polyclonal antibodies (or antigen binding fragments thereof) that bind deamidated and/or non-deamidated fragments of musculoskeletal proteins, control antigens, calibration antigens, secondary antibodies to detect antigen/antibody complex formation, detection reagents, buffers (e.g., Tris), diluents, slides, vessels, chambers, mixers, plates, vials, etc., as would be well known to one of ordinary skill in the art to conduct immunoassay protocols.

The following hybridomas were deposited with the American Type Culture Collection (ATCC) P.O. Box 1549, Manassas, Va. 20108, on Feb. 17, 2011 under the terms of the Budapest Treaty:

| Hybridoma | Accession No. |
| --- | --- |
| 5-2G1 | PTA-11684 |
| 5-3D9 | PTA-11685 |
| 6-1A10 | PTA-11689 |
| 6-1A12 | PTA-11688 |
| 6-1B4 | PTA-11690 |
| 6-1H3 | PTA-11687 |
| 6-3B5 | PTA-11686 |

Figure 22:
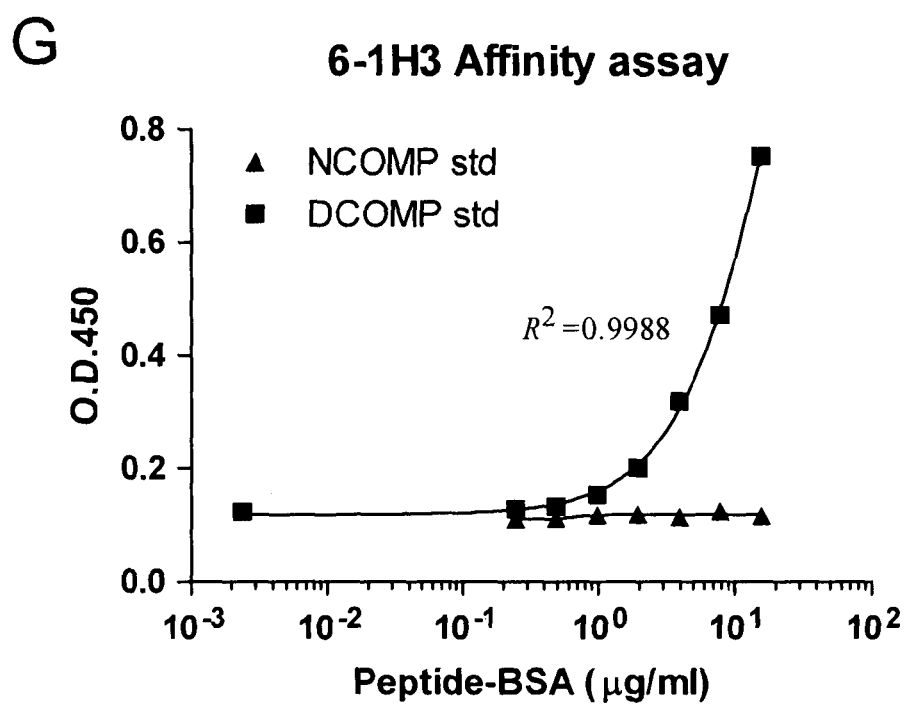
FIGS. 22A-22G. Specificity of antibodies. Total COMP mAb.

FIG. 22 shows the specificity of the antibodies produced by the above hybridomas (see also FIG. 23 for D-COMP assays).

Certain aspects of the invention can be described in greater detail in the non-limiting Examples that follow.

EXAMPLE 1

As described below, peptides have been identified within COMP that are predicted to undergo deamidation. Monoclonal antibodies recognizing the deamidated forms have been developed and their specificity for biomarker studies validated. In the course of this work, a method of aging native COMP peptides to induce deamidation, verified by HPLC analysis, has been developed.

Figure 3:
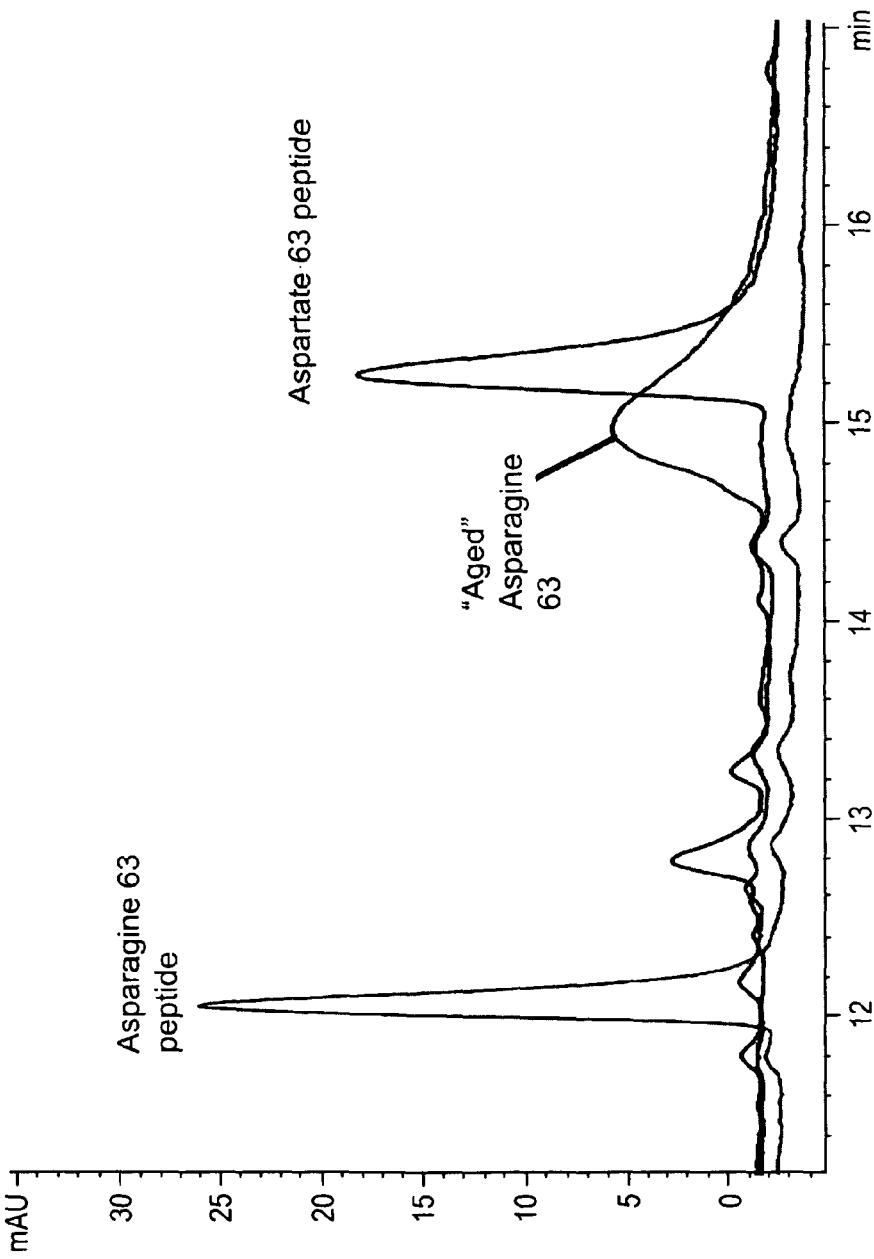
FIG. 3. In vitro deamidation of COMP peptides.
Figure 4:
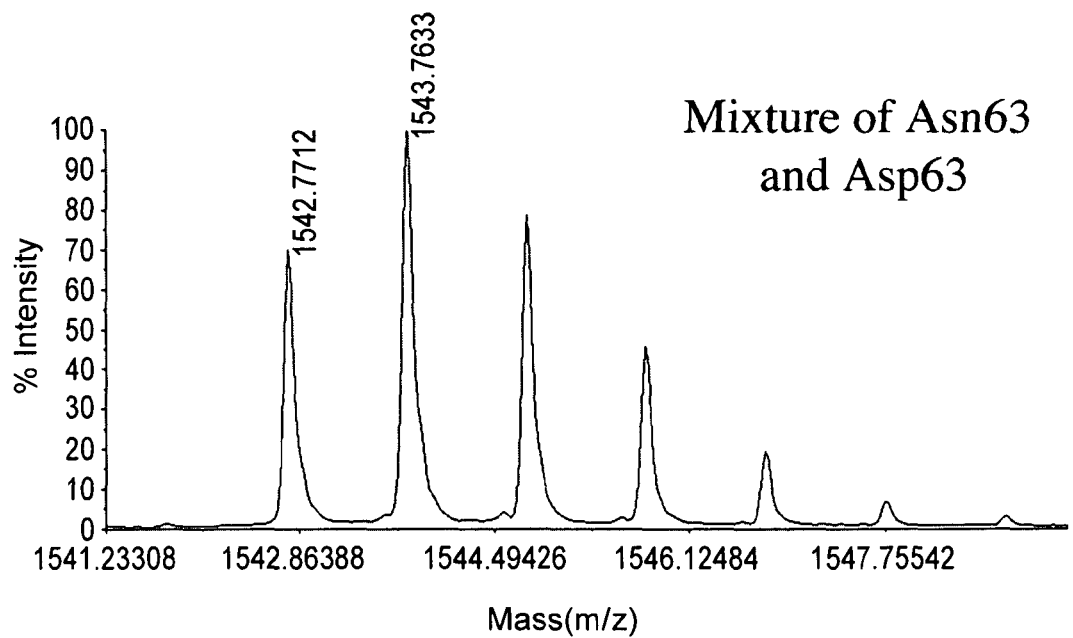

The native Asn containing COMP (DUK006A) peptide (see Example 2) was incubated at room temperature for 72 hours leading to a rightward shift in the HPLC trace resulting in its overlap with the migration of the corresponding deamidated COMP peptide (FIG. 3). It is possible to differentiate the native (FIG. 4A) and deamidated (FIG. 4B) epitopes by mass spectroscopy and the presence of both in a mixture (FIG. 4C) (Doyle et al, Ann. N.Y. Acad. Sci. 1050:1-9 (2005)). A similar procedure can be used for identifying hot spots of deamidation in purified fragments of cartilage ECM proteins.

EXAMPLE 2

Described below is the development and validation of monoclonal antibodies to deamidated and/or native residues in COMP. Antibodies described are suitable for use in the detection of biomarkers.

Putative deamidation hotspots within COMP were determined using an algorithm developed by Robinson and Robinson (Molecular Clocks: Deamidation of Asparaginyl and Glutaminyl Residues in Peptides and Proteins, Cave Junction, OR, Althouse Press (2004); found at URL[dot]deamidation[dot]org). This algorithm uses an investigator inputted crystal structure and amino acid composition of a protein to predict Asn residues susceptible to deamidation. The COMP protein structure files were retrieved from URL[dot]rcsb[dot]org in the form of the PDB files: 1fbm.pdb and 1vdf.pdb. Both files are for Rattus norvegicus COMP as the crystal structure for human COMP was not available. Using the rat sequence and structure, two different predicted hotspots were identified, $Asn_{41}$ and $Asn_{63}$. These sites correspond to $Asn_{42}$ and $Asn_{64}$ in the human COMP sequence. The prediction parameters for sequence file 1vdf.pdf are shown in Table 1 (the 1fbm.pdb crystal structure also predicted deamidation of the same Asn residues).

TABLE 1

Putative deamidation hotspots as predicted by the Robinson and Robinson algorithm. Results shown are for the 1 vdf.pdb crystal structure.

| PDB Identifier: | IVDF | PDB Identifier | 1VDF |
|---|---|---|---|
| Sequence: | ALYS-ASN63-THR | Sequence: | A THR-ASN41-ALA |
| CD: | 182.544774 | CD: | 97.278331 |
| ID | 63 460274 | ID: | 63 460274 |
| S1 - Helix NH2: | 0.0 | S1 - Helix NH2: | 0.0 |
| S2 - Helix COOH: | 0.0 | S2 - Helix COOH: | 0.0 |
| S3 - Helix Center: | 1.0 | S3 - Helix Center: | 1.0 |
| S4 - Antiparallel Residues: | 0.0 | S4 - Antiparallel Residues: | 0.0 |
| S5 - Antiparallel HBonds: | 1.0 | S5 - Antiparallel HBonds: | 1.0 |
| S6 - CO Hydrogen Bonds: | 0.0 | S6 - CO Hydrogen Bonds: | 1.0 |
| S7 - NH2 Hydrogen Bonds: | 1.0 | S7 - NH2 Hydrogen Bonds: | 2.0 |
| S8 - NH Hydrogen Bonds: | 1.0 | S8 - NH Hydrogen Bonds: | 1.0 |
| S9 - Other Hydrogen Bonds: | 1.0 | S9 - Other Hydrogen Bonds: | 1.0 |
| S10 - End of Chain Parameter: | 0.0 | S10 - End of Chain Parameter: | 0.0 |
| S11 -Fixed Structure on NH2 side: | 5.0 | S11 - Fixed Structure on NH2 side: | 5.0 |
| S12 Fixed Structure on COOH side: | 5.0 | S12 Fixed Structure on COOH side: | 5.0 |
| Number of Amides in Protein: | 2 | Number of Amides in Protein: | 2 |
| Number of Residues in Protein: | 46 | Number of Residues in Protein: | 46 |

Using the protein sequences available in the NCBI database (URL:ncbi[dot]nlm[dot]nih[dot]gov), it was confirmed that the predicted Asn deamidation hotspots were contained in human COMP and conserved in the following animals: human, mouse, rat, horse, cow, chimpanzee, chicken, and dog, see Table 2. The homologous epitope containing with $Asn_{41}$ was also found in the available partial sequence for the Rhesus Monkey, Table 2.

TABLE 2

Conservation of the predicted Asn deamidation sites in COMP.
Table 2 discloses SEQ ID NOS 9-20, respectively, in order of appearance.

|  |  | Duke005 peptide sequence | Duke 006 peptide sequence |
|---|---|---|---|
| Homo sapien (human) | MVPDTACVLLLLTLAALGAS GQGQSPLGSDLGPQMLR | ELQETNAALQ DVRELLRQQVREI | TFLKNTVMEC DACG |
| Rattus norvegicus (rat) | MSP TACVLVLALAALRAT GQGQIPLGGDLAPQMLR | ELQETNAALQ DVRELLRQQVKEI | TFLKNTVMEC DACG |

TABLE 2-continued

Conservation of the predicted Asn deamidation sites in COMP.
Table 2 discloses SEQ ID NOS 9-20, respectively, in order of appearance.

| | | Duke005 peptide sequence | Duke 006 peptide sequence |
|---|---|---|---|
| Mus musculus (mouse) | MGP TACVIVLALAILRAT GQGQIPLGGDLAPQMLR | ELQETNAALQ | TFLKNTVMEC DACG |
| | | DVRELLRQQVKEI | |
| Canis lupus familiaris (dog) | MVPAAACVLLLTLAALGVS GQGQIPLGADLGPQMLR | ELQETNAALQ DVRELLRQQVKEI | TFLKNTVMEC DACG |
| Equus cabollus (horse) | MVLSAAPVLLLALAALVSS QGQ TPLGTELGPQMLR | ELQETNAALQ DVRELLRQQVKEI | TFLKNTVMEC DACG |
| Bos taurus (cattle) | MVLAAARVLLLTLAALGAS GQGQMPLGGDLGPQMLR | ELQETNAALQ DVRDLLRQQVKEI | TFLKNTVMEC DACG |
| Pan troglodytes (chimpanzee) | MVPDTACVLLLTLAALGAS GQGQSPLGSDLGPQMLR | ELQETNAALQ DVRELLRQQVREI | TFLKNTVMEC DACG |
| Sus scrofa (pig) | MVLTVARVLLITLAALGAS GQGQITLGADLGPQMLR | ELQETNAALQ DVRELLRQQVKEI | TFLKNTVMEC DACG |
| Gallus gallus (red jungle fowl) | MISALAFVFLLCLSCPFSSCQQRRA GIEVGPEMLE EMRETNRVLM | EVRDLLKQQIKEI | TFLKNTVMEC DACG |
| Ailuropoda melonoleuca (giant panda) | MVPATACVLLLTLAVLGAS GQGQISLGADLGPQMLR | ELQETNAALQ DVRELLRQQVKEI | TFLKNTVMEC DACG |
| Xenopus tropicalis (western clawed frog) | MLS VALLSSFCIFFGSCQQLSGRG DVGPQLLT EMKETNSVLR | EVRELLKRQIEEI | TFLKNTVMEC DACG |
| Monodelphis domestica (gray short-tailed opossum) | MPLSPSLGLLLLAFACHLVTGQRQAPVGGDVAPQMLR EMKETNLVLQ | EVRELLKQQIKEI | TFLKNTVMEC DACG |

Two peptides were generated based upon the $Asn_{41}$ hotspot and designated Duke005A and Duke005B. Duke005A was the native sequence found in COMP (ELQETN$_{41}$AALQ (SEQ ID NO:2)) and Duke005B was the equivalent sequence but with the Asn replaced with an Asp (ELQETD$_{41}$AALQ (SEQ ID NO:1)), mimicking the sequence after a deamidation event. To aid in coupling, a Cys was included at the N-terminus which is not found in the native sequence. Note that in human COMP, the numbering of this site is designated $Asn_{42}$.

Two further peptides were generated based upon the $Asn_{63}$ hotspot and designated Duke006A and Duke006B. Duke006A was the native sequence found in COMP (TFLKN$_{63}$TVMEC (SEQ ID NO:4)) and Duke006B was the equivalent sequence but with the Asn replaced with an Asp (TFLKD$_{63}$TVMEC (SEQ ID NO:3)), again mimicking the sequence after deamidation. The Cys found at the C terminus is part of the native COMP sequence. Note that in human COMP, the numbering of this site is designated $Asn_{64}$.

All peptides used for antibody production were synthesized by AnaSpec (Duke005B was obtained with an HPLC purity >70%; Duke006B was obtained with an HPLC purity >90%).

Figure 5:
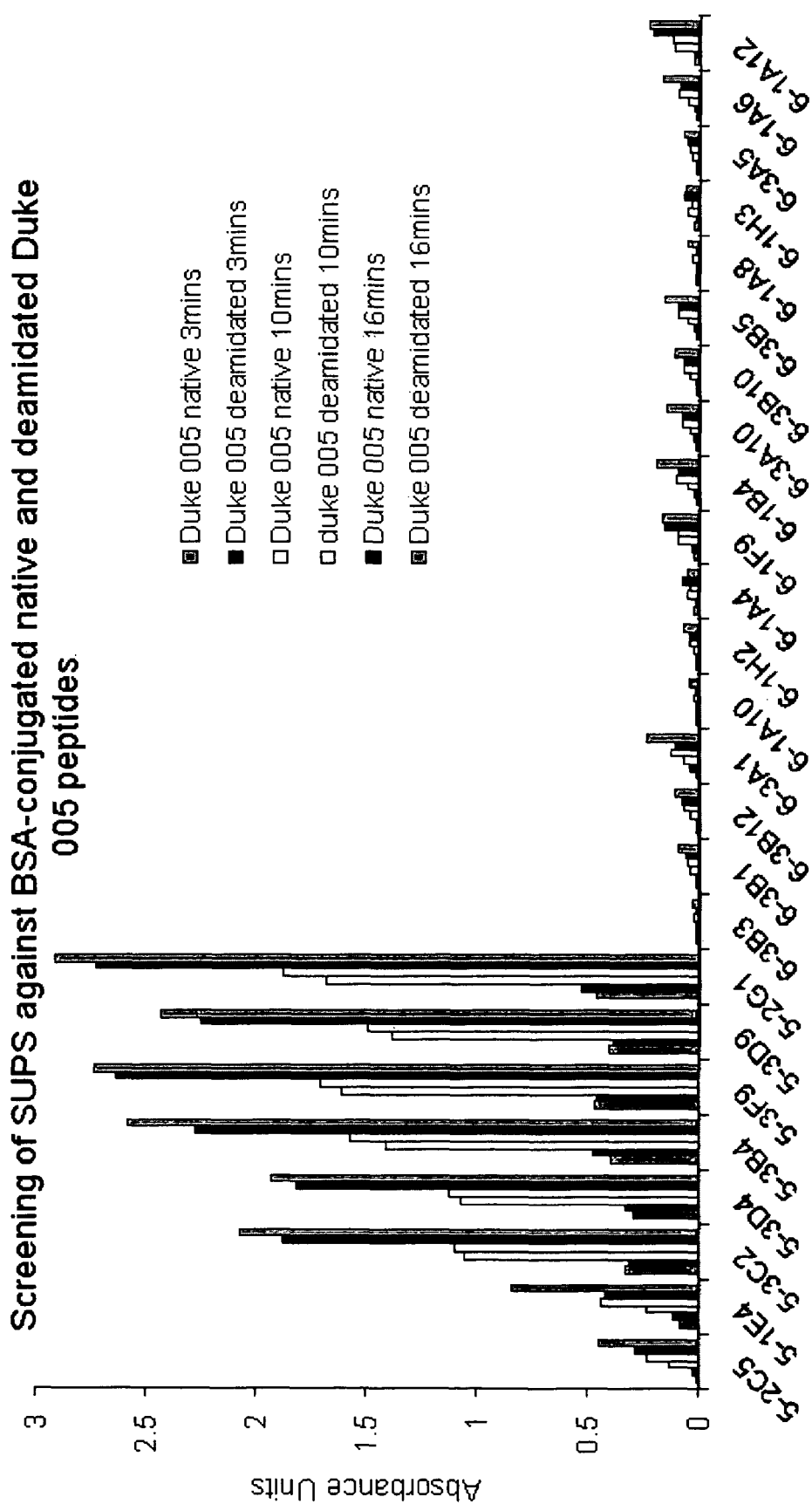
FIG. 5. Screening of hybridoma supernatants (SUPS) against BSA-conjugated native and deamidated Duke 005 peptides.
Figure 6:
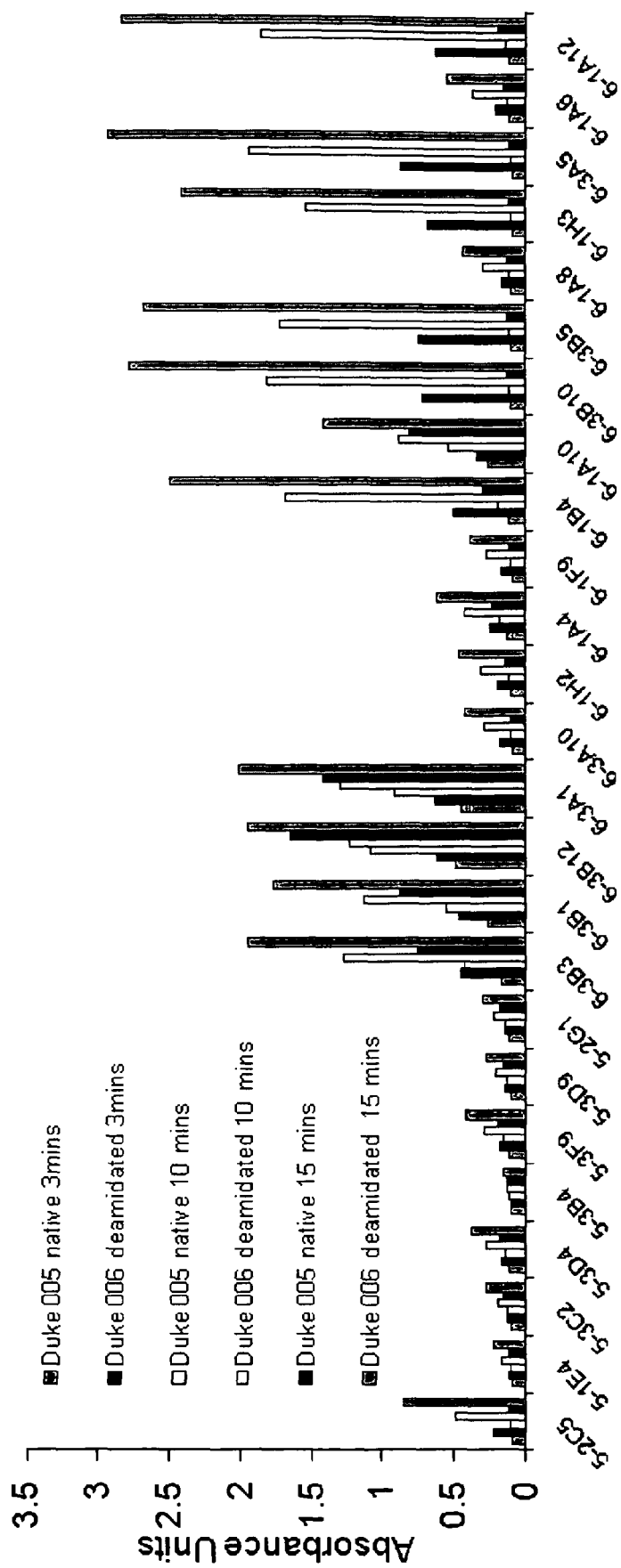
FIG. 6. Screening of hybridoma supernatants (SUPS) against BSA-conjugated native and deamidated Duke 006 peptides.

To generate antibodies to investigate the theoretical deamidated epitopes in COMP, the deamidated epitope peptides Duke005B and Duke006B were used as immunogens in standard protocols. It was hypothesized that this approach, using novel epitopes for immunization, would produce antibodies which not only recognized deamidated COMP but would also produce antibodies that recognized total COMP (amidated and deamidated forms) in a manner that was independent of deamidation state. FIGS. 5 and 6 show results of screening all 25 of the immunoreactive monoclonal antibodies (mAbs) produced as a result of immunizing mice with either the Duke005B or the Duke006B peptides. FIG. 5 shows results of screening all the mAbs for binding to the Duke005 A and B peptides and FIG. 6 shows the results of screening all the mAbs for binding to the Duke006 A and B peptides. FIG. 24 shows additional screening of the 006 mAbs for binding to the Duke006A and B peptides.

Four classes of monoclonal antibodies were identified through screening against all 4 peptides coupled to BSA in an ELISA format:

Antibodies that recognized total Duke005 epitope, ie bound both deamidated and native forms of COMP (seven different monoclonal antibodies: 5-1E4, 5-3C2, 5-3D4, 5-3B4, 5-3F9, 5-3D9, 5-2G1)

Antibodies that recognized total Duke006 epitope, ie bound both deamidated and native forms of COMP (nine monoclonal antibodies: 6-3B3, 6-3B1, 6-1A10, 6-1H2, 6-1G7, 6-1H12, 6-1H7, 6-2A9, 6-3A1)

Antibodies that recognized only deamidated Duke006 epitope, ie bound solely to the deamidated Duke006B epitope (thirteen monoclonal antibodies: 6-1B4, 6-3B10, 6-3B5, 6-1H3, 6-3A5, 6-1A12, 6-1A4, 6-1F9, 6-1A8, 6-1A6, 6-1F8, 6-1H1, 6-1C12).

An antibody that recognized both the Duke005 A and B peptides and the Duke006B (deamidated) peptide (one monoclonal antibody: 5-2C5).

No monoclonal antibodies specific for the deamidated Duke005 sequence were identified. All the mAbs to the Duke005 peptide recognized both the amidated and deamidated sequences. While antibodies were developed that recognized both the Duke006 deamidated and the native sequence, all of these antibodies showed a preference for the deamidated sequence.

Figure 7:
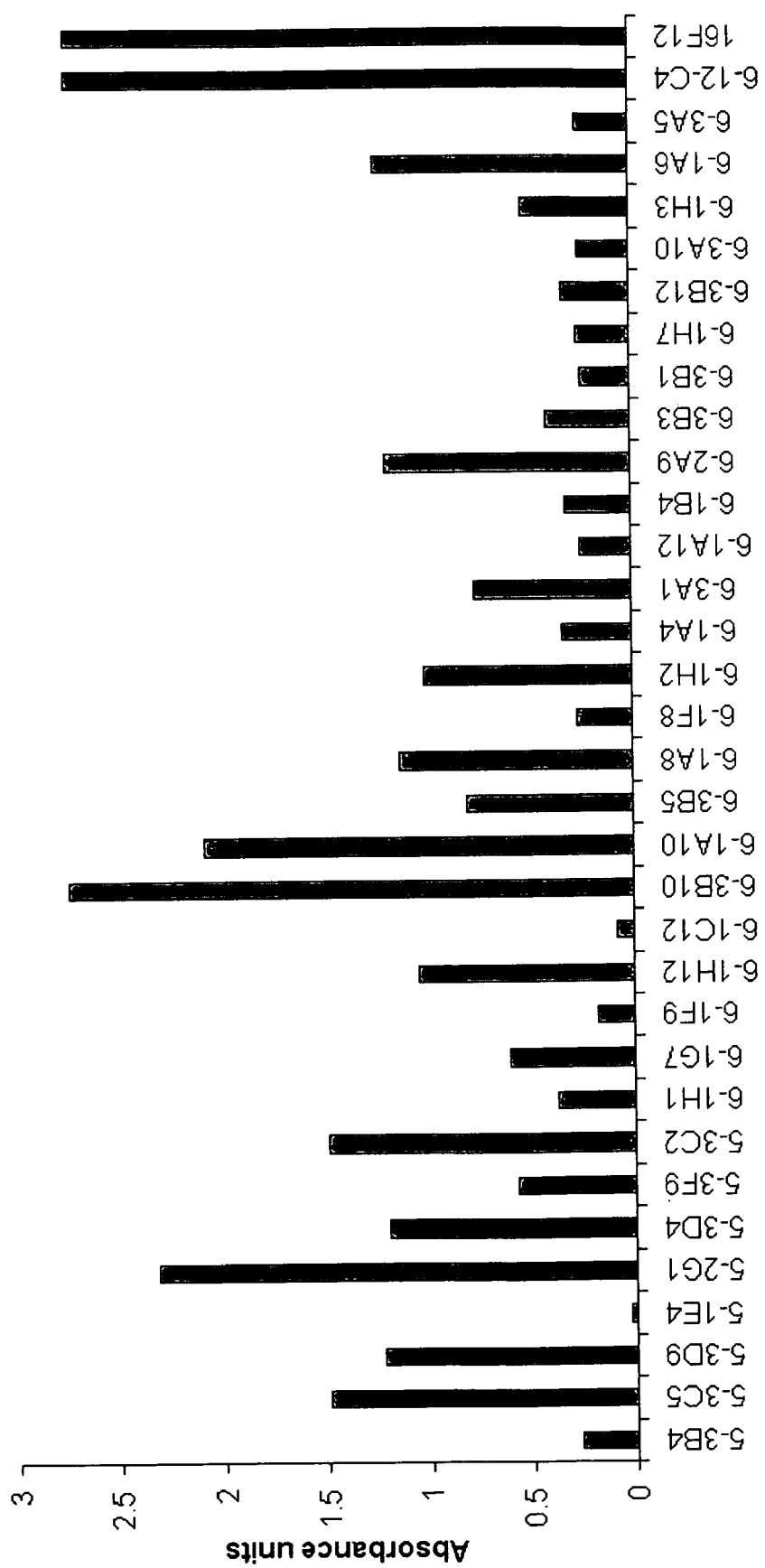
FIG. 7. All antibodies demonstrate some binding to human COMP after subtraction of blanks.

To confirm that the antibodies recognized COMP, an EDTA cartilage extract, which is enriched for human COMP, was coated onto ELISA plates. An ELISA was performed using the neat antibody supernatants. All of the antibodies showed some binding to human COMP after the subtraction of the blanks (FIG. 7).

Figure 8:
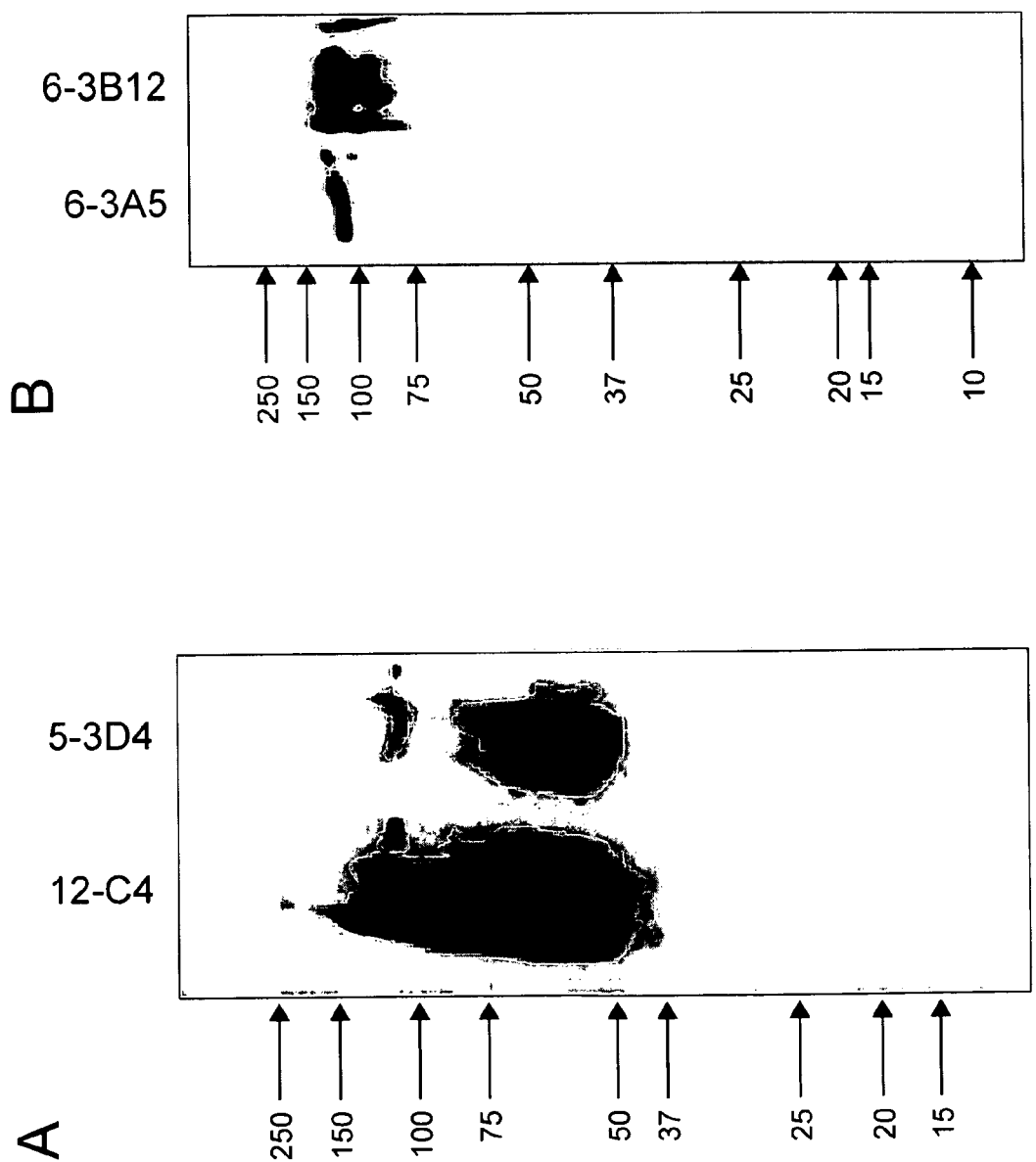
FIGS. 8A and 8B. Western blot analysis of monoclonal antibody binding to human COMP from an EDTA cartilage extract.

To further characterize the antibodies, Western blot analysis was performed on a subset of the antibodies: 5-3D4 (recognizing native and deamidated COMP-Duke005 epitope), 6-3A5 (specific for deamidated COMP-Duke006 epitope), 6-3B12 (specific for native and deamidated Duke006 epitope) (FIG. 8). The monoclonal antibody 12C4, to the carboxy-terminus of COMP, gift from Dr. Vladimir Vilim, was used as a positive control for native COMP protein detection (Vilim et al, Clin. Chim. Acta 328:59e69 (2003)). This blot confirmed the ability of these antibodies to recognize COMP specifically. Importantly, these results indicate that deamidated COMP, synonymous with non-enzymatically damaged COMP, exists in vivo.

Figure 9:
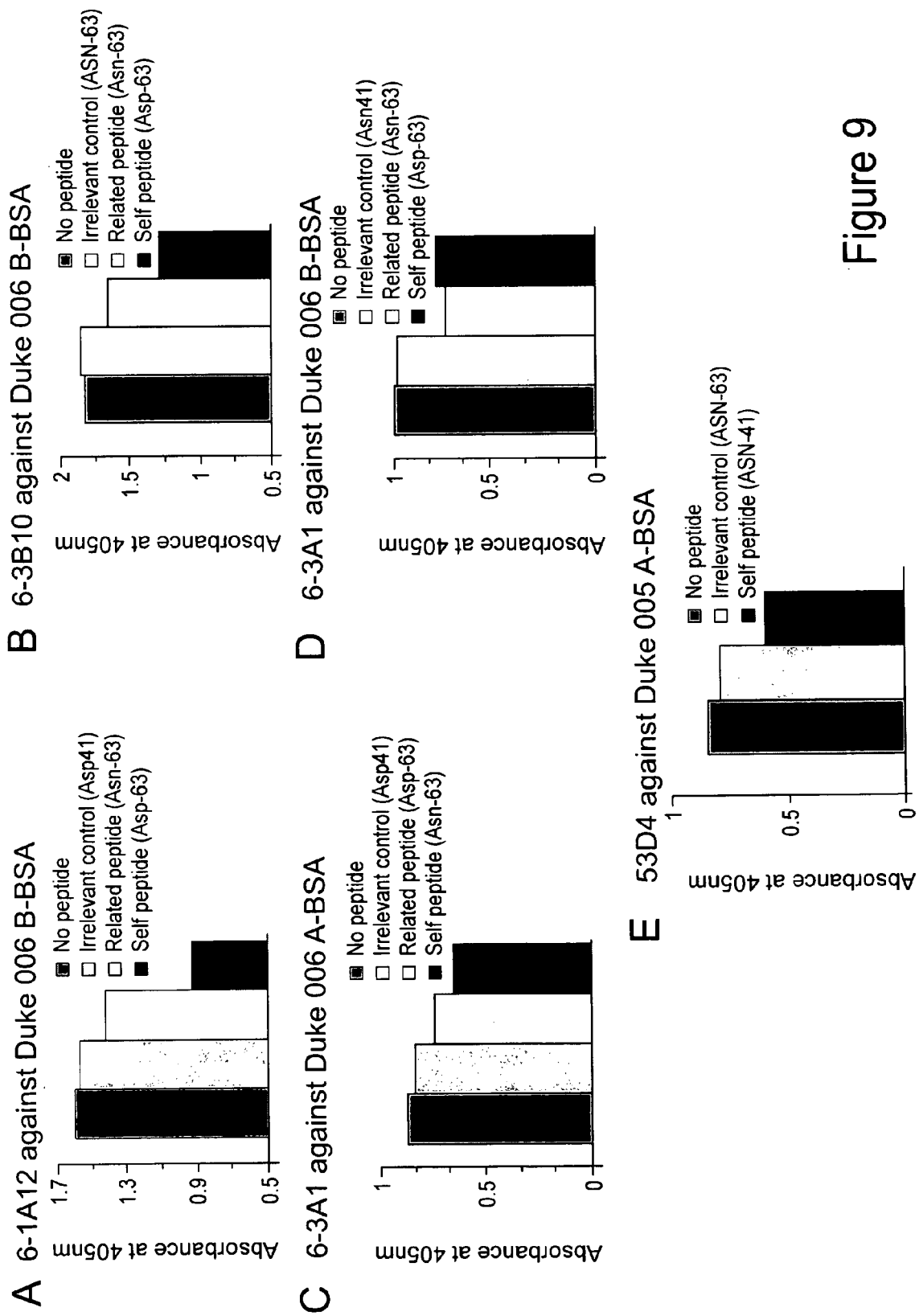

Using peptide competition, the binding properties of three of the Duke006 antibodies was confirmed. The Duke006-BSA conjugated peptide was coated to the plate; as competitors, four independently produced peptides which spanned the epitopes sites of Duke005 and Duke006 were used: Asn41 ([C]ELQETNAALQ) (SEQ ID NO:6), Asp41 ([C]ELQETDAALQ) (SEQ ID NO: 7), Asn63 (TFLKNTVMEC (SEQ ID NO:4)) and Asp63 (TFLKDTVMEC (SEQ ID NO:3)). The ability of peptide competitors to compete appropriately for binding, validated the epitope specificity of two mAbs specific for the deamidated sequence: 6-1 A12 (FIG. 9A) and 6-3B10 (FIG. 9B), and one mAb which recognized both amidated and deamidated sequences: 6-3A1 (FIGS. 9C-9D). Using the Duke005-BSA conjugated peptide, and the same competitors, a Duke005 raised antibody was confirmed as being specific for both the amidated and deamidated Duke005 sequences: 5-3D4 (FIG. 9E).

Summarizing, antibodies have been developed to two separate defined epitopes in COMP (Duke 005A and 006A) which are independent of deamidation state and can be used to characterize total COMP. Antibodies have also been developed that prefer or are specific for deamidated epitopes in COMP ((Duke 005B and 006B) that can be used to characterize degradation and repair state of a tissue containing COMP. These antibodies have utility in ELISA, immunoprecipitation, immunocapture, immunohistochemistry and Western blotting applications. These antibodies can be used to discriminate between 'young/new' COMP that is newly or recently synthesized and 'old/aged' COMP that has been incorporated in a matrix for a longer period of time. COMP is not just found in cartilage but there is now a growing body of evidence to suggest that it is also produced in other tissues, including the synovium (Hummel et al, Br. J. Rheumatol. 37(7):721-728 (1998), DiCesare et al, FEBS Lett. 412(1): 249-252 (1997)), arteries during atherosclerosis (Lutgens et al, Circulation 111(25):3443-3452 (2005)), during the healing phase of bone following joint arthroplasty (Sharif et al, Arthritis Rheum. 50(8):2479-2488 (2004)), in tendons (DiCesare et al, FEBS Lett. 354(2):237-240 (1994)), osteoblasts (DiCesare et al, Journal of Orthopaedic Research 18(5):713-720 (2000)). Orthopaedic Research 18(5):713-720 (2000)) and during growth and development (Blumbach, et al, Matrix Biol. 27(4): 306-18 (2008); Schmitz et al, Matrix Biol. 27(2): 67-85 (2008); Koelling et al, Arthritis Res. Ther. 8(3): R56 (2006)).

Under high turnover states, it is reasonable to assume that the COMP produced will be "new" and in the native confirmation. The antibodies described above can distinguish between 'young'/'new' COMP (native sequence) and older COMP (deamidated).

EXAMPLE 3

Example 2 details the development of antibodies that are specific for a predicted deamidated epitope in COMP. Their specificity and the ability to recognize COMP in cartilage extracts is shown by western blot. Two questions are addressed by the studies described below:

1. Can an ELISA for aged deamidated COMP be developed?

2. Can the epitope be detected in body fluids?

One of the biggest problems faced when developing ELISA protocols to the epitopes described herein was what to use as a standard. The age-related changes are likely to be only present in a small subset of the total proteins making the use of native proteins an unlikely source. Generation of recombinant proteins for each of the epitopes, however, would be both time consuming and expensive.

Figure 10A:
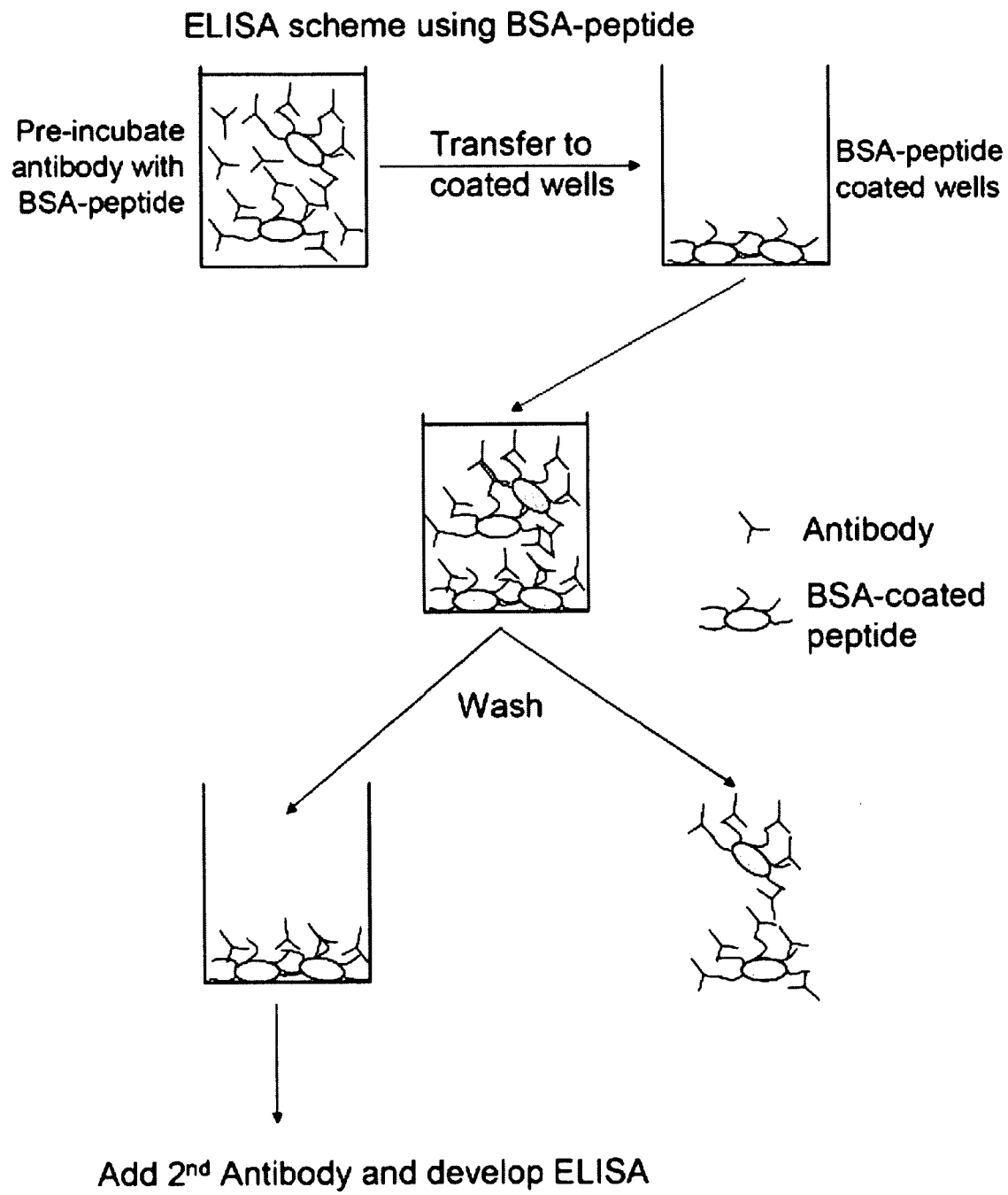
FIGS. 10A and 10B.
Figure 10B:
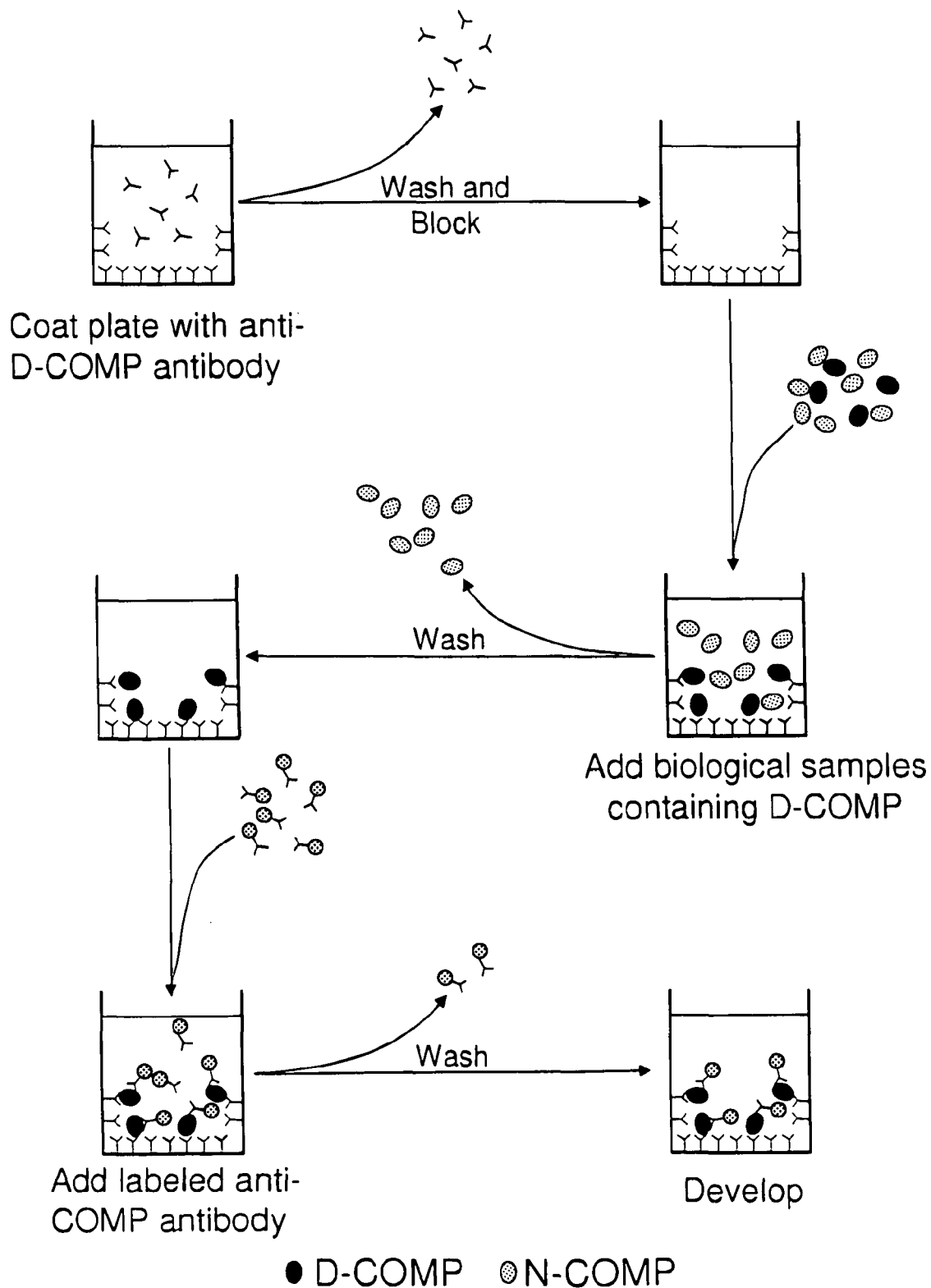
Figure 11A:
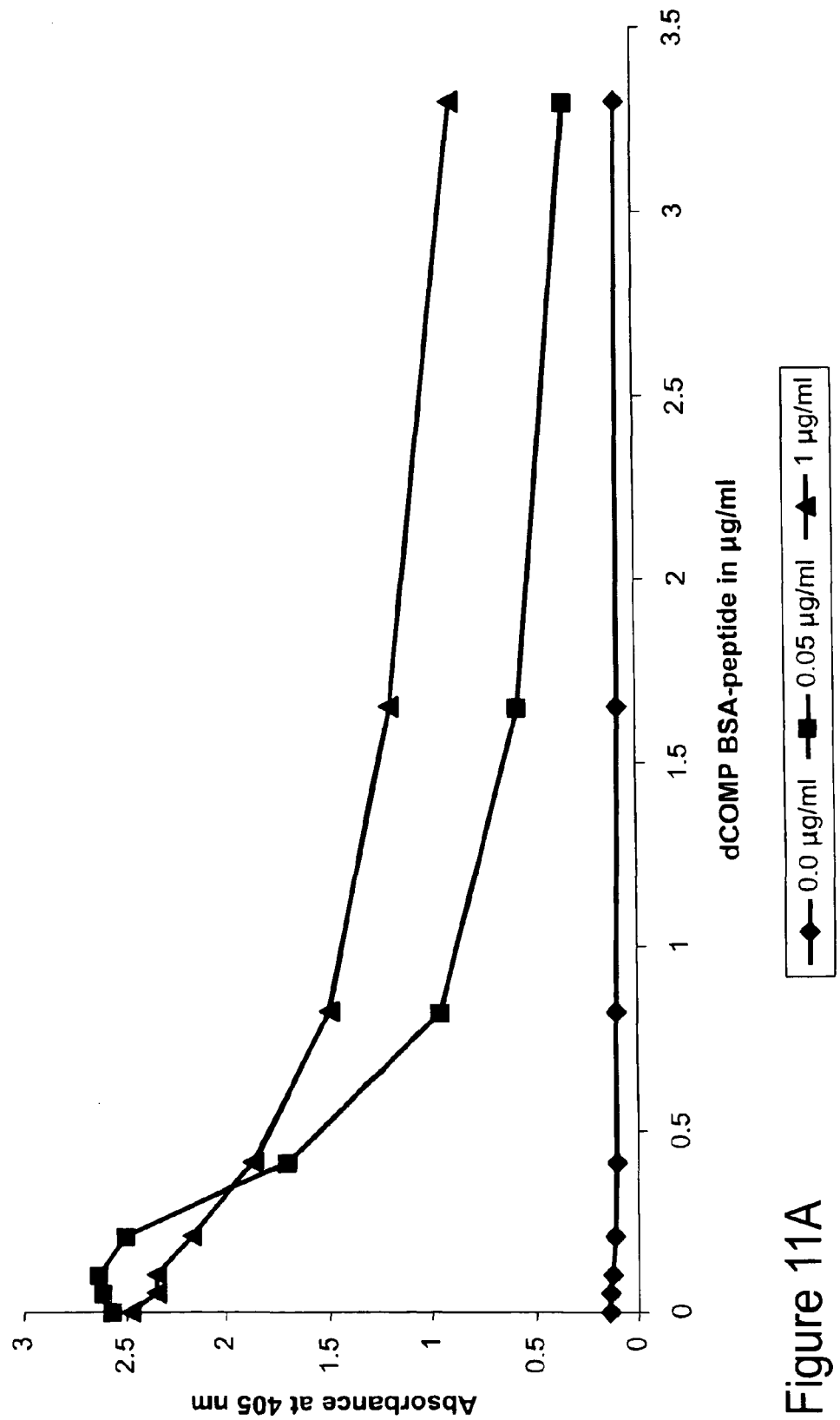
FIGS. 11A-11C. Standard curves for competitive ELISA generated using monoclonal antibody to a COMP deamidated epitope.
Figure 11B:
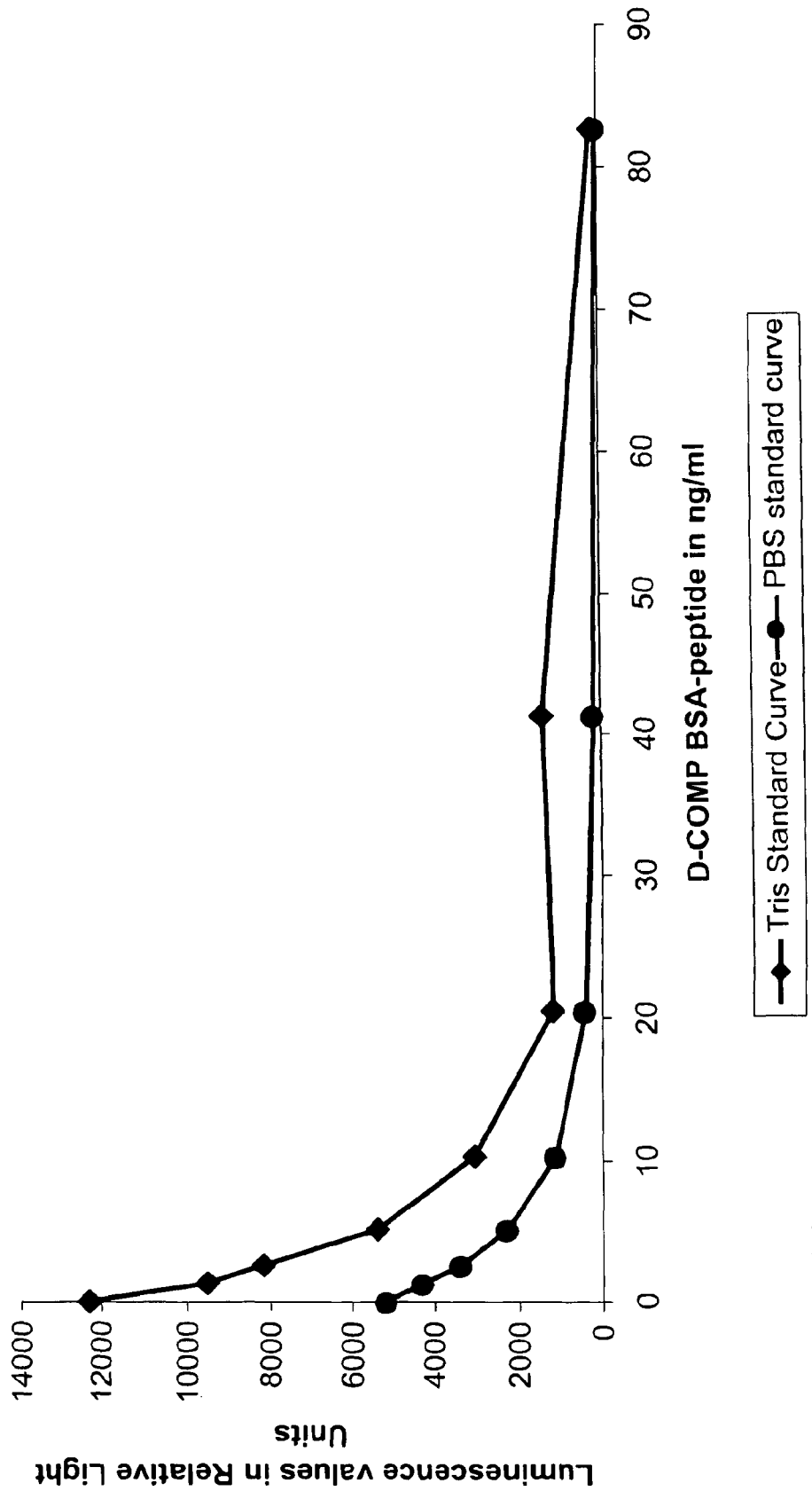
Figure 11C:
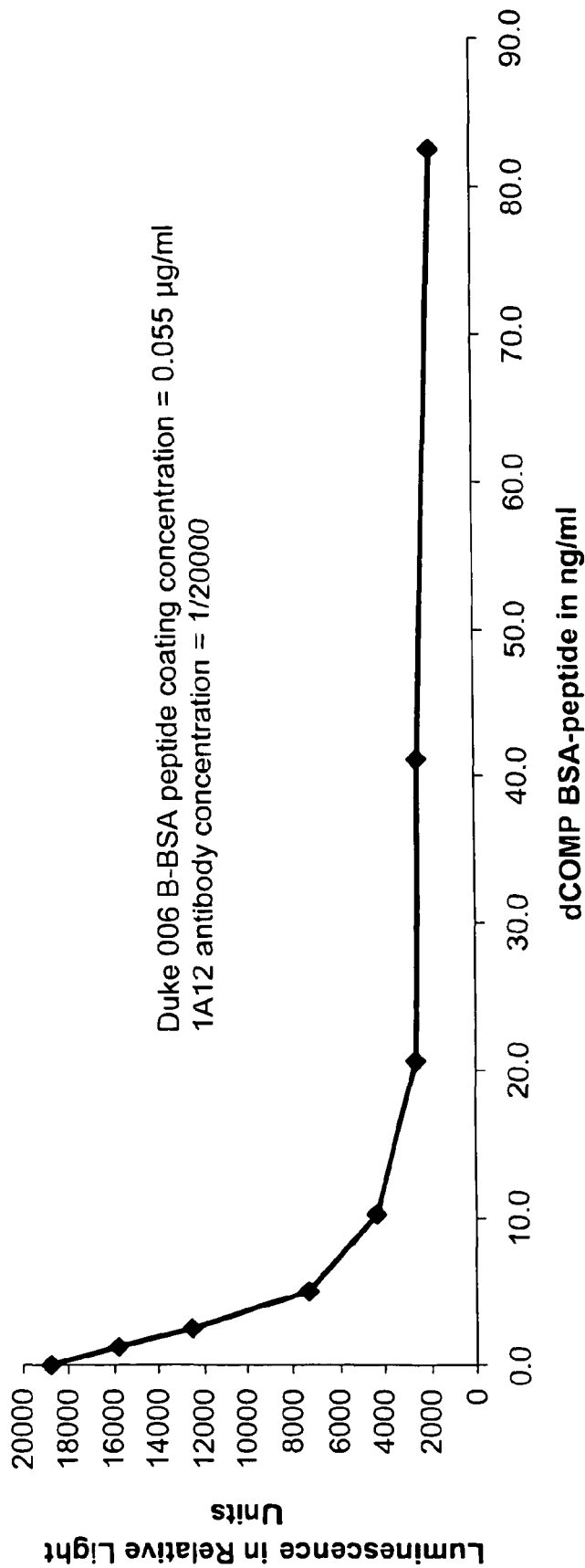

A novel competition ELISA has been developed that uses the peptide sequence used originally to generate the antibodies, coupled to BSA (FIG. 10). With one of the monoclonal antibodies (6-1A12) to a COMP deamidated epitope, this method has been used to develop a working competition ELISA that generates a sensitive standard curve. Using the 6-1A12 antibody, which is specific for the deamidated COMP sequence DUKE006 B, and the DUKE006 B-BSA conjugate, it was possible to generate the set of standard curves shown in FIG. 11. FIG. 11A shows the effect of decreasing the coating concentration of DUKE006-B-BSA while keeping the antibody concentration constant to determine the lowest practical coating concentration of DUKE006-B-BSA (0.0055 µg/ml in this case). Once the coating concentration was determined, the antibody concentration was titrated to improve the sensitivity, as the lower the antibody concentration the more sensitive a competition ELISA (FIG. 11B). From the data in FIGS. 11A and 11B, a set of conditions was selected using a coating concentration of 0.055 µg/ml DUKE006-B-BSA and an antibody concentration of 1/20,000 dilution. These conditions were used for synovial fluid assays (a typical standard curve is shown in FIG. 11C). With this format of the assay, the minimal detectable concentration was determined to be 2 ng/ml.

Figure 12:
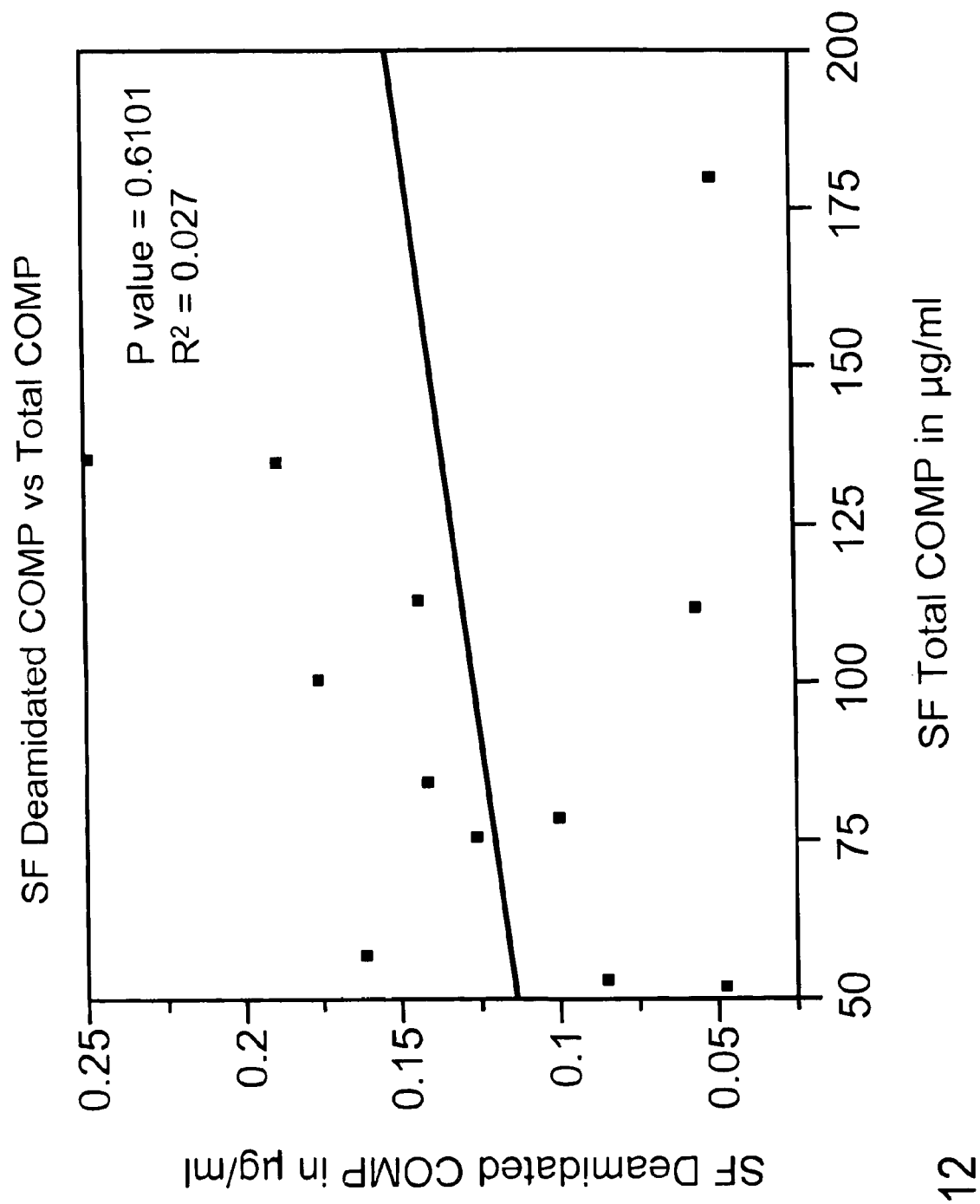
FIG. 12. Deamidated COMP versus total COMP in synovial fluid samples. D-COMP levels were determined relative to the Duke 006B peptide-BSA conjugated standard using the competition ELISA format as detailed in FIG. 10A.

To further validate the approach, the competition ELISA developed for the deamidated COMP 6-1A12 was used to determine whether deamidated COMP could be detected in biological fluids. A repository of synovial fluids (collected at OA end stage disease at the time of joint replacement) was available with known high levels of COMP. Using the competition ELISA for deamidated COMP, it was possible to detect deamidated COMP epitope in all 13 of the synovial fluids investigated (Table 3). As these samples were collected at end stage disease, it was not possible to perform any correlations between grade and amount of deamidated COMP epitope—most of the samples had the maximum 4 grade. However, these data indicate that even at end stage disease, there are detectable amounts of deamidated COMP present. The deamidated COMP was compared against total COMP (see FIG. 12). No correlation was found between the total amount of COMP in the synovial fluid and the actual amount of deamidated COMP in the synovial fluid. This means that the amount of deamidated COMP is independent of the total COMP expression and so, as a biomarker, it will behave differently to total COMP measurements.

TABLE 3

| Sample | Sex | Age | KL Grade | Collins Grade | SF Total COMP (ng/ml) | Deamidated COMP (ng/ml) |
|--------|-----|-----|----------|---------------|------------------------|--------------------------|
| DB9  | F | 74 | 4 | 4 | 84220  | 140.25 |
| DB16 | M | 76 | 4 | 4 | 134734 | 187.00 |
| DB17 | F | 69 | 4 | 4 | 135689 | 247.24 |
| DB19 | M | 77 | 4 | 4 | 56598  | 160.08 |
| DB20 | M | 59 | 4 | 4 | 180290 | 48.70  |
| DB21 | F | 54 | 4 | 3 | 51871  | 45.73  |
| DB22 | F | 79 | 4 | 4 | 53232  | 83.13  |
| DB23 | M | 75 | 4 | 4 | 78546  | 99.09  |
| DB24 | M | 62 | 4 | 4 | 100884 | 174.66 |
| DB25 | F | 65 | 3 | 2 | 75409  | 125.57 |
| DB26 | M | 59 | 3 | 4 | 113275 | 54.74  |
| DB27 | M | 60 | 4 | 4 | 111826 | 142.18 |

Figure 13A:
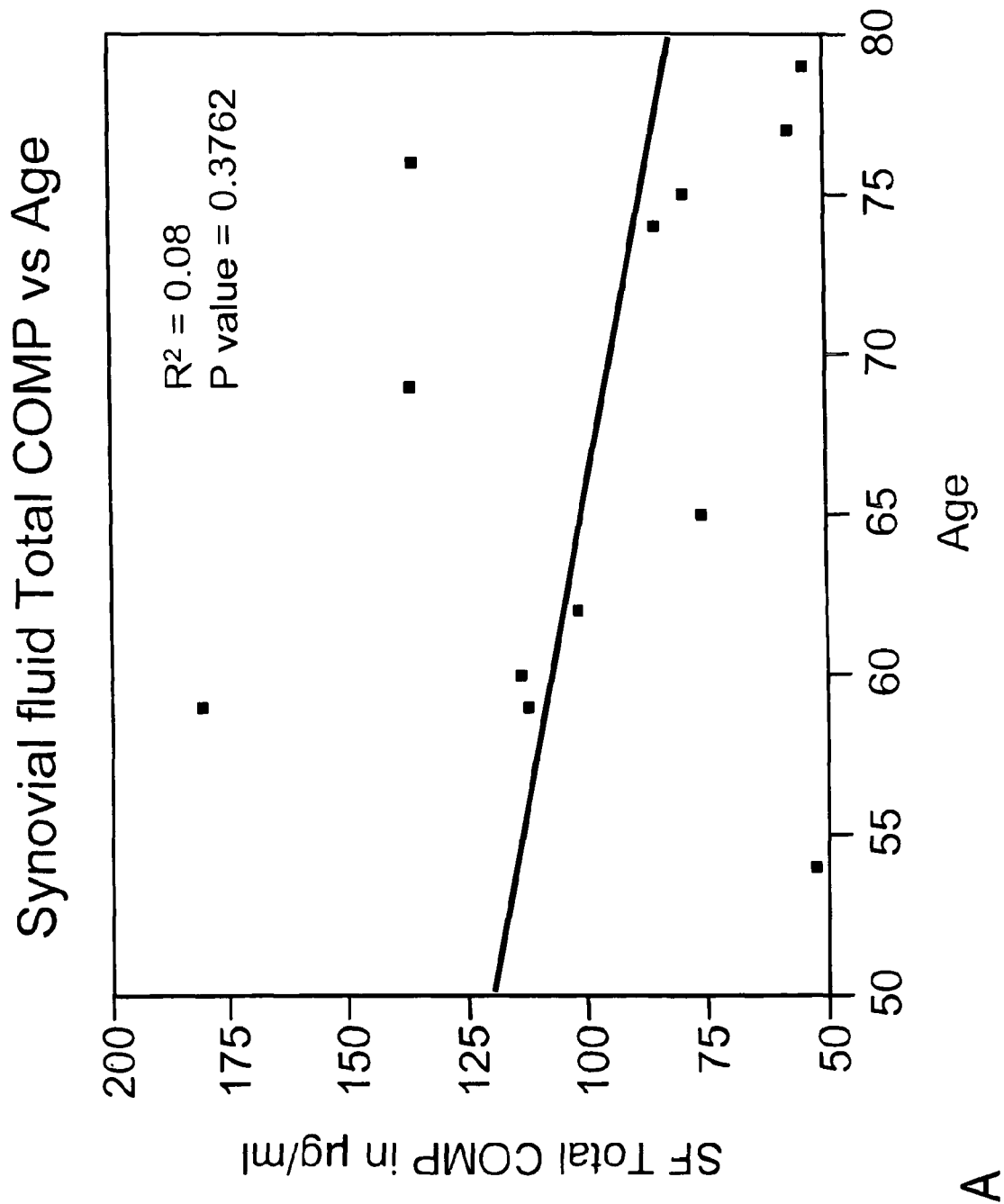
FIGS. 13A-13C.
Figure 13B:
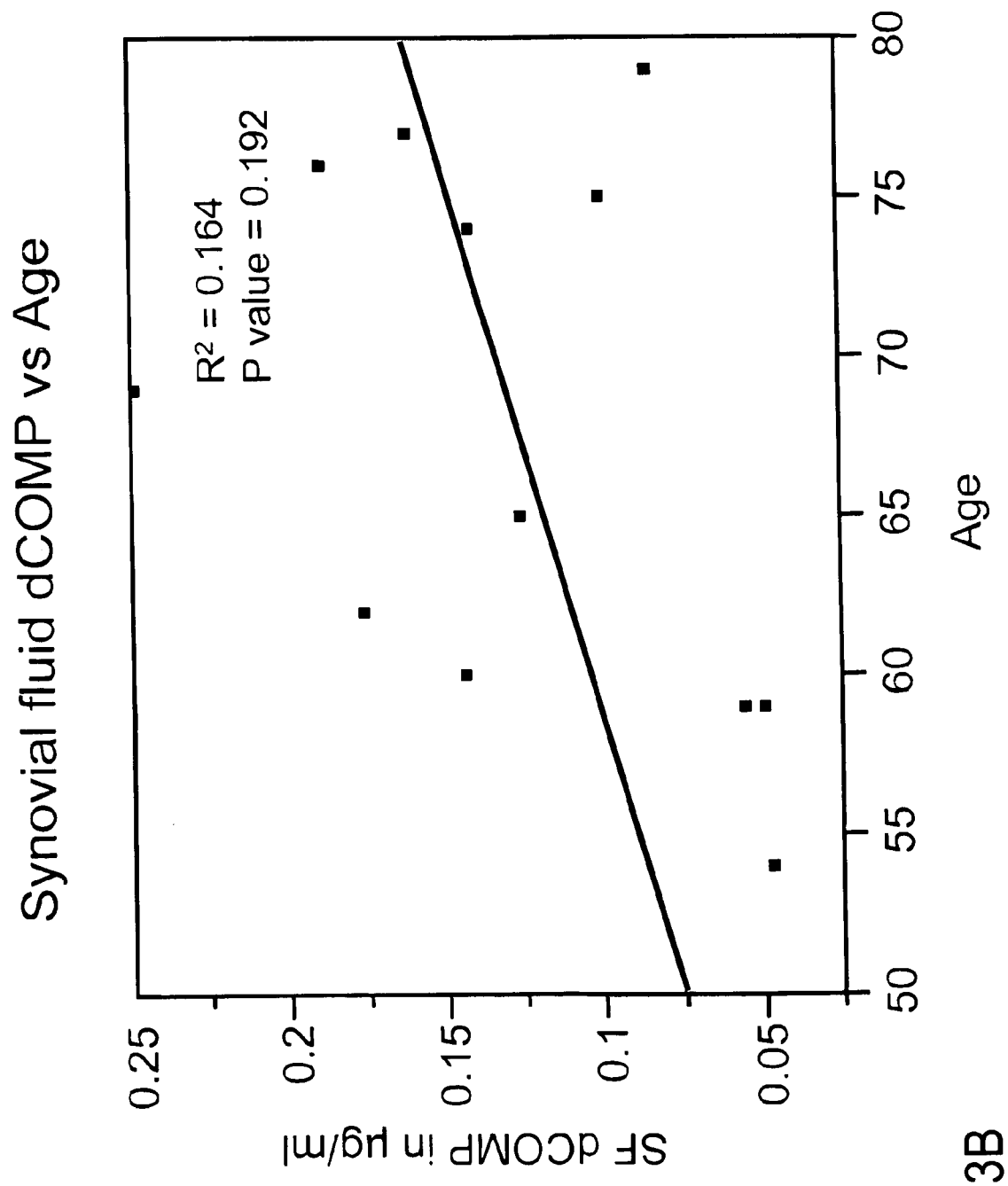
Figure 13C:
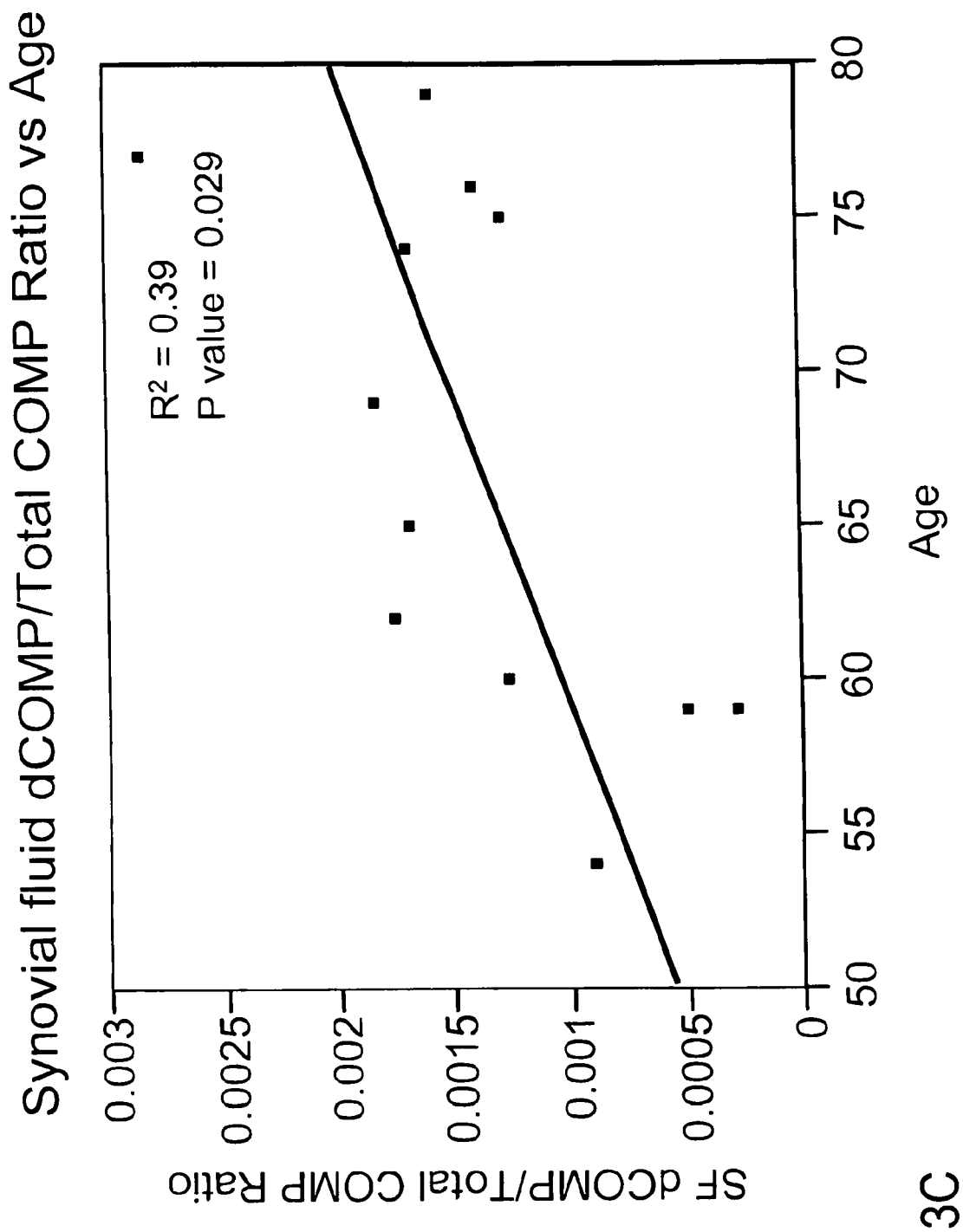

An investigation was made of the association of total COMP and deamidated COMP to the chronological age of the patients (FIG. 13). When total synovial fluid COMP (FIG. 13A) or total synovial fluid deamidated COMP (FIG. 13B-measured by competitive ELISA described in Example 2) was compared against age, no significant correlation was found, although the deamidated COMP showed a slight age-related trend. However, evaluating the ratio of synovial fluid deamidated COMP/total synovial fluid COMP (FIG. 13C), a significant ($p=0.029$) linear relationship with age was found. This suggests that, as a person ages, the proportion of age-related changes build up and become a higher proportion of the total pool. This result validates the underlying hypothesis that the molecular alteration of deamidation is indeed reflecting age-related processes. In addition, this assay can be used to further understand the metabolism of a specific aged subset of an extracellular matrix protein.

EXAMPLE 4

Described below are the results of a joint replacement study.

Both serum and plasma samples were collected before joint replacement (baseline samples) and at a time 6 months post joint replacement. In these samples, both total COMP (T-COMP) and the deamidated COMP (D-COMP) were measured. This was a subtractive study in that the affected arthritic joint contributing the markers, was removed and so the biomarkers contributed from that affected joint should decrease.

The purpose of this study was to measure biomarkers in the blood before and after joint replacement surgery to:

1) provide data to increase confidence that a systemic biomarker is representative of a joint related process. A biomarker originating from the joint would be expected to decrease in the systemic circulation or urine upon removal (replacement) of the damaged joint.

2) characterize the amount of a biomarker contributed by a single hip or knee joint through inference, based on the amount of the decrease of the marker, when the damaged joint is removed (replaced).

Anyone over the age of 18 planning to have a joint replacement was eligible to participate in this study. However, those undergoing joint replacements due to joint infection were not eligible, as this condition would alter the biomarker levels in a manner that could not be predicted and would not be useful to this study.

Experimental Details:

T-COMP (native amidated and deamidated COMP) was measured by sandwich ELISA (FIG. 10B) using monoclonal antibodies 16F12 and 17C10 to total T-COMP provided as a gift from Dr. Vladimir Vilim (Vilim et al, Clin. Chim. Acta 328:59-69 (2003)), D-COMP was measured with monoclonal antibody 6-1A12 by competition ELISA (FIG. 10A). Briefly, the deamidated Duke 006B epitope to which the antibody was raised was coupled to BSA and this BSA/peptide conjugate was bound to an ELISA plate. The D-COMP specific monoclonal antibody 6-1A12 was either incubated with BSA-peptide conjugate to produce a standard curve or incubated with the sample (serum). After 30 minutes of incubation, the antibody/BSA-peptide or antibody/sample was transferred to the coated BSA-peptide plate, incubated for 1 hour before washing and the amount of residual 6-1A12 binding determined using an anti-mouse-HRP coupled antibody and bioluminescent detection.

Figure 14:
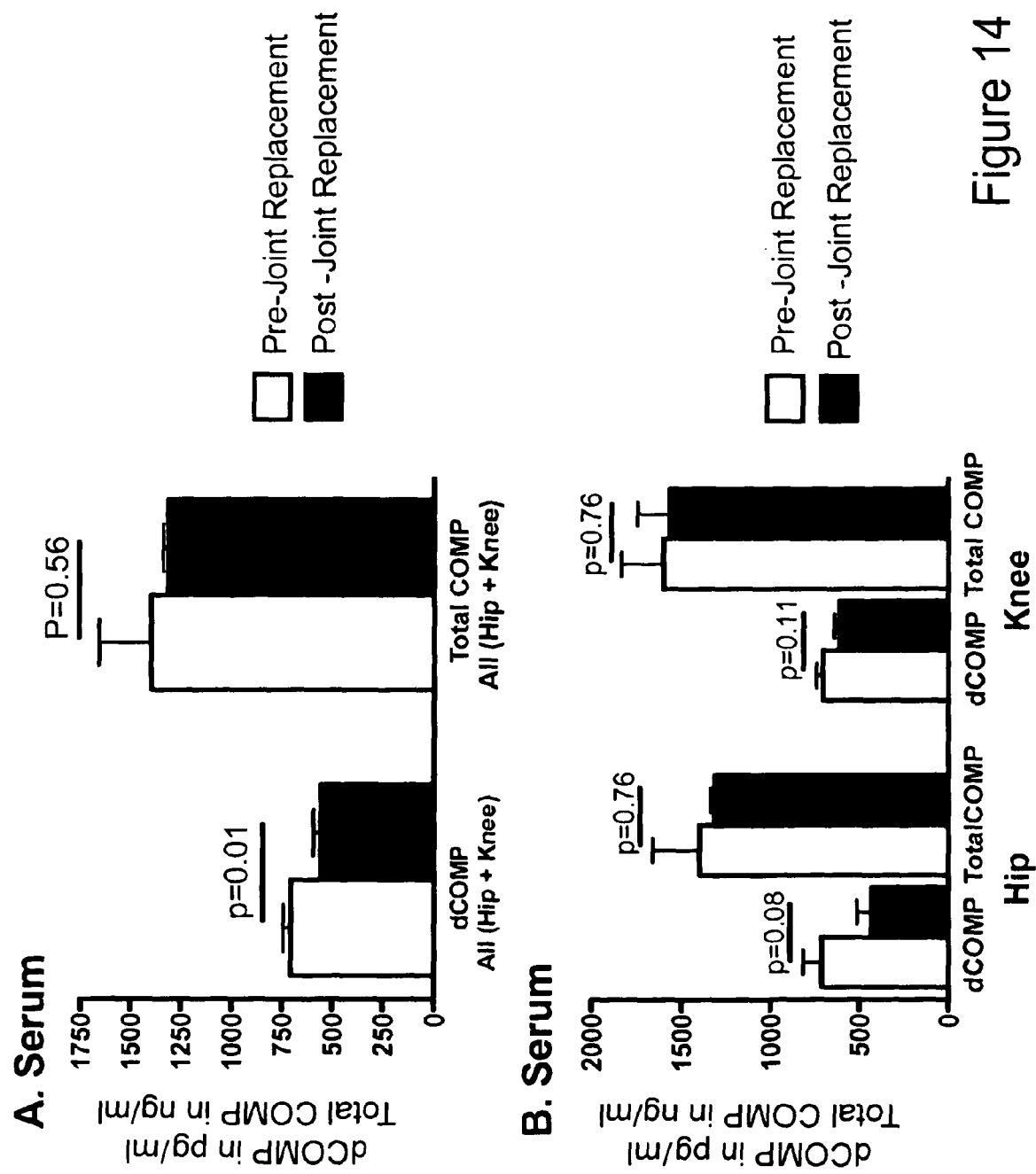
FIGS. 14A-14C. Serum COMP data before (baseline) and after (6 months) knee or hip joint replacement and amounts of deamidated and native COMP in hip and knee OA cartilage.
Figure 14:
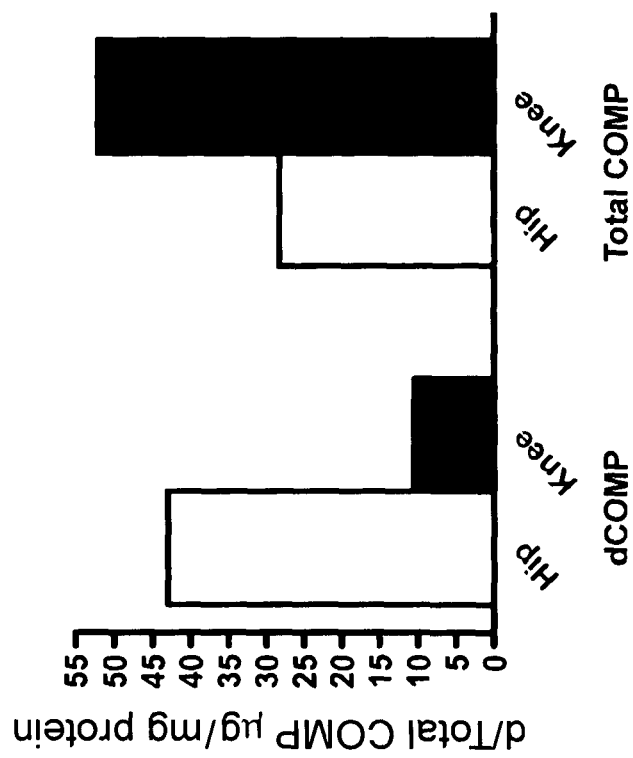

All the data used for analysis passed the following tests for a Gaussian distribution: KS normality test, D'Agostino & Pearson omnibus normality test, Shapiro-Wilk normality test and so was analyzed for significance using paired student T-tests. N=15 for this study. The data were further stratified according to type of joint replacement, i.e. Hip (n=4) or Knee (n=11) and results analyzed for evidence of joint site specificity of the total versus deamidated COMP measurements (FIG. 14A-B).

In addition, COMP concentrations in cartilage were determined by extracting COMP from a hip OA specimen from a 69 year old male, and a knee OA specimen from a separate 69 year old male. OA cartilage was extracted from around the OA lesion area. Cartilage was pulverized under liquid nitrogen before extraction with buffer (4M guanidine-HCl, 0.05M sodium acetate, 0.01M EDTA, protease inhibitors) at a ratio of 0.5 ml buffer per 0.1 g of powdered cartilage for 24 hr at 4° C. After extraction, samples were briefly centrifuged to pellet undissolved debris and the supernatants collected. Samples were buffer exchanged into phosphate buffered saline ready for the ELISA analysis using an AKTA HPLC system fitted with a PD10 size exclusion column. Protein content was determined using the Bradford Protein assay (Piece) post dialysis. COMP concentrations were normalized to total protein which did not differ significantly between hip and knee extracts. Deamidated COMP was measured by sandwich ELISA (FIG. 10B) described below.

Sandwich ELISA Method for Tissue Extracts. 50 µl/well of capture antibody (61A12 for DCOMP or 16F12 for total COMP) (5 µg/ml in carbonate buffer, pH 9.3) was added to NUNC Maxisorp strips. Strips were shaken for 1 hr at room temp on an orbital shaker then transferred to a cold room and incubated at 4° C. for 72 hrs without shaking. Capture antibody was discarded from strips and 150 µl/well of blocking buffer (3% BSA in PBS, pH 7.4) was added. Strips were incubated with shaking for 2 hr at room temp. Blocking buffer was discarded and strips were washed 5 times with wash buffer (PBS with 0.05% Tween 20, pH 7.4). Sample and/or standard was ×2 serially diluted (from undiluted to ×64, 8 wells per sample) on a separate polypropylene plate using assay buffer (PBS with 0.1% BSA, pH 7.4). 50 µl of sample and/or standard was transferred to the coated and blocked strips. Strips were shaken for 1 hr at room temp on an orbital shaker then transferred to a cold room and incubated at 4° C. for 24 hrs with rocking. Strips were washed 5 times with wash buffer. 50 µl of biotinylated 17C10 detection antibody (1 µg/ml in assay buffer) was added to each well followed by shaking for 2 hr at room temp. Strips were again washed 5 times with wash buffer. 50 µl of Pierce Streptavidin Poly- HRP (Pierce, Rockford, Ill.) diluted ×20,000 in PBS with 1% BSA was added to each well. Strips were incubated with shaking for 1 hr at room temp. Strips were again washed 5 times with wash buffer. 100 μl of TMB substrate (Sigma-Aldrich, St. Louis, Mo.) was added to each well. Strips were incubated in the dark at room temp for 30 min without shaking. 100 μl of stop solution (2M HCl) was added to each well. Plates were read on plate reader at 450 nM and standard curve constructed from OD's. Samples were calculated from standard curve.

Results:

Serum Data i) D-COMP decreased following joint replacement of either the hip or knee (p=0.01) (FIG. 14A) comparing baseline (pre-operative) and 6 month (post-operative) samples; there was no change in T-COMP following joint replacement (p=0.56) (FIG. 14A).

ii) D-COMP decreased following hip joint replacement (p=0.08) but not knee joint replacement (p=0.11); there was no change in T-COMP following hip or knee joint replacement (p=0.76 and p=0.76 respectively) (FIG. 14B).

Cartilage Extract Data iii) The concentration of D-COMP (normalized to total protein concentration) is much greater in hip cartilage than knee cartilage (FIG. 14C left panel). The concentration of T-COMP (normalized to total protein concentration) is greater in knee cartilage than hip cartilage (FIG. 14C right panel).

These results support the utility of D-COMP as a marker of hip disease.

EXAMPLE 5

Described below are the results of a hip and knee osteoarthritis study. Patients' hips and knees were X-rayed to determine hip and knee OA (presence/absence) and OA severity status. Serum samples were also collected at the time of X-ray performance. In these samples, both total COMP (T-COMP) and the deamidated COMP (D-COMP by sandwich ELISA as described in Example 4) were measured. The sandwich ELISA for D-COMP was used for these measurements and was developed to increase the assay sensitivity and reproducibility compared with a competition ELISA.

The purpose of this study was to measure biomarkers in the blood to:

1) provide data to increase confidence that a systemic biomarker is representative of a joint related process. A biomarker originating from the joint would be expected to increase in the systemic circulation or urine with progressive and ongoing joint breakdown, and, 2) to evaluate the joint site specificity (hip versus knee) of D-COMP and N-COMP measurements.

Patient samples were a gift from Dr. Joanne Jordan, University of North Carolina, Chapel Hill. Samples were provided from a total of 450 individuals.

Experimental Details:

This patient sample (N=450) spanned a broad age range and was balanced by gender and consisted of 40% African Americans. Bilateral hip and knee X-rays were graded for OA severity on the basis of Kellgren Lawrence (KL) score. In addition, the severity of specific radiographic features of knee OA were graded (using a standard atlas) on half the cohort including knee joint space narrowing (JSN) and knee osteophyte (OST). As described in Example 4, T-COMP (total COMP) was measured by sandwich ELISA (FIG. 10B) using monoclonal antibodies 16F12 and 17C10 to total T-COMP, gift from Dr. Vladimir Vilim (Vilim et al, Clin. Chim. Acta 328:59-69 (2003)), D-COMP was measured by sandwich ELISA with monoclonal antibody 6-1A12 and 17C10 as described in FIG. 10B. The associations of D-COMP and T-COMP were evaluated with the outcome variables: hip KL, knee KL, knee JSN, and knee OST. Biomarker data were log transformed to achieve normality for statistical analysis. To test the association between the KL, JSN, and OST (all ordinal measures), and log T-COMP and log-D-COMP (continuous measures), a generalized linear model (cumulative logit model) was used. Because radiographic data from the left knee and the right knees of the same person are likely correlated, the intra-individual correlation was estimated in the model as a variance component.

Results:

Results demonstrate that D-COMP is a burden of disease marker for radiographic HIP Osteoarthritis (OA) and T-COMP is a burden of disease marker for radiographic KNEE OA (FIG. 15). The sample included 900 knees and 900 hips (from the 450 individuals) with the following frequencies of knee OA severity by Kellgren-Lawrence grade: 535 KL0, 153 KL1, 115 KL2, 81 KL3, 14 KL4, 2 knee replacements; and the following frequencies of hip OA: 73 KL0, 512 KL1, 287 KL2, 20 KL3, 4 KL4 and 4 hip replacements. The statistical analysis indicated that the severity of hip OA (Hip-KL) was highly positively associated with serum D-COMP concentration (p<0.0001) but not T-COMP (p>0.05) (FIG. 15); it also indicated that the severity of knee OA (Knee-KL, Knee-JSN or Knee-OST scores) was highly positively associated with T-COMP (p<0.0001) but not D-COMP (p>0.05). These data demonstrate that the new D-COMP biomarker is a marker of hip OA and hip OA severity distinct from knee OA. These data also show that the extant biomarker T-COMP is a marker of knee OA and knee OA severity as distinct from hip OA.

To provide an indication of relative amounts of dCOMP and tCOMP possible for Hip OA and Knee OA relative to OA severity and relative to control, a calculation was made of the mean, standard error and 95% confidence intervals for natural log transformed d- and t-COMP values for each level of OA severity.

FIG. 16 shows the d- and t-COMP values for controls (hip OA controls have KL0 hips bilaterally; knee OA controls have KL0 knees bilaterally), and definite radiographic OA (sum of hip KL scores >2; sum of knee KL scores >2). These results clearly show an incremental increase of d-COMP (but not t-COMP) with increasing severity or burden of hip OA. These results also clearly shown an incremental increase of t-COMP (but not d-COMP) with increasing severity or burden of knee OA. The confidence intervals around the higher severity scores are wider due to smaller numbers of individuals affected with more severe disease.

EXAMPLE 6

Experimental Details

Patient Samples

The BAJA (Biomarker and Joint Arthroplasty) cohort provided serum samples drawn before, and 6 months after, either total hip or knee arthroplasty. There were 14 subjects within the study (9 male and 5 female). As summarized in Table 4, 10 individuals underwent total knee replacement (6 male and 4 female) and 4 underwent total hip replacement (3 male and 1 female). The overall mean age was 63.4±13.2 years (59.6±13.8 years for men and 70.2±9.8 for women). The population was overweight with a mean BMI of 26.8±5.8

(27.8±5.6 for men, 25.0±6.6 for women). Samples were collected under approval of the Institutional Review Board of Duke University.

TABLE 4

Cohort demographics.

| | BAJA | JoCo$_{450}$ | Human Cartilage |
|---|---|---|---|
| N (% female) | 14 (36%) | 450 (54%) | 26 (42%) |
| Age mean ± SD years (range) | 63.4 ± 13.2 (44-81) | 15% aged 45-54 years 39% aged 55-64 years 46% aged 65 years and older | 72.4 ± 11.7 (54-90+) |
| No OA (N) | 0 | 164 | N/A |
| Hip OA (N) | 4 | 143 | 11 |
| Knee OA (N) | 10 | 79 | 15 |
| Hip and Knee OA (N) | 0 | 64 | N/A |

A second cohort, the Johnston county OA Project (JoCo) provided serum samples from 450 individuals (JoCo$_{450}$). The JoCo project is an ongoing, community-based study of knee and hip OA in African American and Caucasian residents in a rural county in North Carolina. Details of this study have been reported previously (Jordan et al, Arthritis Care and Res. 8(4):242-250 (1995)) and demographics are summarized in Table 4. Briefly, this study involved civilian, non-institutionalized adults aged 45 years and older who resided in six townships in Johnston County. Participants were recruited by probability sampling, with over-sampling of African Americans. A total of 3,187 individuals completed a baseline clinical evaluation from 1991-1997. Serum was collected for all participants at baseline. To allow for analyses of biomarkers in a sample balanced for gender and age, 450 participants were selected with complete radiographic data at baseline to represent roughly equal proportions of women (54%) and men (46%) across a range of ages (15% aged 45-54 years, 39% aged 55-64 years, and 46% aged 65 years and older). A total of 39% of participants were African American. Individuals having radiographic evidence of rheumatoid arthritis or other inflammatory arthropathies in the knees or hips were not included in the subsample. At baseline and follow-up, participants completed bilateral anteroposterior weight-bearing radiography of the knees with foot mat placement and supine anteroposterior hip radiographs. Radiographs were read, without knowledge of participant clinical or biomarker status, by a single musculoskeletal radiologist (JBR) for overall radiographic severity by Kellgren-Lawrence Kellgren and Lawrence (Ann Rheum. Dis. 16(4):494-502 (1957)) (score 0-4) of the knees and hips, and read for osteophyte (OST, score 0-3) and joint space narrowing (JSN, score 0-3) based on the standardized Burnett atlas (Burnett et al, "A Radiographic Atlas of osteoarthritis, London: Springer-Verlag (1994)). Inter-rater reliability (comparison of radiograph readings between JBR and another radiologist) and intra-rater reliability (comparison of radiograph readings completed by JBR at two separate times) for the radiologist were high (weighted kappa for inter-rater reliability 0.9; kappa for intra-rater reliability 0.9) (Jordan et al, Arthritis Care and Res. 8(4):242-250 (1995)). The study was conducted under approval of the Institutional Review Board of the University of North Carolina at Chapel Hill.

A third set of samples was obtained as waste articular cartilage specimens from randomly selected total knee (n=15) and total hip (n=11) arthroplasties performed to alleviate symptoms of OA. Patient characteristics are summarized in Table 4. From each arthritic joint, cartilage was harvested around the lesion (lesion cartilage), and for comparison, cartilage was harvested from macroscopically normal cartilage that was remote from the lesion (remote cartilage). Non-arthritic control samples were obtained from trauma patients who showed no signs of OA as determined by the surgeon and macroscopic inspection of the specimens. Samples were collected under Duke Institutional Review Board approval as waste surgical specimens.

Monoclonal Antibody Generation and Screening

To generate novel specific monoclonal antibodies (mAbs) to investigate the theoretical deamidated epitopes in COMP, a COMP peptide, TFLKD$_{64}$TVMEC (SEQ ID NO:3) specific for the deamidated epitope, was used to immunize mice (A&G Pharmaceutical, Columbia, MD). Antibody specificity was confirmed using a direct ELISA. Briefly, 96 well ELISA plates were coated with COMP purified from hip cartilage (a gift from Dr. V. Vilim), or bovine serum albumin (BSA) conjugated to the deamidation specific COMP peptide (EITFLKD$_{64}$TVMEC) (SEQ ID NO: 21) or the non-deamidated native COMP peptide (EITFLKN$_{64}$TVMEC) (SEQ ID NO: 22). For later screening experiments, two further constructs were synthesized with different peptides coupled to the same BSA molecule; one BSA-peptide construct contained both the deamidation specific Asp$_{64}$ peptide EITFLKD$_{64}$TVMEC) (SEQ ID NO: 21) and the native CELQETN$_{42}$AALQ) (SEQ ID NO: 6) sequence; and the other coupled both the native Asn$_{64}$ EITFLKN$_{64}$TVMEC) (SEQ ID NO: 22) and the native CELQETN$_{42}$AALQ) (SEQ ID NO: 6) peptides to the same BSA protein (the N-terminal C is not part of the native sequence but was added for coupling purposes). The COMP peptides (procured from AnaSpec, Fremont, CA) or the purified COMP were coated in 0.1 M sodium carbonate/bicarbonate coating buffer pH 9.6 overnight at 4° C. Plates were blocked overnight with 5% BSA in phosphate buffered saline (PBS), pH 7.4 at 4° C. before excess blocking buffer was discarded and the plates were washed with 0.05% v/v PBS wash buffer. Washed wells were incubated with undiluted hybridoma supernatants overnight at 4° C. Unbound antibody was discarded and washed with 0.05% v/v tween 20 in PBS, pH 7.4 (PBS-tween) before addition of alkaline phosphatase conjugated anti-mouse antibody (Promega, Madison, WI) and development with o-phenylenediamine dihydrochloride (OPD) substrate and detection at 450 nm.

Protein G Antibody Purification

Monoclonal antibodies were purified using Protein G sepharose (Thermo Scientific, Rockford, Ill.) per the manufacturer's instructions. Briefly, antibodies to be concentrated were grown up in roller bottle culture in serum free hybridoma medium (Sigma Aldrich, St Louis, Mo.). The supernatants were collected, filtered through a 0.2 μM filter and concentrated 20-fold using Amicon stirred ultrafiltration cells with a 100 kDa molecular weight cut-off (Millipore, Billerica, Mass.). A column with a 1 ml bed volume of protein G sepharose was prepared; 5 ml of concentrated antibody (diluted 1:1 in 20 mM in sodium phosphate binding buffer, pH 7.0) was allowed to pass through the column under gravity. Unbound proteins were washed from the column with a further 5 ml of binding buffer; this wash was collected in 1 ml aliquots and a Bradford protein assay was performed to confirm all unbound protein was removed from the column. Antibodies were eluted from the column with 0.1 M glycine-HCl, pH 2.7 and 0.5 ml and aliquots were collected. Each aliquot was neutralized with 1 M Tris buffer pH 7.4 to prevent antibody degradation. Fractions containing antibody, as determined by a Bradford protein assay, were pooled and dialysed against PBS to remove any primary amines which would interfere with future biotinylation. A final antibody concentration was determined by Bradford protein assay and the purified mAbs were aliquoted and stored at −80° C. until needed.

Extraction of Soluble Cartilage Matrix Proteins

Cartilage was pulverized under liquid nitrogen and extracted in 4M Guanidine-HCl (Gu-HCl) in sodium acetate buffer pH 4.0 with protease inhibitor cocktail (Sigma-Aldrich, St Louis, Mo.) at a ratio of 2 ml of Gu-HCL extraction buffer per 1 g of wet weight cartilage. Cartilage was extracted for 24 hr at 4° C. with gentle mixing, followed by centrifugation and collection of the supernatant. The remaining cartilage was extracted a second time with Gu-HCl extraction buffer for a further 24 hr. Both the first and second Gu-HCl extractions were combined and stored at −80° C. until needed. A 200 µl aliquot of the extract was buffer exchanged on an AKTA purifier 10 (GE Healthcare, Pittsburgh, Pa.) using a HiTrap Desalting column (GE, Pittsburgh, Pa.) into PBS and stored at −80° C. Protein concentrations in the PBS extracts were determined using the Bradford protein assay (Thermo Scientific, Rockford, Ill.) to allow normalizations of values to protein content.

Mass Spectroscopic Identification of Deamidated Comp

To remove residual Gu-HCl to prevent interference with liquid chromatography-mass spectroscopy (LC-MS/MS) analyses, Gu-HCl cartilage extracts were buffer exchanged into 50 mM ammonium bicarbonate, pH 7.8 using a HiTrap desalting column on an AKTA HPLC system. After dialysis, 0.1% v/v rapigest (Waters, MA, USA) was added before reduction with 10 mM dithiothreitol at 80° C. for 15 minutes. Proteins were alkylated using 20 mM iodoacetamide for 30 min at room temperature before the addition of proteomics grade trypsin (Sigma-Aldrich, St Louis, Mo.) overnight at 37° C. at a 1:30 ratio of trypsin to protein. After digestion, the rapigest was cleaved by the addition of 1% trifluoracetic acid and 1% acetonitrile and incubation for 2 hr at 60° C. Prior to LC-MS/MS analysis, all samples were resuspended in 20 µL 2% acetonitrile, 0.1% formic acid (pH 3.0). Chromatographic separation of peptide mixtures was performed on a Waters NanoAquity UPLC equipped with a 1.7 µm BEH130 $C_{18}$ 75 µm I.D. X 250 mm reversed-phase column. The mobile phase was (A) 0.1% formic acid in water and (B) 0.1% formic acid in acetonitrile. Peptides were trapped for 5 mins on a 5 µm Symmetry $C_{18}$ 180 µm I.D. X 20 mm column (Waters, Milford MA) at 20 µl/min in 99.9% buffer A. The analytical column was switched in-line and the mobile phase held for 5 mins at 5% B before applying a linear elution gradient of 5% B to 40% B over 90 mins at 300 nL/min. The analytical column was connected to a fused silica PicoTip emitter (New Objective, Cambridge, MA) with a 10 µm tip orifice and coupled to the mass spectrometer through an electrospray interface. MS analysis was performed on a Waters Synapt G2 mass spectrometer operating in positive-ion mode with an electrospray voltage of 3.2 kV. Samples were analyzed using two different acquisition strategies, qualitative only and qualitative/quantitative. For a qualitative only acquisition, the instrument was operated in a data-dependent acquisition (DDA) mode with a precursor MS scan from m/z 50- 1990 followed by up to 3 MS/MS product ion scans from m/z 50-1990 with a charge-state dependent CID energy setting. For a qualitative/quantitative acquisition, the instrument was operated in a data-independent high-energy/low-energy alternative scanning ($MS^E$) acquisition mode with a 0.9 s low-energy precursor MS scan from m/z 50-1990 followed by a high-energy MS scan from m/z 50-1990 with a CID energy set to ramp from 15-40 volts. To increase coverage of lower abundant precursor ions, a 120 s dynamic exclusion list was employed. For both acquisitions, a separate LC channel with 200 fmol/µL Glu-1-Fibrinopeptide in 50% acetonitrile/0.1% formic acid flowing at 500 nL/min was referenced every 30 secs through a nano lock-spray interface. Label-free quantification and integration of qualitative peptide identifications was performed using Rosetta Elucidator (v 3.3, Rosetta Inpharmatics, Seattle, WA). All raw LC-MS/MS data were subjected to chromatographic retention time alignment using the PEAKTELLER algorithm (noise filtering algorithm) with a minimum peak time width set to 6 secs, alignment search distance set to 4 mins and the refine alignment option enabled. Quantification of all signals in the precursor MS spectra above a threshold of 0 was performed by Elucidator by calculating peak volume (area under curve). Qualitative peptide identifications were made for MSe data by importing search results of high-energy MS data from Protein Lynx Global Server (PLGS). DDA data was searched with Mascot (Matrix Science, Boston, MA) against a human protein database downloaded from SwissProt appended with Yeast ADH. The entire database was concatenated with the sequence-reversed version of each entry. Search tolerances of 10 ppm precursor and 0.04 Da product ions was applied for Synapt G2 data files, with lock-mass correction on 785.8426 Da (doubly-charged Glu-1-Fibrinopeptide ion) enabled. All data were searched using trypsin specificity with up to two missed cleavages. Peptide FDR was determined by the PeptideTeller algorithm and set to achieve a 1% false discovery rate or lower.

D-COMP and Total COMP ELISAs

The D-COMP sandwich ELISA was based upon capture with the D-COMP specific mAb 6-1A12, and detection with 17-C10, a mAb to total COMP (specificity for COMP irrespective of deamidation state) (Vilim et al, Osteoarthritis Cartilage 9(7):612-618 (2001)). Briefly, antibody coating concentrations were optimized (data not shown) and 96 well ELISA plates were coated with G-protein purified D-COMP specific mAb (6-1A12) in 0.1M sodium carbonate/bicarbonate coating buffer, pH 9.6 overnight at 4° C. Plates were blocked for at least 2 hours with 5% BSA in PBS, pH 7.4 at 37° C. before excess blocking buffer was discarded and the plates washed with 0.05% v/v PBS-tween wash buffer. Samples or standard were diluted in 0.1% w/v BSA in PBS as required prior to addition of 50 µl of sample to the plate overnight at 4° C. with gentle mixing. Unbound sample was discarded and the plate washed with 0.05% v/v PBS-tween wash buffer before the addition of biotinylated 17-C10, total COMP detection antibody (a gift from Dr. V. Vilim). Unbound 17-C10 was discarded and the plate washed. Due to the lower levels of D-COMP than total COMP in the samples, the ELISA sensitivity was increased using avidin poly-horse radish peroxidase (poly-HRP, Thermo Scientific, Rockford, Ill.), added for 30 min at room temperature with gentle mixing. Excess avidin-HRP was discarded, the plate washed and signal detected using tetramethyl benzidine (TMB, Sigma-Aldrich, St Louis, Mo.) reagent after stopping with 2M HCl and detection at 450 nm.

Total COMP was measured using the 16-F12 and 17-C10 antibodies as previously described (Vilim et al, Osteoarthritis Cartilage 9(7):612-618 (2001)) with several modifications. For this project, the detection system used was avidin-HRP and TMB so that the total COMP and D-COMP methods were as similar as possible.

D-COMP Standard for ELISA

To generate a standard for the D-COMP ELISA, hip OA cartilage from 3 separate patients (obtained as surgical waste specimens) were extracted with Gu-HCl. Briefly, cartilage was pulverized under liquid nitrogen and extracted in 4M Gu-HCl in sodium acetate buffer pH 4.0 with protease inhibitor cocktail (Sigma Aldrich, St Louis, Mo.) at a ratio of 2 ml of Gu-HCL extraction buffer per 1 g of wet weight cartilage. Cartilage was extracted for 24 hr at 4° C. with gentle mixing, before centrifugation and collection of the supernatant. The remaining cartilage was extracted a second time with Gu-HCl extraction buffer and both the first and second extractions combined and buffer exchanged by dialysis into PBS. Total COMP levels in the extract were determined using the Total COMP ELISA and the levels of D-COMP within this sample estimated by dividing the total COMP by 105 based on determinations of the abundance of these two epitopes in 5 cartilage Gu-HCl extracts by LC-MS-MS as described below.

Western Blot Protocol

PBS cartilage extract and precision plus prestained protein standards (5 µg/well, BioRad, Hercules, Calif.) were separated under reducing conditions on a 10% SDS-PAGE. Proteins were transferred to a nitrocellulose membrane. After transfer the membrane was blocked with 3% w/v milk proteins for 2 hr at room temperature. The blocked membrane was incubated with 6-1A12 or 17-C10 mAbs in PBS 1% w/v milk proteins overnight at 4° C. Excess mAb was discarded and the membrane washed 5 times with 0.1% v/v PBS-tween. The washed membrane was incubated with anti-mouse HRP conjugated secondary antibody (Promega, Madison, Wis.) in 1% w/v milk proteins for 30 minutes. Excess antibody was discarded and the membrane washed 5 times with 0.1% v/v PBS-tween before signal development with enhanced chemiluminescence (ECL) Plus reagent (GE Healthcare, Pittsburgh, Pa.) using Hyperfilm ECL X-ray film (GE Healthcare, Pittsburgh, Pa.).

Statistical Methods

Due to a sample size of 14, the BAJA study data were analyzed using the Wilcoxon signed rank non-parametric paired t-test using GraphPad Prism version 5 (La Jolla, Calif., US). The COMP values from the $JOCO_{450}$ cohort were log transformed to achieve a normal distribution before analysis using a generalized linear model, the cumulative logit model. As radiographic data from the left and right joints of a person were likely to correlate, the intra-individual correlation was estimated in the model as a variance component. The cartilage extract data were analyzed either with the Wilcoxon signed rank non-parametric paired t-test for paired data or using the non-parametric Mann-Whitney U test for unpaired data.

Results

Epitope Selection

Putative deamidation hotspots within COMP were identified using the algorithm developed by Robinson and Robinson ("Molecular Clocks: Deamidation of Asparaginyl and Glutaminyl Residues in Peptides and Proteins", Althouse Press (2004)) found at the following website, URL:deamidation[dot]org. This algorithm used the crystal structure and amino acid composition of COMP to predict Asn residues susceptible to deamidation and gave an estimate of the deamidation half-life for each individual Asn residue (CD value× 100 days) and half-life for net deamidation value (ID value× 100 days). As the crystal structure for human COMP was not available at the time of this project, the two partial rat structural files 1fbm.pdb (Guo et al, Embo J. 17(18):5265-5272 (1998)) and 1vdf.pdb (Malashkevich et al, Science 274(5288):761-765 (1996)) publically available in the protein data bank (URL: dot-rcsb- dot-org) were used. Both crystal structures span the N-terminal region of rat COMP between $Gly_{27}$-$Gly_{72}$. Using the two rat terminal structural files, two Asn residues susceptible to deamidation were identified, in human COMP designated $Asn_{42}$ and $Asn_{64}$ (residues 41 and 63 in the rat sequence respectively) (Table 5). Neither of these residues have particularly fast deamidation rates, with $Asn_{41}$ predicted to have a deamidation half-life of between 21-26 years and $Asn_{64}$ of 39-50 years making them ideal markers of degradation of a long-lived tissue such as cartilage matrix degradation. A comparison was made of the sequence alignment for a range of different species available in the NCBI database (URL:ncbi[dot]nlm[dot]nih[dot]gov) and it was confirmed that the predicted Asn deamidation hotspots were contained in human COMP and conserved in a wide range of other animals (Table 5).

TABLE 5

Predicted epitope conservation in different COMP species.
Table 5 discloses SEQ ID NOS 9-20, repsectively, in order of appearance.

| | | | Region 1 ($N_{42}$) | | Region 2 ($N_{64}$) | |
|---|---|---|---|---|---|---|
| Homo sapiens[1] | MVPDTACVLLLTLAALGAS | GQGQSPLGSDLGPQMLR | ELQETNAALQ | DVRELLRQQVREI | TFLKNTVMEC | DACG |
| Rattus norvegicus[2] | MSP TACVLVLALAALRAT | GQGQIPLGGDLAPQMLR | ELQETNAALQ | DVRELLRQQVKEI | TFLKNTVMEC | DACG |
| Mus musculus[3] | MGP TACVLVLALAILRAT | GQGQIPLGGDLAPQMLR | ELQETNAALQ | DVRELLRQQVKEI | TFLKNTVMEC | DACG |
| Canis lupus familiaris[4] | MVPAAACVLLLTLAALGVS | GQGQIPLGADLGPQMLR | ELQETNAALQ | DVRELLRQQVKEI | TFLKNTVMEC | DACG |
| Equus caballus[5] | MVLSAAPVLLLALAALVSS | QGQ TPLGTELGPQMLR | ELQETNAALQ | DVRELLRQQVKEI | TFLKNTVMEC | DACG |
| Bos taurus[6] | MVLAAARVLLLTLAALGAS | GQGQMPLGGDLGPQMLR | ELQETNAALQ | DVRDLLRQQVKEI | TFLKNTVMEC | DACG |
| Pan troglodytes[7] | MVPDTACVLLLTLAALGAS | GQGQSPLGSDLGPQMLR | ELQETNAALQ | DVRELLRQQVREI | TFLKNTVMEC | DACG |
| Sus scrofa[8] | MVLTVARVLLLITLAALGAS | GQGQITLGADLGPQMLR | ELQETNAALQ | DVRELLRQQVKEI | TFLKNTVMEC | DACG |
| Gallus gallus[9] | MISALAFVFLLCLSCPFSSCQQRRA | GIEVGPEMLE | EMRETNRVLM | EVRDLLKQQIKEI | TFLKNTVMEC | DACG |
| Ailuropoda melanoleuca[10] | MVPATACVLLLTLAVLGAS | GQGQISLGADLGPQMLR | ELQETNAALQ | DVRELLRQQVKEI | TFLKNTVMEC | DACG |
| Xenopus tropicalis[11] | MLS VALLSSFCIFFGSCQQLSGRG | DVGPQLLT | EMKETNSVLR | EVRELLKRQIEEI | TFLKNTVMEC | DACG |

TABLE 5-continued

Predicted epitope conservation in different COMP species.
Table 5 discloses SEQ ID NOS 9-20, repsectively, in order of appearance.

|  | Region 1 ($N_{42}$) | Region 2 ($N_{64}$) |
|---|---|---|
| Monodelphis domestica[12] | MPLSPSLGLLLLAFACHLVTGQRQAPVGGDVAPQMLR EMKETNLVLQ | EVRELLKQQIKEI TFLKNTVMEC DACG |

[1]Human, [2]Rat, [3]Mouse, [4]Dog, [5]Horse, [6]Cattle, [7]Chimpanzee, [8]Pig, [9]Red jungle fowl, [10]Giant panda, [11]Western clawed frog, [12]Gray short-tailed opossum To determine whether the predicted deamidated sequences occur in vivo, LC-MS/MS analysis was performed of Gu-HCl extracts from 5 articular cartilage specimens from 3 subjects (extract from one normal hip specimen, and extracts from lesioned and remote cartilage regions of one knee OA and one hip OA specimen). It was not possible to confirm the presence of the predicted deamidation event at $Asn_{42}$ in these samples. However, it was possible to confirm the presence of the native $Asn_{64}$ tryptic peptide ($N_{64}$TVMECDACGMQQSVCR) (SEQ ID NO: 23) and the deamidated $Asp_{64}$ peptide ($D_{64}$TVMECDACGMQQSVCR) (SEQ ID NO: 24) in normal hip and OA hip and knee cartilage (both remote and lesioned regions). In all 5 specimens, the native $Asn_{64}$ peptide was more abundant than the $Asp_{64}$ deamidated peptide (by 83-330 fold) based on intensities of mass spectroscopic traces, with a mean (SD) intensity of 145,178 ±86,144 compared to an intensity of 1,382 ±1,092 for the $Asp_{64}$ deamidated peptide (for a mean 105-fold greater native COMP than D-COMP).

Antibody Generation and Validation

Figure 17:
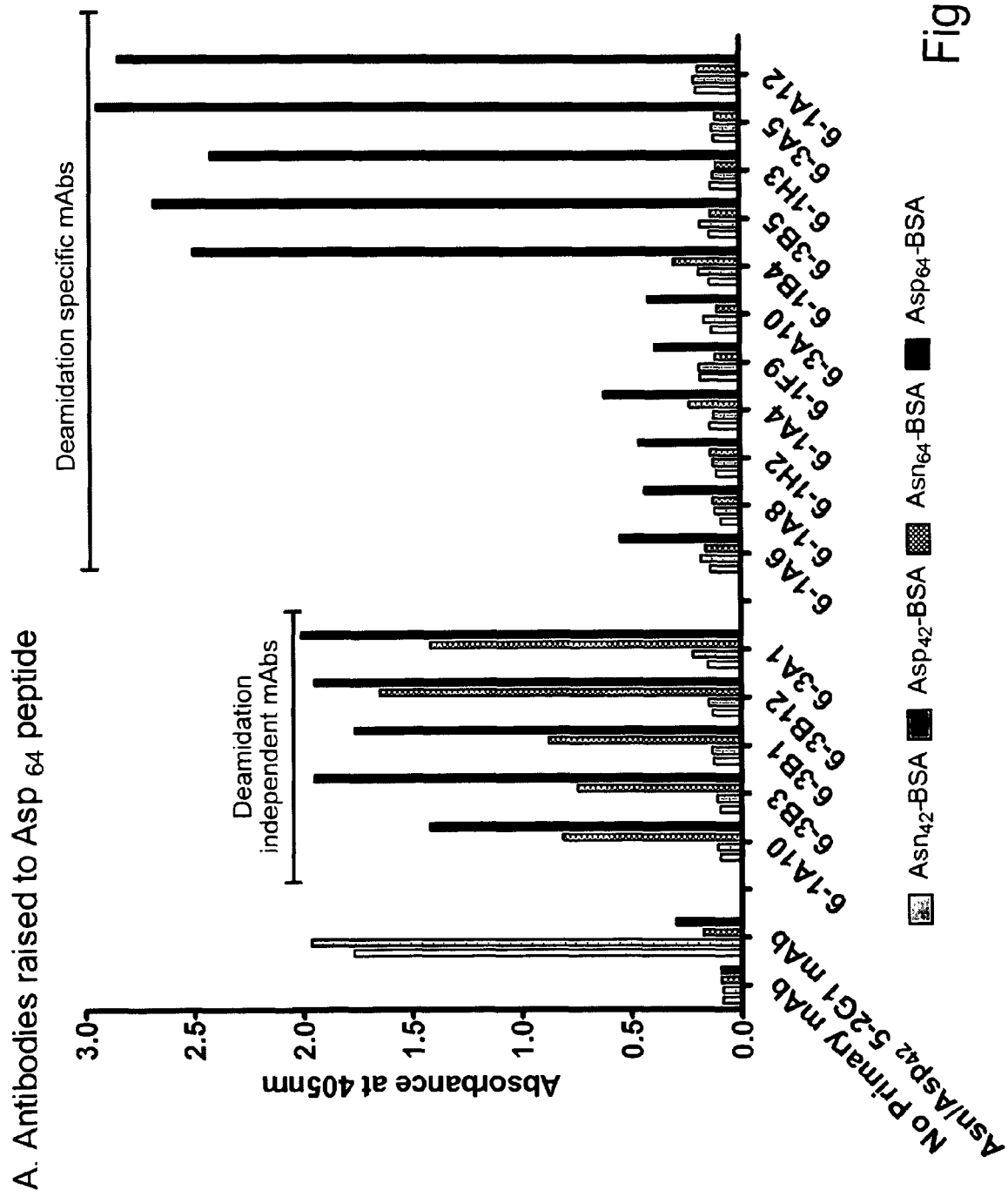
FIGS. 17A-17C. Antibody screening and specificity.
Figure 17:
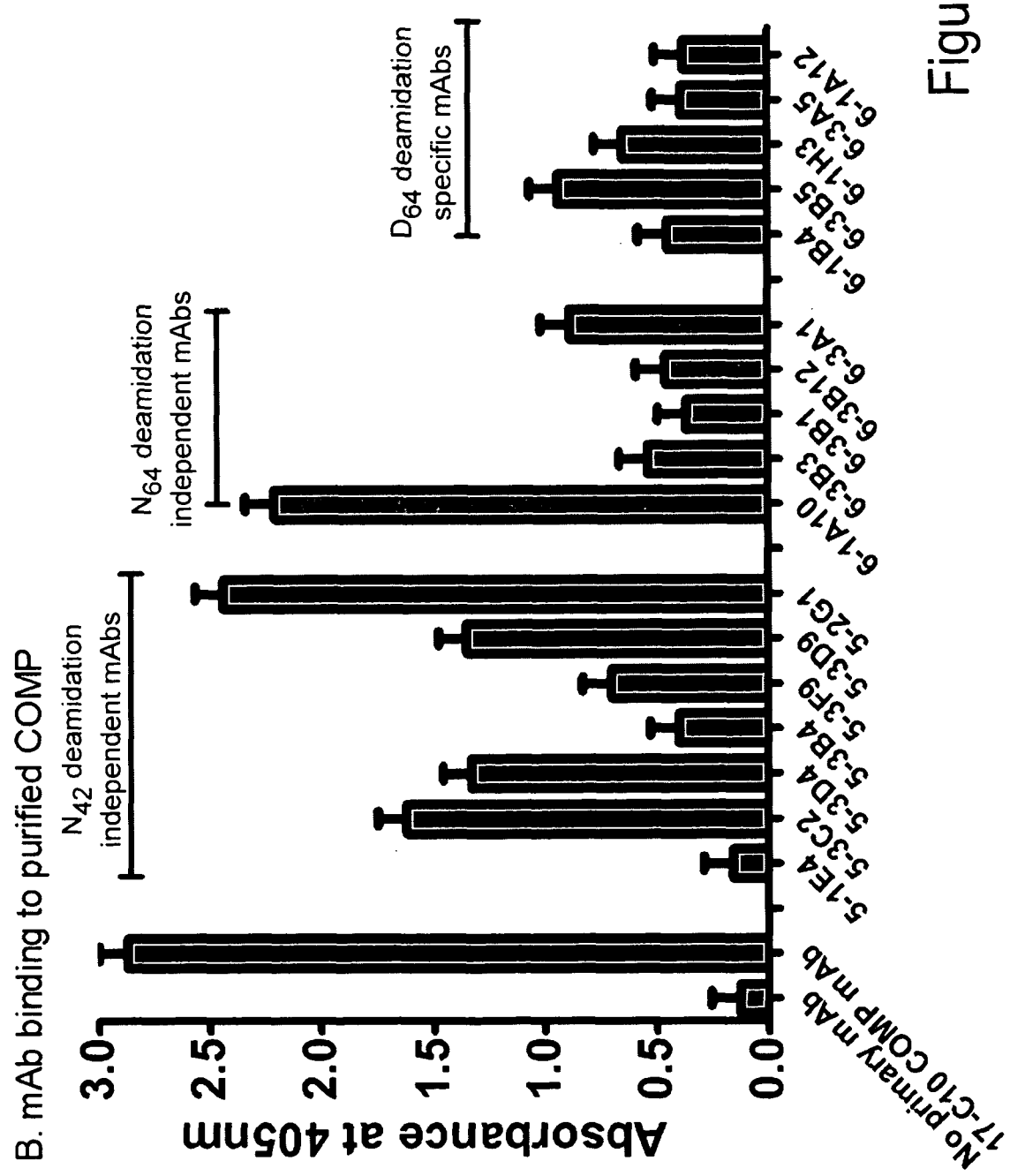
Figure 17:
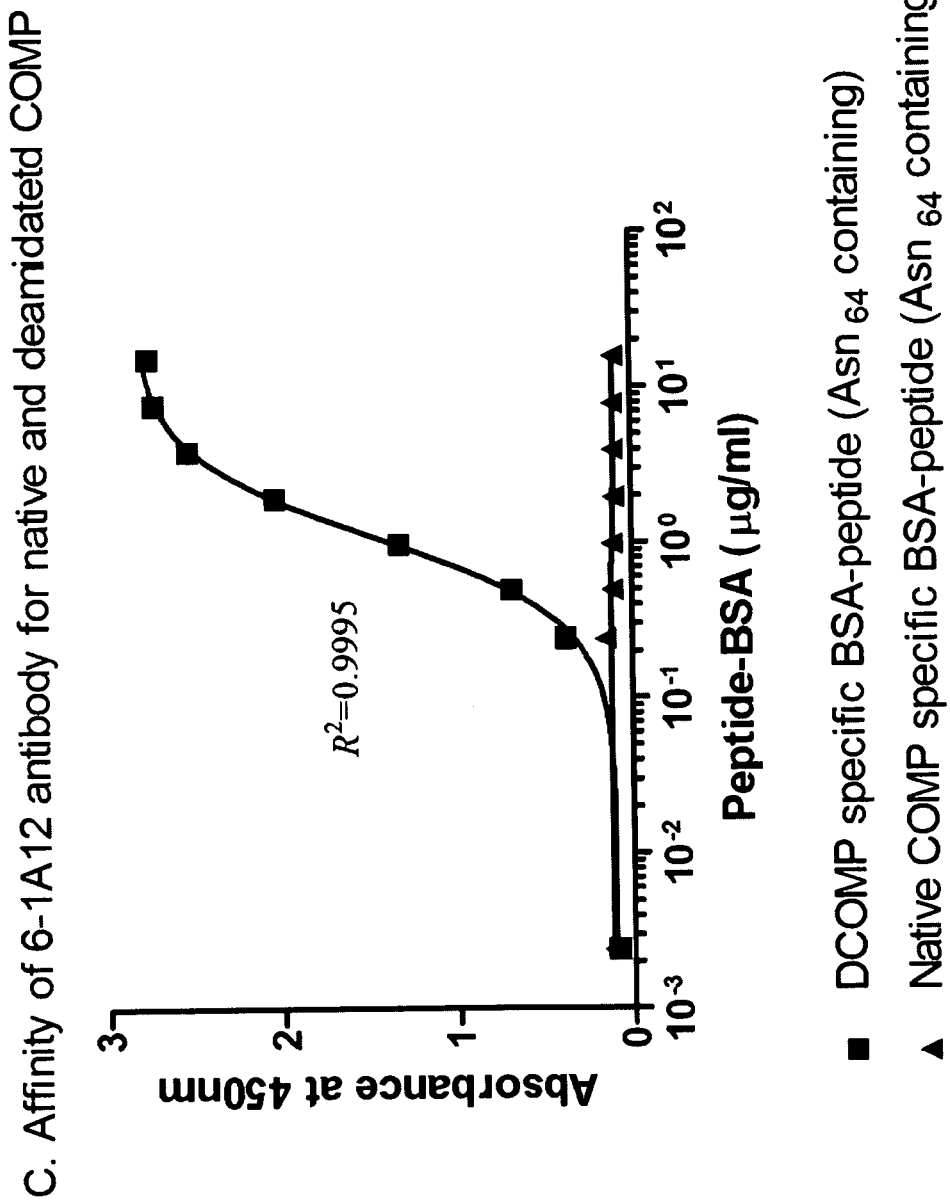

To generate mAbs to deamidated epitopes in COMP, mice were immunized with a peptide containing $Asp_{64}$ (TFLKD$_{64}$TVMEC (SEQ ID NO:3) found in deamidated COMP. Using this approach it was expected that two classes of mAbs would be generated, those which recognized the deamidated $Asp_{64}$ residue and mAbs which were deamidation independent, recognizing both the amidated and deamidated sequence. 16 mAb clones were identified that recognized the immunogen. To determine the specificities of these 16 clones, a comparison was made of their immunoreactivity to 4 different BSA conjugated COMP peptides: the $Asp_{64}$ (TFLKD$_{64}$TVMEC (SEQ ID NO:3)) immunogen, native $Asn_{64}$ (TFLKN$_{64}$TVMEC (SEQ ID NO:4)), deamidated $Asp_{42}$ (CELQETD$_{42}$AALQ) (SEQ ID NO:7), and native $Asn_{42}$ (CELQETN$_{42}$AALQ) (SEQ ID NO: 6) (FIG. 17A). As anticipated, two main types of mAbs were identified using this approach, mAbs that appeared to be deamidation independent as they recognized both the $Asn_{64}$ and $Asp_{64}$ containing BSA constructs (clones 6-1A10, 6-3B3, 6-3B1, 6-3B12 and 6-3A1), and deamidation specific clones (clones 6-1A6, 6-1A8, 6-1H2, 6-1A4, 6-1F9, 6-1A10, 6-1B4, 6-3B5, 6-1H3, 6-3A5 and 6-1A12). None of the 16 clones raised to the $Asp_{64}$ peptide bound the BSA coupled $Asn_{42}$ or $Asp_{42}$ control peptides; the immunoreactivity of these control peptides was confirmed by reactivity with mAb (5-3D4) raised specifically to the $Asp_{42}$ containing peptide (FIG. 17A).

To confirm that the mAbs recognized COMP from human cartilage and not just peptides, they were screened by ELISA against COMP purified from human hip cartilage pooled from 2 subjects (gift from V. Vilm (Vilim et al, Clin. Chim. Acta 328(1-2):59-69 (2003))) (FIG. 17B). All 16 mAbs displayed higher than background immunoreactivity to cartilage COMP. Of note, the mAb preparations used in these validation experiments were not purified so the apparent differences in immunoreactivity could reflect mAb concentration rather than mAb affinity. In addition, the fact that the deamidation specific mAbs reacted to cartilage COMP suggested sufficient sensitivity on the part of these antibodies to identify the presence of $Asp_{64}$ deamidated COMP purified from human articular cartilage.

Figure 18:
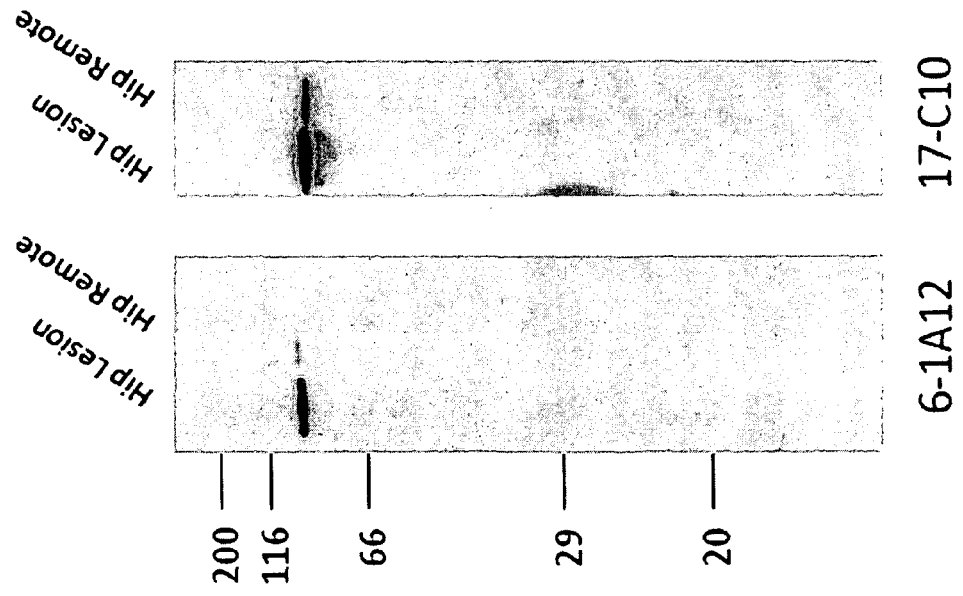
FIG. 18. Western blot analysis of cartilage extract with 17-C10 total COMP mAb and the 6-1A12 deamidated COMP epitope specific mAb. Gu-HCL were prepared from age matched osteoarthritic hip and knee cartilages harvested from both OA lesional sites and remote from the lesion in macroscopically normal appearing cartilage. Prior to SDS-PAGE separation on a 10% gel, samples were dialyzed into PBS, protein levels determined, and 5 μg/well of protein loaded per well. Samples were separated under standard conditions and transferred to nitrocellulose which was blocked with 3% milk proteins prior to antibody incubation and development with ECL reagents. For clarity, the total COMP membrane was exposed for a shorter time period (30 second) while the D-COMP, due to it lower levels, required a longer exposure (5 minutes).

The $Asp_{64}$ deamidation specific 6-1A12 mAb was selected for use in all further experiments detailed in this study. The specificity and affinity of the 6-1A12 mAb were further confirmed against the native and deamidated BSA-peptides (FIG. 17C). It was demonstrated that the 6-1A12 mAb had no affinity for the native Asn64 containing sequence but instead had a high affinity for only the deamidated COMP specific $Asp_{64}$ containing peptide. To further confirm that the 6-1A12 mAb recognized COMP extracted from cartilage and not just a COMP specific peptide, a reduced Western blot of an OA hip cartilage Gu-HCl extract was performed (FIG. 18). The deamidation specific 6-1A12 mAb detected a 110 kDa protein that corresponded to both a band of similar molecular weight detected by established anti-COMP mAb 17-C10 (Vilim et al, Archives of biochemistry and Biophysics 341(1): 8-16 (1997)), and that corresponded to the size of monomeric COMP.

Changes in Levels of D-COMP and Total COMP after Joint Arthroplasty

Figure 19:
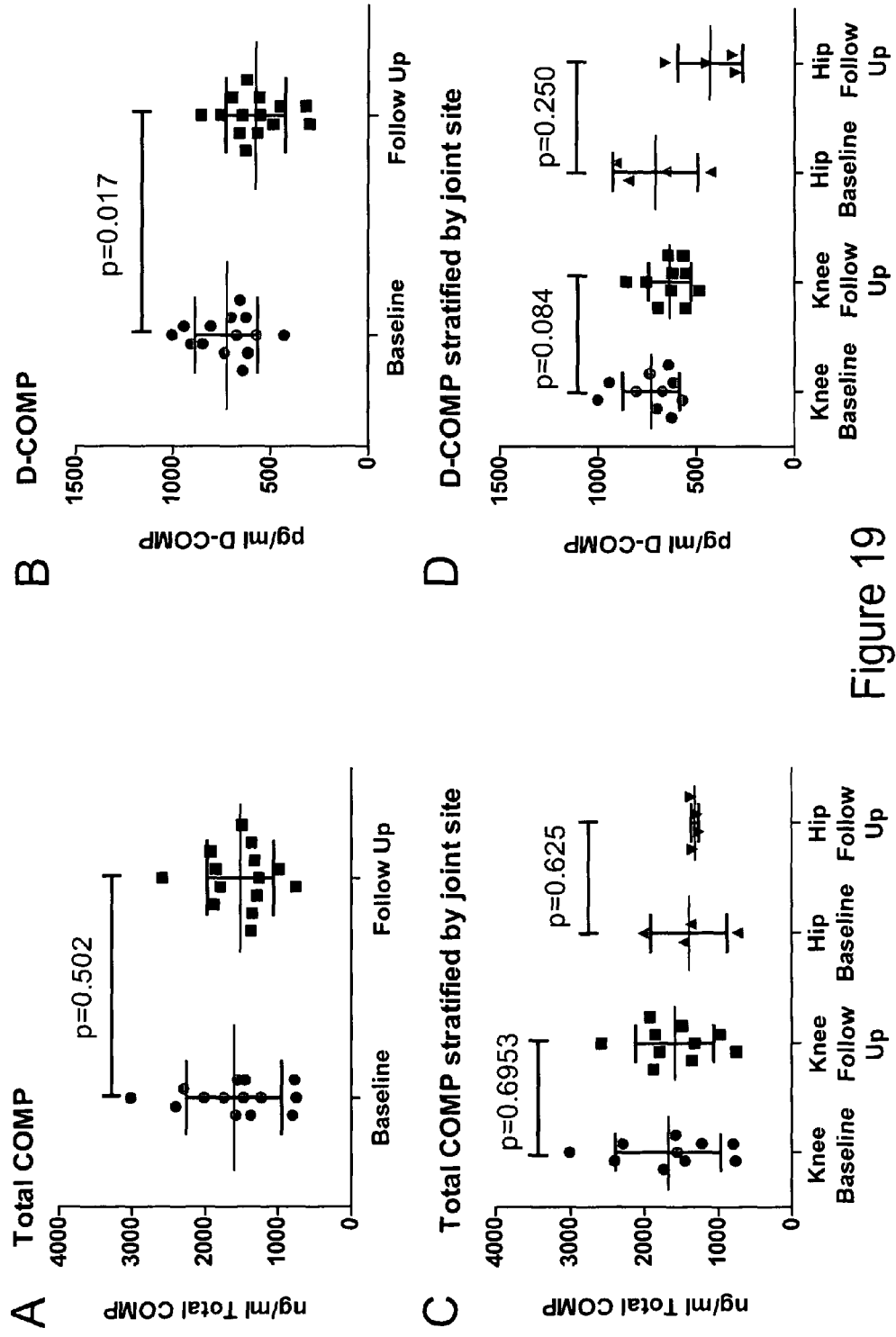
FIGS. 19A-19D. D-COMP but not Total COMP declines following replacement of osteoarthritic joints. Sera were obtained before and 6 months after joint arthroplasty. Total serum COMP and serum D-COMP were measured by sandwich ELISA at baseline (prior to joint replacement) and at follow up (6 months post-joint replacement) for n=14 patents (9 knee and 5 hip replacements). Significant differences were determined using the paired non-parametric Wilcoxon signed rank test. Monoclonal antibody pairs used for D-COMP were 6-1A12 capture and 17-C10 detection; for total COMP 16-F12 capture and 17-C10 detection.

In the BAJA study, blood (n=14) was collected before joint replacement (baseline samples) and 6 months after either hip (n=4) or knee (n=10) total arthroplasty. Both total COMP and the D-COMP were measured. It was expected that a decrease in the serum concentrations of these biomarkers after joint arthroplasty would be observed, thereby supporting in principle, a joint tissue source for the measured biomarker in the serum. Total serum COMP after joint replacement was not significantly changed from baseline (baseline 1,600±655 ng/ml, 6 month follow-up 1,513±457 ng/ml, p=0.502) (FIG. 19A). However, a small but significant decrease in the serum concentrations of D-COMP was observed after joint replacement compared with baseline (baseline 726±158 pg/ml, 6 month follow-up 578.6±154 pg/ml, p=0.017) (FIG. 19B). When the data were stratified by joint site, a small but non-significant decreasing trend for D-COMP following knee replacement was observed (23% mean decline from 732 pg/ml±48 at baseline and 638 pg/ml±34 at follow up) and a larger decreasing trend for D-COMP following hip replacement (39% mean decline from 711 pg/ml±108 baseline and 431 pg/ml±83) (FIG. 19D). There was minimal change in total COMP stratified by joint site for knee (5% mean decline from 1680 ng/ml±225 baseline and 1593 ng/ml±166 follow up) or hip (6% mean decline from 1400 ng/ml±260 baseline and 1316 ng/ml±26 follow up) (FIG. 19C).

Figure 20:
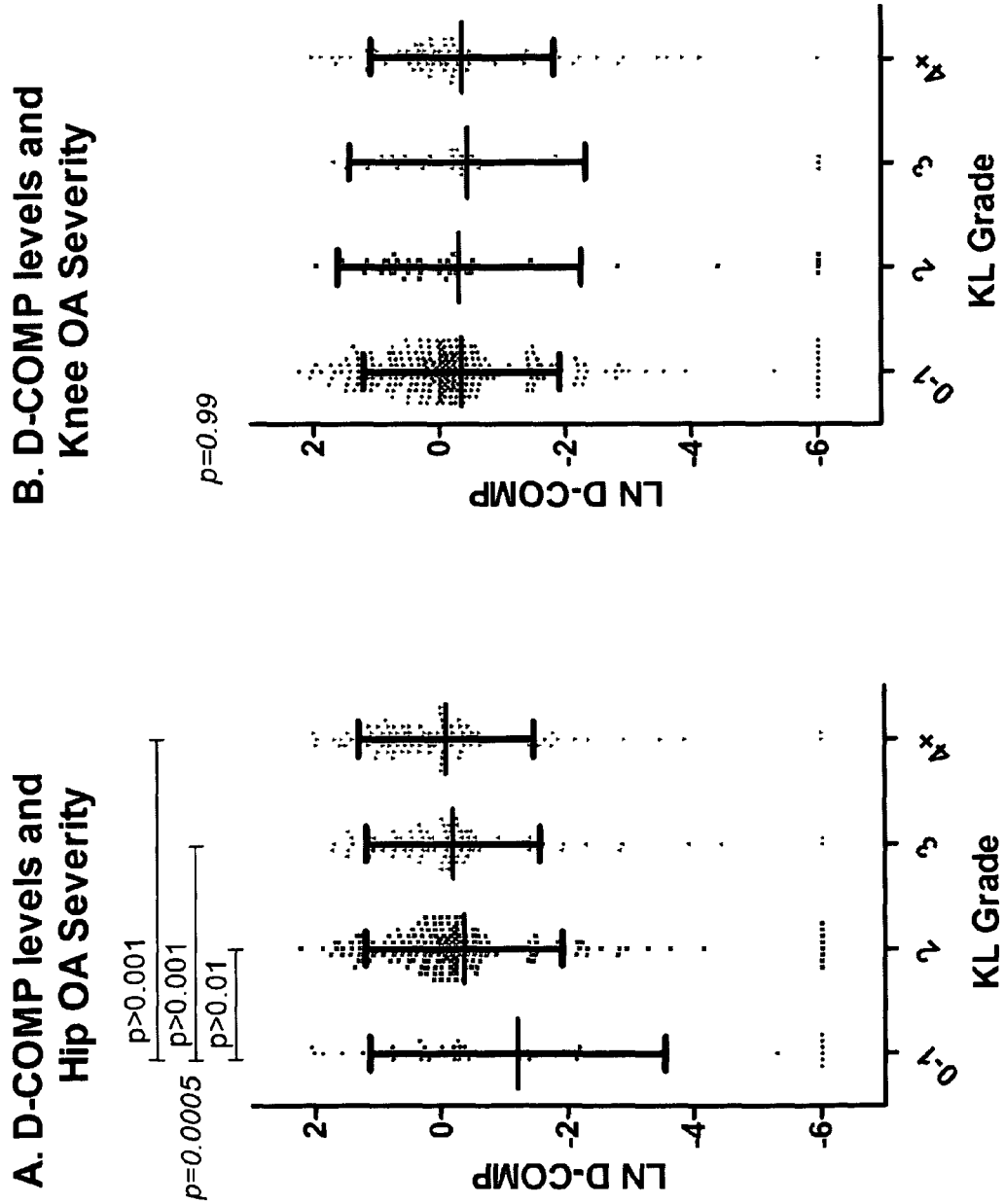
FIGS. 20A-20D. The association of D-COMP and Total COMP serum levels with hip and knee OA in the JoCo$_{450}$ cohort samples. Sera and X-rays of both hip and knee were obtained for 450 subjects from the JoCo cohort. X-rays were read for OA status as defined by KL grade (0-4 scale) with OA being defined as KL grade ≥2. For the purposes of this analysis, the KL scores were summed for both hips and both knees (total possible range of 0-8). Serum levels for both D-COMP and Total COMP were determined and the data log transformed for statistical purposes. The data are represented as scatter plots showing the mean±SD for non OA subjects (KL0-1), early OA (KL2 and KL3) and for advanced OA (KL4+).

Levels of D-COMP and Total COMP in Hip and Knee OA Subjects of the $JoCo_{450}$ Cohort To further investigate the utility of D-COMP as a potential biomarker in OA, total COMP and D-COMP were measured in the $JOCO_{450}$ subsample of patients. This sample subset was derived from the population based JoCo study (Jordan et al, Arthritis Care and Res. 8(4):242-250 (1995)). The total subsample included 900 knees and 900 hips, graded for radiographic OA severity by Kellgren-Lawrence (KL) grade. Statistical analyses used generalized linear models (cumulative logit models) controlling for the intra-individual correlation in the model as a component of variation. Knee OA occurred with the following frequencies; 535 KL0, 153 KL1, 115 KL2, 81 KL3, 14 KL4 and 2 knee replacements. Hip OA occurred with the following frequencies; 73 KL0, 512 KL1, 287 KL2, 20 KL3, 4 KL4 and 4 hip replacements. Total COMP was significantly associated with knee OA KL grade ($p<0.0001$), but not hip KL grade ($p=0.47$). In contrast, D-COMP was significantly associated with hip OA KL grade ($p<0.0001$) but not with knee OA KL grade ($p=0.95$). For knee OA, also available were the scores for radiographic OA features of joint space narrowing and osteophyte. Total COMP was strongly associated both knee joint space narrowing ($p<0.0001$) and knee osteophyte ($p<0.0001$) while D-COMP was not. To provide a graphic representation of the results, D-COMP values are shown in box plots stratified by knee and hip OA status (FIG. 20). These data strongly suggest that the new serum D-COMP assay is a new biomarker indicative of the presence and severity of hip OA whereas total COMP is an indicator of the presence and severity of knee OA.

Levels of D-COMP and Total COMP in Osteoarthritic Hip and Knee Cartilage

Figure 21:
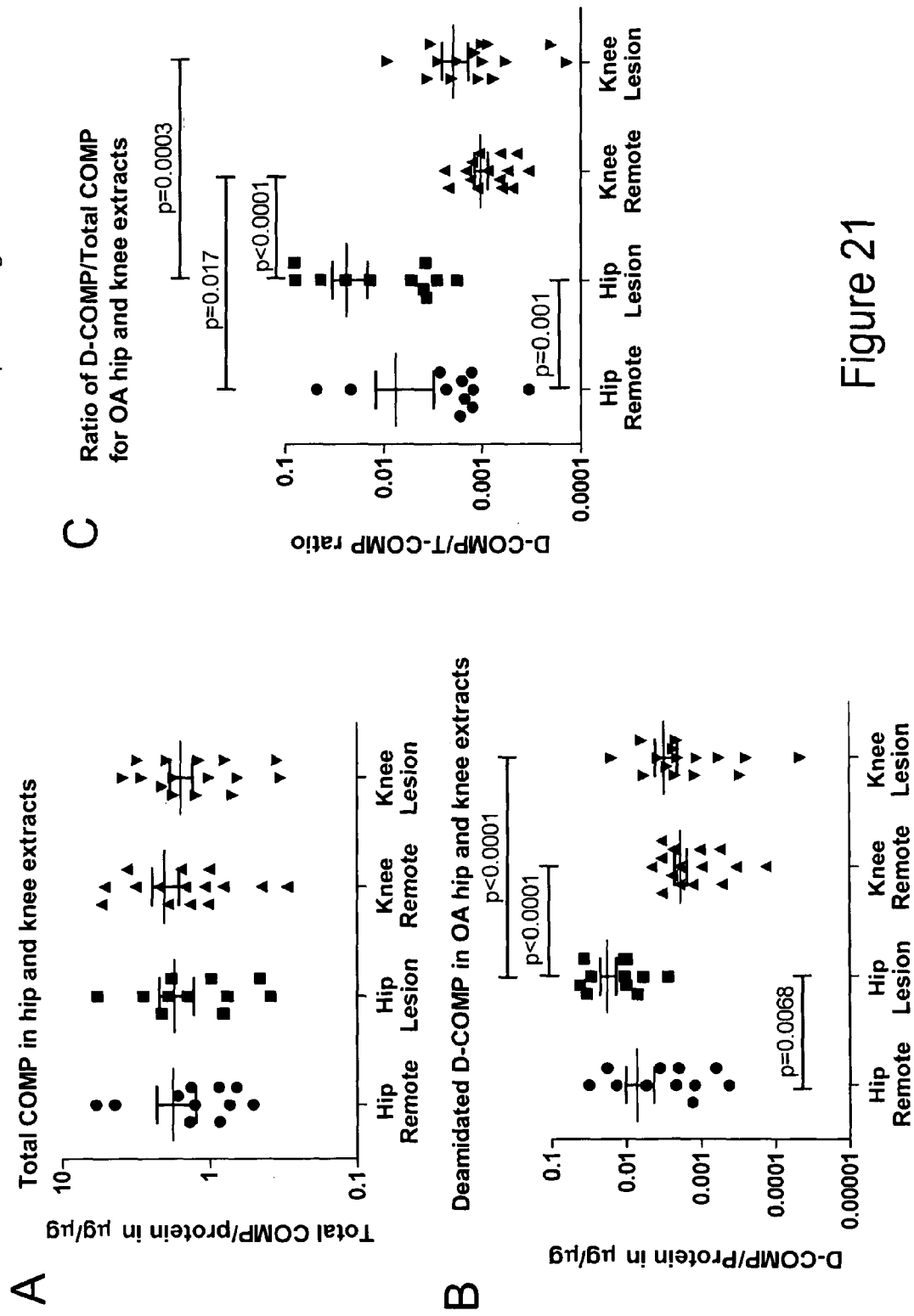
FIGS. 21A-21C. Total COMP and D-COMP levels in extracts from hip and knee cartilage. Soluble proteins were extracted from cartilage using 4M Gu-HCl before buffer exchange into PBS to allow further analysis. Total COMP (FIG. 21A) and D-COMP (FIG. 21B) were measured by sandwich ELISA as described in FIG. 19, and normalized to total protein to correct for variations in the extraction and dialysis efficiency. The ratio of D-COMP/Total COMP (FIG. 21C) was calculated as a measure that is independent of technical variation due variation in protein extraction and dialysis efficiency. Statistical differences were determined using non-parametric statistics. For paired samples (remote and lesion within a joint), the Wilcoxon signed rank test was used; for non-paired samples (hip and knee joint comparisons) intergroup significance was determined using the non-parametric Mann-Whitney U test. D-COMP and the D-COMP/Total COMP ratio were higher in hip than knee cartilages and higher in hip OA lesions than macroscopically normal appearing hip remote from lesions.

To better understand the results from the $JOCO_{450}$ cohort and the relationship between D-COMP and hip OA, an investigation was made of the levels of D-COMP and total COMP in Gu-HCl extracts from osteoarthritic hip (n=11) and knee samples (n=15) collected as waste surgical tissue at the time of joint arthroplasty. Soluble proteins were extracted from regions of hip and knee cartilages adjacent to OA lesions, and from regions of the same joint remote from the OA lesion that appeared macroscopically normal. All values were normalized to total protein content to control for variations in protein extraction efficiencies and dialysis variations. The ratio of D-COMP/Total COMP was evaluated as a measure free from confounding by extraction efficiencies and dialysis variations. Total COMP did not vary by joint site (lesion or remote) or joint group (knee or hip) (FIG. 21A). However, D-COMP was significantly higher in hip vs knee lesion cartilage (mean±SD, 0.018±0.015 and 0.003±0.004 µg D-COMP/µg protein extracted respectively, $p<0.0001$) and a similar but not significant trend was observed for D-COMP in hip remote vs knee remote cartilage (mean±SD, 0.007±0.01 and 0.002±0.001 µg D-COMP/µg extracted protein respectively, $p=0.14$) (FIG. 21B). D-COMP was significantly higher ($p=0.001$) in the hip lesional cartilage compared with the macroscopically normal remote hip cartilage and remote knee cartilage (mean±SD of 0.007±0.01, 0.018±0.014, and 0.002±0.014 µg D-COMP/µg extracted protein respectively). These data confirm that the D-COMP epitope is more abundant in hip than knee cartilage and is enriched at the site of OA lesions in the hip.

To better understand the turnover of COMP at the different sites, the ratio of aged D-COMP/Total COMP was evaluated (FIG. 21C). The D-COMP/Total COMP ratio was highest in hip OA lesional cartilage, and higher at the hip lesion vs any of the other regions, namely vs the macroscopically normal appearing hip remote ($p=0.001$), knee remote ($p<0.0001$), or knee lesion ($p=0.0003$) cartilage (mean±SD, 0.024±0.03 hip lesion, 0.008±0.015 hip remote, 0.001±0.0006 knee remote, and 0.002±0.002 knee lesion). A significantly higher D-COMP/Total COMP ratio was observed between hip remote and knee remote cartilage (mean±SD, 0.008±0.015 and 0.001±0.0006 D-COMP/Total COMP respectively, $p=0.017$) consistent with lower lower rates of COMP synthesis, and so older tissue in the hip, and the least amount of COMP synthetic repair at hip OA lesions.

In summary, as part of cartilage homeostasis, cartilage proteins are continually degraded and replaced by the chondrocytes. This matrix turnover happens most rapidly in the vicinity of the cells (Handley et al, "Steady-state metabolism in cartilage explants" in: Articular Cartilage Biochemistry, eds Kuettner et al, New York: Raven Press, pgs. 163-179 (1986)) and is greatly reduced in the interterritorial matrix that is further removed from the cells. The proof of this concept so far has been demonstrated only for the proteoglycan component of cartilage (Mok et al, J. Biol. Chem. 269 (52):33021-33027 (1994)). As there is very little protein turnover within the interterritorial matrix, the collagen found within this region is believed to be the longest lived and so the most susceptible to age-related post-translational damage. Turnover also varies with distance from the articular cartilage surface (Mok et al, J. Biol. Chem. 269(52):33021-33027 (1994)), age (Sandy and Plaas, Journal of Orthopaedic Research 4(3):263-272 (1986)), and between different cartilage matrix molecules. For instance, proteoglycans such as aggrecan, turnover much more quickly (3-25 years) (Maroudas et al, Archives of Biochemistry and Biophysics 350(1): 61-71 (1998)) than the collagen molecules (half-life 100-400 years) (Maroudas et al, Connective Tissue Research 28(3): 161-169 (1992), Verzijl et al, J. Biol. Chem. 275(50):39027-39031 (2000)).

The above-described study demonstrates a biomarker associated with OA at a particular large joint site. Two explanations are believed possible for the higher D-COMP levels in the hip lesion than the remote tissue. Firstly there could be accelerated production of D-COMP at the lesion site, or, secondly, the cartilage at the lesion may have lost the superficial and medial zones leaving only the older deep zone region, which leads to enrichment and 'biological aging' of the remaining tissue. The latter interpretation is favored since, relative to hip OA lesions, knee OA lesions were not enriched for D-COMP, arguing against increased rates of deamidation purely due to the OA disease process. The clear differences in D-COMP concentrations at macroscopically normal hip and knee cartilage are consistent with different rates of biological aging in these two large joint sites and overall less COMP synthesis in hips than knees. Hip OA cartilage lesions in particular, were differentially enriched for D-COMP. This is compatible both with loss of the more rapidly regenerating superficial layers and failure to repair, with adequate new COMP synthesis, the remaining deep layers of hip OA cartilage.

It was possible to generate deamidation dependent (to the $Asn_{64}$ to $Asp_{64}$ deamidation event) and independent (to $Asn_{52}$ and $Asn_{64}$ epitopes) mAbs to COMP regions. Because COMP may enhance the availability of hydrophobic growth factors and vitamin D3 in cartilage by increasing their local concentration in this avascular tissue (Ozbek et al, Embo J. 21(22): 5960-5968 (2002)), it would be of great interest to determine the functional consequences and impact on vitamin D3 binding imposed by this deamidation event at amino acid 64 which is located within the pore forming domain of COMP.

It was noted that D-COMP, but not total COMP, declined following joint replacement. These results with total COMP are consistent with observations made previously by Sharif et al (Arthritis Rheum. 50(8):2479-2488 (2004)) who showed that total COMP increased for at least 6 months following joint replacement rather than declined. These results are compatible with previous reports of COMP production by osteoblasts (Leslie et al, Trans. Orthop. Res. 24:581 (1999)) and the potential for elevated COMP during the period of reactive bone repair following joint arthroplasty. Very interestingly, by 6 months after joint replacement, D-COMP did not suffer from the same confounding effect. It will be of interest to evaluate samples at earlier, time points after joint replacement to determine the kinetics of D-COMP decline with respect to the immediate post-op period.

All documents and other information sources cited above are hereby incorporated in their entirety by reference.

What is claimed is:

1. A method of diagnosing hip osteoarthritis in a test subject suspected of having osteoarthritis, said method comprising:
   i) obtaining a serum sample from the test subject.
   ii) quantitating a total amount of COMP protein fragments that comprise an amino acid sequence consisting of SEQ ID NO: 3 by contacting the serum sample with an antibody or antigen-binding fragment thereof that specifically recognizes SEQ ID NO: 3 to form a complex, wherein the antibody is produced by a hybridoma having a deposit accession number selected from the group consisting of PTA-11688, PTA-11690, PTA-11686, and PTA-11687; and
   iii) comparing the total amount of COMP protein fragments quantitated in step (ii) to a control level of COMP protein fragments that comprise the amino acid sequence consisting of SEQ ID NO: 3, wherein the control level is calculated in a serum sample obtained from an age matched sample from subjects not having hip osteoarthritis, and wherein a statistically significant increase of COMP protein fragments in step (ii) in the sample from the test subject relative to the control level is indicative of hip osteoarthritis in the test subject.

2. The method of claim 1 wherein the antibody in step (ii) is produced by hybridoma having deposit accession number PTA-11688.

3. The method of claim 1 wherein step (ii) further comprises contacting the complex with a second antibody or antigen binding fragment thereof, wherein the second antibody is produced by a hybridoma having a deposit accession number selected from the group consisting of PTA-11684, PTA-11685, and PTA-11689.

4. The method of claim 3 wherein the second antibody is produced by hybridoma PTA-11684.

* * * * *